US012605388B2

(12) United States Patent
Hunt et al.

(10) Patent No.: US 12,605,388 B2
(45) Date of Patent: Apr. 21, 2026

(54) LAMOTRIGINE SALTS, CO-CRYSTALS, AND COMPOSITIONS

(71) Applicant: Azurity Pharmaceuticals Ireland Limited, Dublin (IE)

(72) Inventors: Jordan R. Hunt, Prairie Village, KS (US); Gerold Mosher, Kansas City, MO (US); Paras P. Jain, Amaravati (IN); Krishna Mohan Lakshmipathula, Hyderabad (IN)

(73) Assignee: AZURITY PHARMACEUTICALS IRELAND LIMITED, Dublin (IE)

( * ) Notice: Subject to any disclaimer, the term of this patent is extended or adjusted under 35 U.S.C. 154(b) by 0 days.

(21) Appl. No.: 19/053,770

(22) Filed: Feb. 14, 2025

(65) Prior Publication Data

US 2026/0083745 A1 Mar. 26, 2026

Related U.S. Application Data

(60) Provisional application No. 63/758,257, filed on Feb. 13, 2025, provisional application No. 63/756,940, filed on Feb. 11, 2025, provisional application No. 63/698,821, filed on Sep. 25, 2024.

(51) Int. Cl.
*A61K 31/53* (2006.01)
*C07C 57/15* (2006.01)
*C07D 253/075* (2006.01)

(52) U.S. Cl.
CPC .............. *A61K 31/53* (2013.01); *C07C 57/15* (2013.01); *C07D 253/075* (2013.01)

(58) Field of Classification Search
CPC ...................................................... A61K 31/53
See application file for complete search history.

(56) References Cited

U.S. PATENT DOCUMENTS

| | | | | |
|---|---|---|---|---|
| 4,602,017 | A * | 7/1986 | Sawyer | C07C 51/363 544/182 |
| 4,847,249 | A | 7/1989 | Sawyer et al. | |
| 4,886,669 | A | 12/1989 | Ventouras | |
| 5,629,312 | A | 5/1997 | Bousseau et al. | |
| 5,658,900 | A | 8/1997 | Boireau et al. | |
| 5,658,905 | A | 8/1997 | Critchley | |
| 5,660,861 | A | 8/1997 | Jao et al. | |
| 5,698,226 | A | 12/1997 | Fielden | |
| 5,712,277 | A | 1/1998 | Nakamura-Craig et al. | |
| 5,801,171 | A | 9/1998 | Nakamura-Craig | |
| 5,830,907 | A | 11/1998 | Doble et al. | |
| 5,861,179 | A | 1/1999 | Hiskett et al. | |
| 5,866,597 | A | 2/1999 | Baxter | |
| 5,942,510 | A * | 8/1999 | Floyd | A61K 9/19 514/242 |
| 6,333,198 | B1 | 12/2001 | Edmeades et al. | |
| 6,548,507 | B1 | 4/2003 | Bountra et al. | |
| 6,861,426 | B2 | 3/2005 | Garti et al. | |
| 7,101,572 | B2 | 9/2006 | Santos et al. | |
| 7,371,405 | B2 | 5/2008 | Bunick et al. | |
| 7,521,553 | B2 | 4/2009 | Parthasaradhi et al. | |
| 7,678,551 | B2 | 3/2010 | Ouyang et al. | |
| 8,486,927 | B2 | 7/2013 | Hanna et al. | |
| 8,725,243 | B2 | 5/2014 | Dilorenzo et al. | |
| 8,906,919 | B2 | 12/2014 | Smith et al. | |
| 9,066,949 | B2 | 6/2015 | Conour | |
| 9,198,862 | B2 | 12/2015 | Pilgaonkar et al. | |
| 9,730,884 | B2 | 8/2017 | Marathi et al. | |
| 9,884,015 | B2 | 2/2018 | Gao et al. | |
| 10,028,971 | B2 | 7/2018 | Bird | |
| 10,309,967 | B2 | 6/2019 | Hashimoto et al. | |
| 10,576,086 | B2 | 3/2020 | Harbige et al. | |
| 10,653,626 | B2 * | 5/2020 | Lu | A61K 9/0095 |
| 11,447,456 | B1 | 9/2022 | Li, Sr. et al. | |
| 11,596,634 | B2 | 3/2023 | Sudhakar et al. | |
| 11,648,231 | B2 | 5/2023 | Poras et al. | |
| 2004/0023962 | A1 | 2/2004 | Etheridge | |
| 2004/0209960 | A1 | 10/2004 | Burgard et al. | |

(Continued)

FOREIGN PATENT DOCUMENTS

| | | | |
|---|---|---|---|
| CN | 104873461 | A | 9/2015 |
| CN | 104940128 | A | 9/2015 |

(Continued)

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*
"Find ETDs Home » Thesis Resources » Find ETDs" Online: "https://ndltd.org/thesis-resources/find-etds/" Accessed Jan. 31, 2023.*
Irwin "ZINC—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*
STN Registry/Zregistry (CAS Registrysm) Sep. 2016 2 pages.*
Chappa, Materials Today: Proceedings 14 (2019) 504-513.*
Galcera, Crystal Growth & Design (2009), 9(1), 327-334.*

(Continued)

*Primary Examiner* — Nizal S Chandrakumar
(74) *Attorney, Agent, or Firm* — McNeill PLLC

(57) ABSTRACT

The present disclosure relates to novel lamotrigine salts, co-crystals, and compositions. In some embodiments, the lamotrigine salt is a lamotrigine dicarboxylic acid salt or hydrate or solvate thereof. In some embodiments, the lamotrigine co-crystal is a co-crystal of lamotrigine and a dicarboxylic acid, or a hydrate or solvate thereof. In some embodiments, the compositions comprise lamotrigine or a salt or co-crystal thereof, or a hydrate or solvate thereof. In some embodiments, the composition is in the form of a powder. In some embodiments, the composition is in the form of a liquid. The present disclosure also relates to methods of preparation and use in medical therapy, for example, for the treatment of a subject with epilepsy or bipolar disorder.

12 Claims, 12 Drawing Sheets

(56) References Cited

U.S. PATENT DOCUMENTS

| | | | |
|---|---|---|---|
| 2004/0213842 | A1 | 10/2004 | Burgard et al. |
| 2005/0118205 | A1 | 6/2005 | Ulrich et al. |
| 2005/0136105 | A1 | 6/2005 | Allen et al. |
| 2005/0238724 | A1 | 10/2005 | Aronhime et al. |
| 2007/0104791 | A1 | 5/2007 | Popov et al. |
| 2007/0135412 | A1 | 6/2007 | Martinez et al. |
| 2007/0148211 | A1 | 6/2007 | Altreuter et al. |
| 2008/0138383 | A1 | 6/2008 | Bortz et al. |
| 2008/0248117 | A1 | 10/2008 | Kolter et al. |
| 2008/0269223 | A1 | 10/2008 | Chakravorty et al. |
| 2009/0004254 | A1 | 1/2009 | Maibach |
| 2009/0022789 | A1 | 1/2009 | Kidane et al. |
| 2009/0076010 | A1 | 3/2009 | Czarnik |
| 2009/0304795 | A1 | 12/2009 | Bernigal et al. |
| 2010/0016322 | A1 | 1/2010 | Nagaraju et al. |
| 2010/0105688 | A1 | 4/2010 | Alvaro et al. |
| 2010/0222311 | A1 | 9/2010 | Thommes et al. |
| 2010/0286080 | A1 | 11/2010 | Badwan et al. |
| 2012/0142919 | A1 | 6/2012 | Arnalot Aguilar |
| 2014/0142140 | A1 | 5/2014 | Bird |
| 2015/0182457 | A1 | 7/2015 | Huang et al. |
| 2017/0224834 | A1 | 8/2017 | Leighton et al. |
| 2019/0060237 | A1 | 2/2019 | Lu et al. |
| 2020/0000755 | A1 | 1/2020 | Guedes et al. |
| 2020/0046716 | A1 | 2/2020 | Mehta et al. |
| 2020/0315962 | A1 | 10/2020 | Endo et al. |
| 2020/0318189 | A1 | 10/2020 | Hung et al. |
| 2020/0375995 | A1 | 12/2020 | Sudhakar et al. |
| 2021/0052539 | A1 | 2/2021 | Poras et al. |
| 2021/0069109 | A1 | 3/2021 | Sudhakar et al. |
| 2023/0190759 | A1 | 6/2023 | Sudhakar et al. |
| 2024/0207280 | A1 | 6/2024 | Li et al. |
| 2024/0261293 | A1 | 8/2024 | Zheng et al. |
| 2024/0342183 | A1 | 10/2024 | Sudhakar et al. |
| 2025/0144106 | A1 | 5/2025 | Tu et al. |

FOREIGN PATENT DOCUMENTS

| | | | |
|---|---|---|---|
| CN | 104940930 | A | 9/2015 |
| CN | 106491539 | A | 3/2017 |
| CN | 113456603 | A | 10/2021 |
| CN | 115068422 | A | 9/2022 |
| CN | 116531324 | A | 8/2023 |
| EP | 0674518 | A1 | 10/1995 |
| EP | 0948325 | | 10/1999 |
| EP | 1175209 | | 1/2002 |
| EP | 1190720 | B1 | 3/2004 |
| EP | 1608342 | A2 | 12/2005 |
| EP | 1700616 | | 9/2006 |
| EP | 1035838 | B1 | 8/2007 |
| EP | 2249807 | A2 | 11/2010 |
| EP | 2656857 | | 10/2013 |
| EP | 3258925 | | 12/2017 |
| GB | 2569615 | A | 6/2019 |
| IN | 427MUM2005 | | 3/2007 |
| IN | 055MUM2004 | | 6/2007 |
| IN | 1711MUM2006 | | 7/2008 |
| IN | 1148MUM2009 | | 11/2010 |
| IN | 201911004379 | | 2/2019 |
| MX | PA03008841 | A | 4/2005 |
| MX | 401622 | B | 5/2023 |
| WO | 19940015607 | | 7/1994 |
| WO | 2004103340 | A1 | 12/2004 |
| WO | 2005003104 | A2 | 1/2005 |
| WO | 2005051350 | A2 | 6/2005 |
| WO | 2009063484 | | 5/2009 |
| WO | 2011107855 | A2 | 9/2011 |
| WO | 2011143721 | | 11/2011 |
| WO | 2019145507 | A1 | 8/2019 |
| WO | 2019186515 | A1 | 10/2019 |
| WO | 2022218437 | A1 | 10/2022 |
| WO | 2024201019 | A1 | 10/2024 |

OTHER PUBLICATIONS

Qian, Journal of Chemical Sciences (Bangalore, India) (2009), 121(4), 463-470.*
Galcera, CrystEngComm (2012), 14(23), 7898-7906.*
Galcera Crystal Growth & Design, vol. 9, No. 1, 2009, 327-334.*
Qian, J. Chem. Sci., vol. 121, No. 4, Jul. 2009, pp. 463-470.*
Kavanagh, International Journal of Pharmaceutics vol. 595, Feb. 15, 2021, 120274.*
Allen, Loyd V., Jr., Lamotrigine 1 mg/ml Oral Suspension, US Pharmacist, 2015, 40(5), 5 pages.
Beattie, K., et al., J. Profiles of Drug Substances, Excipients, and Related Methodology, 2012, vol. 37, pp. 245-285.
Lamictal Lamotrigine Tablet Label, 64 pages.
Lamictal Lamotrigine Tablet ODT prescribing information, Feb. 2023, 71 pages.
Lamotrigine Tablet for suspension, Alembic Pharmaceuticals Inc., Oct. 2021, 63 pages.
Nahata, Milap C., et al., Stability of lamotrigine in two extemporaneously prepared oral suspensions at 4 and 25 ° C., American Journal of Health-System Pharmacy, vol. 56, issue 3 (1), Feb. 1, 1999, abstract only.
Seager, Drug-delivery products and the zydis fast-dissolving dosage form, Journal of Pharmacy and Pharmacology, vol. 50, issue 4, Apr. 1998, abstract only.
Partial International Search Report issued by the International Searching Authority in connection with PCT/EP2025/077360 mailed Jan. 7, 2026, 21 pages.
Subvenite (lamotrigine oral suspension), package insert, Sep. 2025, 51 pages.

* cited by examiner $^1$H NMR spectroscopy data for Lamotrigine Hemifumarate Anhydrate in DMSO-$d_6$

| Apparent $^1$H chemical shift (δ, ppm) | Apparent multiplicity, coupling constant (J, Hz) | Integration | Assignment [17] |
|---|---|---|---|
| 7.68 | dd (J=7.7, 6.5) | 1H | H10, H12 |
| 7.34 | dd (J=7.5, 6.5) | 1H | |
| 7.41 | app t (J=8.0) | 1H | H11 |
| ~6.87* | bs | 2H* | H13, H14 |
| 6.63 | s | 2H | |
| 6.56 | s | 0.5·(2H) | H20, H21 |

*The values are estimated

Numbering of Lamotrigine Hemifumarate

LAMOTRIGINE SALTS, CO-CRYSTALS, AND COMPOSITIONS

CROSS REFERENCE TO RELATED APPLICATIONS

This application claims the benefit of priority of U.S. Provisional Application No. 63/698,821, filed Sep. 25, 2024, U.S. Provisional Application No. 63/756,940, filed Feb. 11, 2025, and U.S. Provisional Application No. 63/758,257, filed Feb. 13, 2025, each of which is incorporated by reference herein in its entirety for any purpose.

TECHNICAL FIELD

This disclosure provides novel lamotrigine salts, co-crystals, and compositions. In some embodiments, the lamotrigine salt is a lamotrigine dicarboxylic acid salt or hydrate or solvate thereof. In some embodiments, the lamotrigine co-crystal is a co-crystal of lamotrigine and a dicarboxylic acid, or a hydrate or solvate thereof. In some embodiments, the compositions comprise lamotrigine or a salt or co-crystal thereof, or a hydrate or solvate thereof. In some embodiments, the composition is in the form of a powder. In some embodiments, the composition is in the form of a liquid. The present disclosure also relates to methods of preparation and use in medical therapy, for example, for the treatment of a subject with epilepsy or bipolar disorder.

BACKGROUND

Lamotrigine is known as 6-(2,3-dichlorophenyl)-1,2,4-triazine-3,5-diamine or 3,5-diamino-6-(2,3-dichlorophenyl)-1,2,4-triazine. It is indicated for treatment of epilepsy and bipolar disorder. The molecular formula of lamotrigine is $C_9H_7N_5Cl_2$, and its molecular weight is 256.09 g/mol. Lamotrigine is depicted by the following chemical structure:

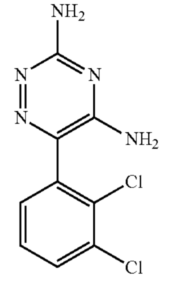 [SMILES: Nc1nnc(-c2cccc(Cl)c2Cl)c(N)n1]

Lamotrigine (free base) is marketed in the United States by GlaxoSmithKline LLC, under the trade name Lamictal®. Currently, there are several different types of immediate release Lamictal® products approved by US FDA: Lamictal tablets, Lamictal chewable dispersible tablets, Lamictal tablets for oral suspension, and Lamictal orally disintegrating tablets. According to the prescribing information, the tablets can be swallowed whole, chewed, or dispersed in water or juice. Also available are certain aqueous vehicles for mixing with lamotrigine tablets (e.g., Ora-Plus and Ora-Blend).

Importantly, there are no prepackaged, stable, ready-to-use liquid formulations of lamotrigine available for pediatric patients and patients who cannot swallow tablets. As a result, hospital pharmacists are often required to compound liquid formulations using crushed lamotrigine tablets that are then mixed with water or a vehicle. However, compounding formulations in a pharmacy setting in general is an imperfect art. For example, compounding formulations can have quality issues (e.g., the formulation may contain too much or too little of the active ingredient or can be contaminated with particulate matter and/or fungus). The FDA advises that compounded formulations are only to be used in patients whose medical needs cannot be met by an FDA-approved drug.

In addition to these general concerns, compounding lamotrigine tablets have specific problems. For example, lamotrigine is only very slightly soluble in water. Thus, when the crushed tablets of lamotrigine are added directly to water or other such liquids, the lamotrigine tends to settle rapidly and cannot be easily redistributed and as such, can potentially affect the dose accuracy delivered to a patient. In addition, lamotrigine is known to form a hydrate in an aqueous medium, which can also affect dose accuracy and compound stability. The formation of certain degradants (such as 2-(2,3-dichlorphenyl)-2-(guanidinylimino) acetonitrile, also known as Lamotrigine Impurity C) is another issue impacting drug safety. Further, lamotrigine has a very bitter taste in aqueous solutions, which may affect patient compliance.

Given these problems, there is no ready-to-use liquid formulation of Lamictal® available to patients. Further, even a vehicle such as Ora-Plus is unable to overcome such issues—for example, the resultant formulation contains a very low concentration of lamotrigine (i.e., 1 mg/mL).

Accordingly, an unmet need exists for different forms of lamotrigine and improved formulations that address the above-mentioned problems.

BRIEF SUMMARY OF THE DISCLOSURE

This disclosure provides lamotrigine salts, such as a lamotrigine hemifumarate anhydrate, lamotrigine co-crystals, and compositions comprising lamotrigine or a salt or co-crystal thereof, or a hydrate or solvate thereof.

Thus, in one aspect, the present disclosure relates to a lamotrigine salt selected from a lamotrigine dicarboxylic acid salt, and hydrates and solvates thereof. In some embodiments, the lamotrigine salt or hydrate or solvate thereof is in a crystalline form.

In another aspect, the present disclosure relates to a crystalline form of lamotrigine and a dicarboxylic acid, wherein the crystalline form is selected from a co-crystal of lamotrigine and the dicarboxylic acid, and hydrates and solvates thereof.

In another aspect, the present disclosure relates to a pharmaceutical composition comprising a lamotrigine salt or co-crystal, or hydrate or solvate thereof, and at least one pharmaceutically acceptable excipient.

In another aspect, the present disclosure relates to a kit comprising: (i) a first container comprising lamotrigine, a lamotrigine salt or a lamotrigine co-crystal, or hydrate or solvate thereof, or a pharmaceutical composition comprising lamotrigine, a lamotrigine salt or a lamotrigine co-crystal, or hydrate or solvate thereof, and a pharmaceutically acceptable excipient; and (ii) a second container comprising a vehicle.

In another aspect, the present disclosure relates to a pharmaceutical composition comprising lamotrigine or a salt or co-crystal thereof, or a hydrate or solvate thereof, wherein the composition is a liquid with a pH of from about 3.0 to about 5.0. In some embodiments, the composition has a pH of from about 3.5 to about 5.0, from about 3.6 to about 4.8, from about 3.6 to about 4.6, from about 3.6 to about 4.1, from about 3.6 to about 4.0, from about 3.6 to about 4.1, from about 4.0 to about 4.5, from about 4.0 to about 4.1, or from about 4.3 to about 5.0. In some embodiments, the composition has a pH of about 4.0. In some embodiments, the composition has a pH of about 4.6.

In another aspect, the present disclosure relates to a pharmaceutical composition comprising from about 5 mg/mL to about 50 mg/mL of lamotrigine or a salt or co-crystal thereof, or a hydrate or solvate thereof, wherein the composition is in the form of a liquid. In some embodiments, the liquid composition comprises about 5 mg/mL of lamotrigine or a salt or co-crystal thereof, or a hydrate or solvate thereof. In some embodiments, the liquid composition comprises about 25 mg/mL of lamotrigine or a salt or co-crystal thereof, or a hydrate or solvate thereof. In some embodiments, the liquid composition comprises about 50 mg/mL of lamotrigine or a salt or co-crystal thereof, or a hydrate or solvate thereof.

In some embodiments, the present disclosure relates to a pharmaceutical composition comprising an amount of lamotrigine or a salt or co-crystal thereof, or a hydrate or solvate thereof, that is equivalent to from about 5 mg/mL to about 50 mg/mL of lamotrigine (free base), wherein the composition is in the form of a liquid. In another aspect, the present disclosure relates to a pharmaceutical composition comprising an amount of lamotrigine or a salt or co-crystal thereof, or a hydrate or solvate thereof, that is equivalent to about 5 mg/mL of lamotrigine (free base), wherein the composition is in the form of a liquid. In another aspect, the present disclosure relates to a pharmaceutical composition comprising an amount of lamotrigine or a salt or co-crystal thereof, or a hydrate or solvate thereof, that is equivalent to about 25 mg/mL of lamotrigine (free base), wherein the composition is in the form of a liquid. In another aspect, the present disclosure relates to a pharmaceutical composition comprising an amount of lamotrigine or a salt or co-crystal thereof, or a hydrate or solvate thereof, that is equivalent to about 50 mg/mL of lamotrigine (free base), wherein the composition is in the form of a liquid.

In another aspect, the present disclosure relates to a pharmaceutical composition comprising lamotrigine or a salt or co-crystal thereof, or a hydrate or solvate thereof, wherein the composition is a liquid and the amount of lamotrigine or salt or co-crystal thereof, or a hydrate or solvate thereof, in the liquid is stable for about 6 months or more. In another aspect, the present disclosure relates to a pharmaceutical composition comprising lamotrigine or a salt or co-crystal thereof, or a hydrate or solvate thereof, wherein the composition is a liquid, and the composition is stable for about 6 months or more. In some embodiments, the composition is stable for about 24 months. In some embodiments, the composition is stable after being stored at about 5° C. for a period of time, at room temperature (about 25° C.) for a period of time, at about 40° C. for a period of time, or after being subjected to accelerated stability conditions for a period of time.

In another aspect, the present disclosure relates to a pharmaceutical composition comprising a salt or co-crystal of lamotrigine, wherein the composition is in the form of a liquid. In some embodiments, the composition is in the form of a suspension. In another aspect, the present disclosure relates to a pharmaceutical composition comprising lamotrigine and a salting agent, wherein the composition is in the form of a liquid. In some embodiments, the composition is in the form of a suspension.

In some embodiments, the present disclosure relates to a pharmaceutical composition comprising lamotrigine or a salt or co-crystal thereof, or a hydrate or solvate thereof, wherein the composition is palatable.

In some embodiments, the present disclosure relates to a pharmaceutical composition comprising lamotrigine or a salt or co-crystal thereof, or a hydrate or solvate thereof, wherein the composition is ready-to-use.

In some embodiments, the present disclosure relates to a pharmaceutical composition that is in the form of an oral dosage form.

In another aspect, the present disclosure relates to methods of preparing a lamotrigine salt or a lamotrigine co-crystal comprising combining lamotrigine (free base) with a salting agent, such as a carboxylic acid.

In another aspect, the present disclosure provides methods of treating a disease or condition selected from epilepsy, bipolar disorder, partial on-set seizures, primary generalized tonic-clonic seizures, generalized seizures of Lennox-Gastaut syndrome, acute mood episodes, acute manic episodes, and mixed mood episodes. In some embodiments, present disclosure provides methods of treating epilepsy comprising administering to a subject a lamotrigine salt, a lamotrigine co-crystal, or a composition as described herein. In some embodiments, present disclosure provides methods of treating bipolar comprising administering to a subject a lamotrigine salt, a lamotrigine co-crystal, or a composition as described herein.

DETAILED DESCRIPTION

Definitions

Figure 1:
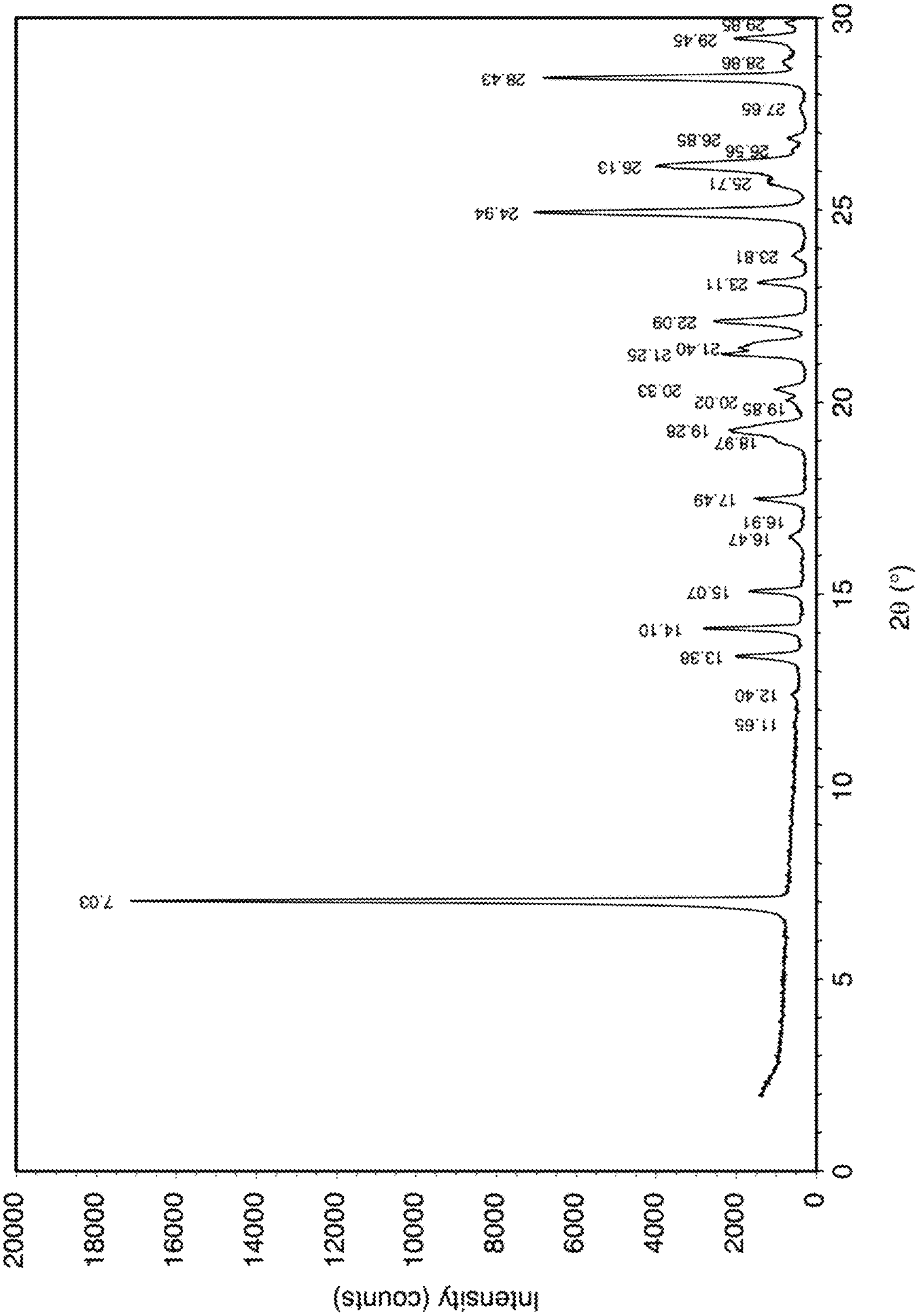
FIG. 1 shows an XRPD pattern of a lamotrigine hemifumarate anhydrate.

Unless otherwise defined, all terms of art, notations and other scientific terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a difference over what is generally understood in the art.

The techniques and procedures described or referenced herein are generally well understood and commonly employed using conventional methodologies by those skilled in the art. Standard techniques may be used for preparation and analysis of solid forms. As appropriate, procedures involving the use of commercially available kits and reagents are generally carried out in accordance with manufacturer-defined protocols and conditions unless otherwise noted.

While the following text may reference or exemplify specific embodiments, it is not intended to limit the scope of the disclosure.

The articles "a," "an," and "the" as used herein refer to "one or more" or "at least one," unless otherwise indicated. That is, reference to any element or component of an embodiment by the indefinite article "a" or "an" does not exclude the possibility that more than one element or component is present.

Unless otherwise described herein, the term "about" as used herein refers to the referenced numeric indication plus or minus 10% of that referenced numeric indication. In certain embodiments, where applicable, the term "about" indicates the designated value(s)±one standard deviation of that value(s). When the term "about" precedes a list of numerical values or ranges, the terms modify all of the values or ranges provided in the list. In some embodiments, the term "about" may include numerical values that are rounded to the nearest significant figure.

The term "active ingredient" or "active pharmaceutical ingredient" (API) refers to a compound (e.g., lamotrigine) that can be used for treating a disorder or condition in a subject (e.g., a patient), or for preventing one or more symptoms of such disorder or condition in the subject.

The term "comprising" also specifically includes embodiments "consisting of" and "consisting essentially of" the recited elements, unless specifically indicated otherwise.

The terms "composition," "pharmaceutical composition," and "formulation" are used interchangeably herein and refer to a combination of two or more ingredients. For example, a composition may comprise an active ingredient (e.g., lamotrigine) and a salting agent (e.g., fumaric acid).

The term "co-crystal" refers to a crystalline material made up of two or more different compounds. For example, a co-crystal may comprise lamotrigine and a salting agent (e.g., fumaric acid) where there has been no proton transfer (as in a traditional "salt"). In some embodiments, a co-crystal comprises lamotrigine, a salt agent (e.g., fumaric acid), and a lamotrigine salt (e.g., lamotrigine fumarate). The term "co-crystal" as used herein should be understood to encompass hydrates and solvates, whether or not explicitly stated.

The term "salt" refers to an ionic compound containing a cation and an anion. In some embodiments, a salt is formed when a base (e.g., lamotrigine) is combined with a salting agent (e.g., fumaric acid or disodium fumarate). The term "salt" as used herein should be understood to encompass hydrates and solvates, whether or not explicitly stated.

The term "bioequivalence" or "bioequivalent" refers to two compositions, dosage forms, or products of an active ingredient having biological equivalence. A formulation is generally considered to be bioequivalent to another if the 90% Confidence Interval ("CI") of the relative mean Cmax, AUC(0-t), and AUC(0-∞) of the test formulation to the reference formulation is within 80.0% to 125.0% in the fasting state of a tested subject.

The term "excipient" refers to any inactive substance in a composition (e.g., swelling agent, controlling-release agent, osmotic agent). An excipient may provide, without limitation, bulk, consistency, stability, binding ability, lubrication, disintegrating ability, etc., to the formulation of an active ingredient. An excipient may function for multiple purposes.

The terms "carrier" and "vehicle" are used interchangeably herein and refer to an excipient that delivers an active ingredient or composition. Carriers can help formulate an active ingredient or composition into a dosage form such as tablets, pills, dragees, capsules, liquids, gels, syrups, slurries, suspensions and the like, for administration to a subject in need. In some embodiments, the carrier can be water or an aqueous solution containing other excipients.

The term "diluent" refers to an excipient that dilutes a composition. Examples of diluents include sucrose, dextrose, mannitol, sorbitol, maltitol, starch, lactose, and microcrystalline cellulose.

The term "suspending agent" refers to an excipient that increases the viscosity of a formulation. Examples of suspending agents include hydrocolloid gums (such as xanthan gum, guar gum, locust bean gum, gum tragacanth, veegum, sodium alginate, carrageenan), cellulosic derivatives (such as sodium carboxymethylcellulose, hydroxypropyl cellulose, methyl cellulose, hydroxypropyl methylcellulose), polysaccharides (such as starch and pregelatinized starch), alginates (such as sodium alginate), acrylic acid copolymers (such as a carbopol), polyvinylpyrrolidone ("PVP"), and aluminum magnesium silicate.

The term "salting agent" refers to an excipient used to induce salt formation. Examples of salting agents include fumaric acid, hydrochloric acid, toluenesulfonic acid (TSA), and methanesulfonic acid (MSA). In some embodiments, the salting agent is disodium fumarate (also known as disodium fumaric acid), The term "buffering agent" refers to an excipient used to maintain the pH of a composition. Examples of buffering agents include salts of weak acids and bases as well as weak acids, such as citric acid. When a buffering agent is being used to maintain the pH of a composition, it is not a salting agent and vice versa.

The term "pH adjuster" refers to an excipient used to regulate the pH of a composition. Examples of pH adjusters include sodium hydroxide, hydrochloric acid, phosphoric acid, and disodium fumarate.

The term "preservative" refers to an excipient used to preserve the integrity of the composition. For example, in some embodiments, a preservative is used to slow down or stop degradation of the active ingredient or the other excipients in a composition and/or to prevent bacterial growth. Examples of preservatives include acids, alcohols, parabens, and phenols.

The term "sweetener" refers to an excipient used to improve the taste of pharmaceutical compositions. Examples of sweeteners include sucralose, glucose, sorbitol, aspartame, and saccharin sodium.

The term "antifoaming agent" refers to an excipient used to prevent or break up foam in pharmaceutical processes and products. Examples of antifoaming agents include insoluble oils (such as castor oil), polydimethylsiloxanes (such as simethicone) and other silicones, certain alcohols (such as cetostearyl alcohol), stearates, and glycols.

The term "anti-caking agent" refers to an excipient used to prevent aggregation of particles. Examples of anti-caking agents include silicon dioxide, magnesium silicate, and ammonium chloride.

The term "lubricants" refers to an excipient used to reduce friction, prevent sticking, and/or improve flowability. For example, lubricants can improve the flow of a powder by reducing frictional forces. Examples of lubricants include silicon dioxide, magnesium stearate, talc, and sodium stearyl fumarate.

The term "patient compliance" refers to the degree to which a patient correctly follows medical advice.

The term "powder" as used herein refers to a composition that is dry and flowable. Non-limiting examples include granules, flakes, spheroids, and other forms, which can be readily prepared and mixed with an ingestible liquid to provide a desirable liquid suspension.

The term "liquid," when used in the context of a composition, refers to a composition that is flowable but not dry. For example, a liquid composition may be a solution, a suspension, or an emulsion.

The term "stable" as used herein refers to the ability of a composition or substance to resist undergoing chemical reactions or decomposing under specified conditions. In general, a stable composition or compound is one that maintains its structure and properties without readily reacting with other substances in its environment. In some embodiments, a composition or compound disclosed herein is stable in that the lamotrigine or salt or co-crystal thereof, or a hydrate or solvate thereof, does not degrade, or degrades only slightly, when subjected to certain conditions (for example, the compound does not degrade, or degrades only slightly, to Lamotrigine Impurity C). Stability can be measured by, for example, UPLC.

In some embodiments, the stability of the composition or compound is measured after being stored at about 5° C. for a period of time. In some embodiments, the stability of the composition or compound is measured after being stored at room temperature (about 25° C.) for a period of time. In some embodiments, the stability of the composition or compound is measured after being stored at about 40° C. for a period of time. In some embodiments, the period of time is less than about 1 month. In some embodiments, the period of time is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, or more. In some embodiments, the period of time is at least about 24 months. In some embodiments, the period of time is about 1 month, about 2 months, about 3 months, about 4 months, about 5 months, about 6 months, about 7 months, about 8 months, about 9 months, about 10 months, about 11 months, about 12 months, or more. In some embodiments, the period of time is about 6 months. In some embodiments, the period of time is about 24 months.

In some embodiments, the stability of the composition or compound disclosed herein is measured after being subjected to accelerated stability conditions. In some embodiments, the accelerated stability conditions are about 40° C. and about 75% relative humidity (RH) for a period of time. In some embodiments, the accelerated stability conditions are about 60° C. at room temperature for a period of time. In some embodiments, the period of time is less than about 1 month. In some embodiments, the period of time is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, or more. In some embodiments, the period of time is at least about 24 months. In some embodiments, the period of time is about 1 month, about 2 months, about 3 months, about 4 months, about 5 months, about 6 months, about 7 months, about 8 months, about 9 months, about 10 months, about 11 months, about 12 months, or more. In some embodiments, the period of time is about 6 months. In some embodiments, the period of time is about 24 months.

The terms "release", "released", "releasing", and the like, when used in connection with a pharmaceutical composition or dosage form, refer to the process or the portion of the active ingredient that leaves the composition or dosage form. Unless otherwise indicated, the quantity of an active ingredient released from a dosage form is measured by dissolution testing in water. The results of the dissolution testing may be reported as % (w/w) released as a function of time or as the release time. In some embodiments, "complete release" of an active ingredient occurs when at least 90% of the active ingredient has been released from the dosage form.

The term "immediate release" refers a pharmaceutical composition or dosage form which disintegrates and/or dissolves rapidly to release the active ingredient. The term "extended release" refers to a pharmaceutical composition or dosage form which disintegrates and/or dissolves gradually over time, allowing the active ingredient to be released over a longer period of time compared to an immediate release composition or dosage form. Extended release compositions and dosage forms encompass both sustained release and controlled release compositions and dosage forms.

The term "Cmax" or "peak plasma exposure", expressed in ng/ml, refers to the point of maximum concentration of drug in plasma.

The term "area under curve (AUC)" or "total plasma exposure", expressed in μg·hr/mL, refers to the total integrated area under plasma level time profile and expresses the total amount of the active ingredient that comes into systemic circulation after administration.

The term "D90" refers to the particle size corresponding to 90% of the cumulative undersize distribution by volume.

The term "sedimentation volume ratio" or "sedimentation ratio" refers to a ratio of the ultimate volume of sediment (Vu) to the original volume of sediment (VO) before settling.

The term "subject" refers to a mammal, such as an animal or a human. Hence, the methods of treatment disclosed herein can be useful in human therapy and veterinary applications. In one embodiment, the subject is an animal. In another embodiment, the subject is a human.

The term "XRPD" is the analytical technique of X-ray powder diffraction. A typical XRPD pattern is an x-y graph with 2θ (diffraction angle) plotted on the x-axis and intensity plotted on the y-axis. These are the diffraction peaks which may be used to characterize a crystalline material. The diffraction peaks are usually represented and referred to by their position on the x-axis rather than the intensity of the diffraction peaks on the y-axis because diffraction peak intensity can be particularly sensitive to sample orientation (see Pharmaceutical Analysis, Lee & Web, pp. 255-257 (2003)). Thus, intensity (sometimes referred to as "height") is not typically used by those of skill in the art to characterize a crystalline material. As with any data measurement, there may be variability in XRPD data. In addition to the variability in diffraction peak intensity, there may also be variability in the position of the diffraction peaks on the x-axis. This variability can, however, typically be accounted for when reporting the positions of diffraction peaks for purposes of characterization. Such variability in the position of diffraction peaks along the x-axis may be derived from several sources. One such source can be sample preparation. Samples of the same crystalline material prepared under different conditions may yield slightly different diffractograms. Factors such as particle size, moisture content, solvent content, temperature, and orientation may all affect how a sample diffracts X-rays. Another source of variability comes from instrument parameters. Different X-ray powder diffractometers operate using different parameters and may lead to slightly different diffraction patterns from the same crystalline material. Likewise, different software packages process XRPD data differently and this may also lead to variability. These and other sources of variability are known to those of ordinary skill in the art. Due to such sources of variability, the values of each X-ray diffraction peak are typically preceded with the term "about" or proceeded with an appropriate range defining the experimental variability. For purposes of data reported herein, that value is ±0.2° 2θ unless otherwise stated. This means that on a well-maintained instrument one would expect the variability in peak measurement to be ±0.2° 2θ. X-ray powder diffraction peaks cited herein are generally reported with this variability of ±0.2° 2θ unless stated otherwise and are intended to be reported with such a variability whenever disclosed herein whether the word "about" is present or not, unless context dictates otherwise.

Solid forms, such as those disclosed herein, are readily analyzed by XRPD. The data from X-ray powder diffraction may be used in multiple ways to characterize solid forms. For example, the entire X-ray powder diffraction pattern output from a diffractometer may be used to characterize a solid form. A smaller subset of such data, however, may also be suitable and used for characterizing such solid forms. Indeed, often even a single X-ray powder diffraction peak may be used to characterize a crystalline form.

As used herein, the term "one or more peaks" means that any combination of the peaks listed may be present in the corresponding analytical measurement, such as an XRPD pattern. It does not mean (in and of itself) that no other peak may be present in the corresponding analytical measurement, such as an XRPD pattern.

The term "$^1$H NMR" is the analytical technique of proton ($^1$H) nuclear magnetic resonance spectroscopy, and is further described herein (vide infra).

The term "TGA" is the analytical technique of thermogravimetric analysis, and is further described herein (vide infra).

The term "DSC" is the analytical technique of differential scanning calorimetry, and is further described herein (vide infra).

The term "FT-IR" refers to Fourier transform infrared spectroscopy, and is further described herein (vide infra).

The term "substantially the same as" refers to results that are, within the experimental variability of the measurements, considered to be equivalent. For example, an XRPD pattern that is substantially the same as another XRPD pattern means the patterns represent the same form of the material as is well understood by one skilled in the art when taking into account, for example, variability associated among samples and instruments, and experimental conditions.

The terms "treat," "treating," and the like refer to attaining a beneficial or desired result, such as a clinical result. In some embodiments, the beneficial or desired result is any one or more of the following: inhibiting or suppressing the onset or development of a condition, reducing the severity of the condition, reducing the number or severity of symptoms associated with the condition, increasing the quality of life of a patient suffering from the condition, decreasing the dose of another medication required to treat the condition, enhancing the effect of another medication a patient is taking for the condition, and prolonging the survival of a patient having the condition.

The term "wet granulation" refers to a process of using a liquid binder to lightly agglomerate the powder mixture.

The terms "include," "such as," and the like are intended to convey inclusion without limitation, unless otherwise specifically indicated.

At various places in the present disclosure, variables or parameters are disclosed in groups or ranges. It is specifically intended that the description include each and every individual subcombination of the members of such groups and ranges. For example, an integer in the range of 0 to 10 is specifically intended to individually disclose 0, 1, 2, 3, 4, 5, 6, 7, 8, 9, and 10.

Lamotrigine Salts, Co-crystals, Compositions, Kits, and Methods

In one aspect, the present disclosure relates to lamotrigine salts, co-crystals, and hydrates and solvates thereof.

In some embodiments, the salt of lamotrigine is chosen from, for example, a fumarate salt, a hydrochloric acid salt, toluenesulfonic acid (TSA) salt, and methanesulfonic acid (MSA) salt. In some embodiments, the co-crystal of lamotrigine comprises lamotrigine and a salting agent, such as fumaric acid, hydrochloric acid, toluenesulfonic acid (TSA), and methanesulfonic acid (MSA).

In one aspect, the present disclosure relates to a lamotrigine salt selected from a lamotrigine dicarboxylic acid salt and hydrates and solvates thereof. In one aspect, the present disclosure relates to a crystalline form of a lamotrigine salt selected from a lamotrigine dicarboxylic acid salt and hydrates and solvates thereof.

In some embodiments, the lamotrigine salt or hydrate or solvate thereof is selected from a lamotrigine monofumarate, a lamotrigine hemifumarate, a lamotrigine difumarate, and hydrates and solvates thereof. In some embodiments, the lamotrigine salt or hydrate or solvate thereof is selected from a lamotrigine hemifumarate anhydrate, a lamotrigine hemifumarate solvate, and a lamotrigine hemifumarate hydrate.

In some embodiments, the lamotrigine salt is a lamotrigine hemifumarate anhydrate. As used herein, a "lamotrigine hemifumarate" refers to a salt with a stoichiometry that is less than 1:1 fumarate/lamotrigine.

In some embodiments, the stoichiometry of the lamotrigine hemifumarate anhydrate is in a range from about 0.50:1 fumarate/lamotrigine to about 0.99:1 fumarate/lamotrigine. In some embodiments, the stoichiometry of the lamotrigine hemifumarate anhydrate is in a range from about 0.50:1 fumarate/lamotrigine to about 0.80:1 fumarate/lamotrigine. In some embodiments, the stoichiometry of the lamotrigine hemifumarate anhydrate is in a range from about 0.50:1 fumarate/lamotrigine to about 0.70:1 fumarate/lamotrigine. In some embodiments, the stoichiometry of the lamotrigine hemifumarate anhydrate is in a range from about 0.50:1 fumarate/lamotrigine to about 0.60:1 fumarate/lamotrigine.

In some embodiments, the stoichiometry of the lamotrigine hemifumarate anhydrate is about 0.50:1 fumarate/lamotrigine. In some embodiments, the stoichiometry of the lamotrigine hemifumarate anhydrate is about 0.51:1 fumarate/lamotrigine. In some embodiments, the stoichiometry of the lamotrigine hemifumarate anhydrate is about 0.52:1 fumarate/lamotrigine. In some embodiments, the stoichiometry of the lamotrigine hemifumarate anhydrate is about 0.53:1 fumarate/lamotrigine. In some embodiments, the stoichiometry of the lamotrigine hemifumarate anhydrate is about 0.54:1 fumarate/lamotrigine. In some embodiments, the stoichiometry of the lamotrigine hemifumarate anhydrate is about 0.55:1 fumarate/lamotrigine. In some embodiments, the stoichiometry of the lamotrigine hemifumarate anhydrate is about 0.56:1 fumarate/lamotrigine. In some embodiments, the stoichiometry of the lamotrigine hemifumarate anhydrate is about 0.57:1 fumarate/lamotrigine. In some embodiments, the stoichiometry of the lamotrigine hemifumarate anhydrate is about 0.58:1 fumarate/lamotrigine. In some embodiments, the stoichiometry of the lamotrigine hemifumarate anhydrate is about 0.59:1 fumarate/lamotrigine. In some embodiments, the stoichiometry of the lamotrigine hemifumarate anhydrate is about 0.6:1 fumarate/lamotrigine.

In some embodiments, the lamotrigine hemifumarate anhydrate has an x-ray powder diffraction (XRPD) pattern comprising one or more peaks at about 7.0° 2θ, about 13.4° 2θ, about 14.1° 2θ, about 15.1° 2θ, about 17.5° 2θ, about 22.1° 2θ, and about 24.9° 2θ. In some embodiments, the lamotrigine hemifumarate anhydrate has an XRPD pattern comprising two or more peaks at about 7.0° 2θ, about 13.4° 2θ, about 14.1° 2θ, about 15.1° 2θ, about 17.5° 2θ, about 22.1° 2θ, and about 24.9° 2θ. In some embodiments, the lamotrigine hemifumarate anhydrate has an XRPD pattern comprising three or more peaks at about 7.0° 2θ, about 13.4° 2θ, about 14.1° 2θ, about 15.1° 2θ, about 17.5° 2θ, about 22.1° 2θ, and about 24.9° 2θ. In some embodiments, the lamotrigine hemifumarate anhydrate has an XRPD pattern comprising four or more peaks at about 7.0° 2θ, about 13.4° 2θ, about 14.1° 2θ, about 15.1° 2θ, about 17.5° 2θ, about 22.1° 2θ, and about 24.9° 2θ. In some embodiments, the lamotrigine hemifumarate anhydrate has an XRPD pattern comprising five or more peaks at about 7.0° 2θ, about 13.4° 2θ, about 14.1° 2θ, about 15.1° 2θ, about 17.5° 2θ, about 22.1° 2θ, and about 24.9° 2θ.

In some embodiments, the lamotrigine hemifumarate anhydrate has an x-ray powder diffraction (XRPD) pattern comprising two or more peaks, or three or more peaks, or four or more peaks, or five or more peaks, at about 7.0° 2θ, about 11.7° 2θ, about 12.4° 2θ, about 13.4° 2θ, about 14.1° 2θ, about 15.1° 2θ, about 16.5° 2θ, about 16.9° 2θ, about 17.5° 2θ, about 19.0° 2θ, about 19.3° 2θ, about 19.9° 2θ, about 20.0° 2θ, about 20.3° 2θ, about 21.3° 2θ, about 21.4° 2θ, about 22.1° 2θ, about 23.1° 2θ, about 23.8° 2θ, about 24.9° 2θ, about 25.7° 2θ, about 26.1° 2θ, about 26.6° 2θ, about 26.9° 2θ, about 27.7° 2θ, about 28.4° 2θ, about 28.9° 2θ, about 29.5° 2θ, and about 29.9° 2θ.

In some embodiments, the lamotrigine hemifumarate anhydrate has an XRPD pattern substantially the same as in FIG. 1.

In some embodiments, the lamotrigine hemifumarate anhydrate is characterized by a differential scanning calorimetry (DSC) thermogram with an endothermic peak at about 273° C. In some embodiments, the lamotrigine hemifumarate anhydrate which has a melt onset near 272° C. as measured by DSC. In some embodiments, the lamotrigine hemifumarate anhydrate has a DSC thermogram substantially the same as in FIG. 7. In some embodiments, the DSC is measured in a sealed aluminum pan with a pierced lid.

Figure 3:
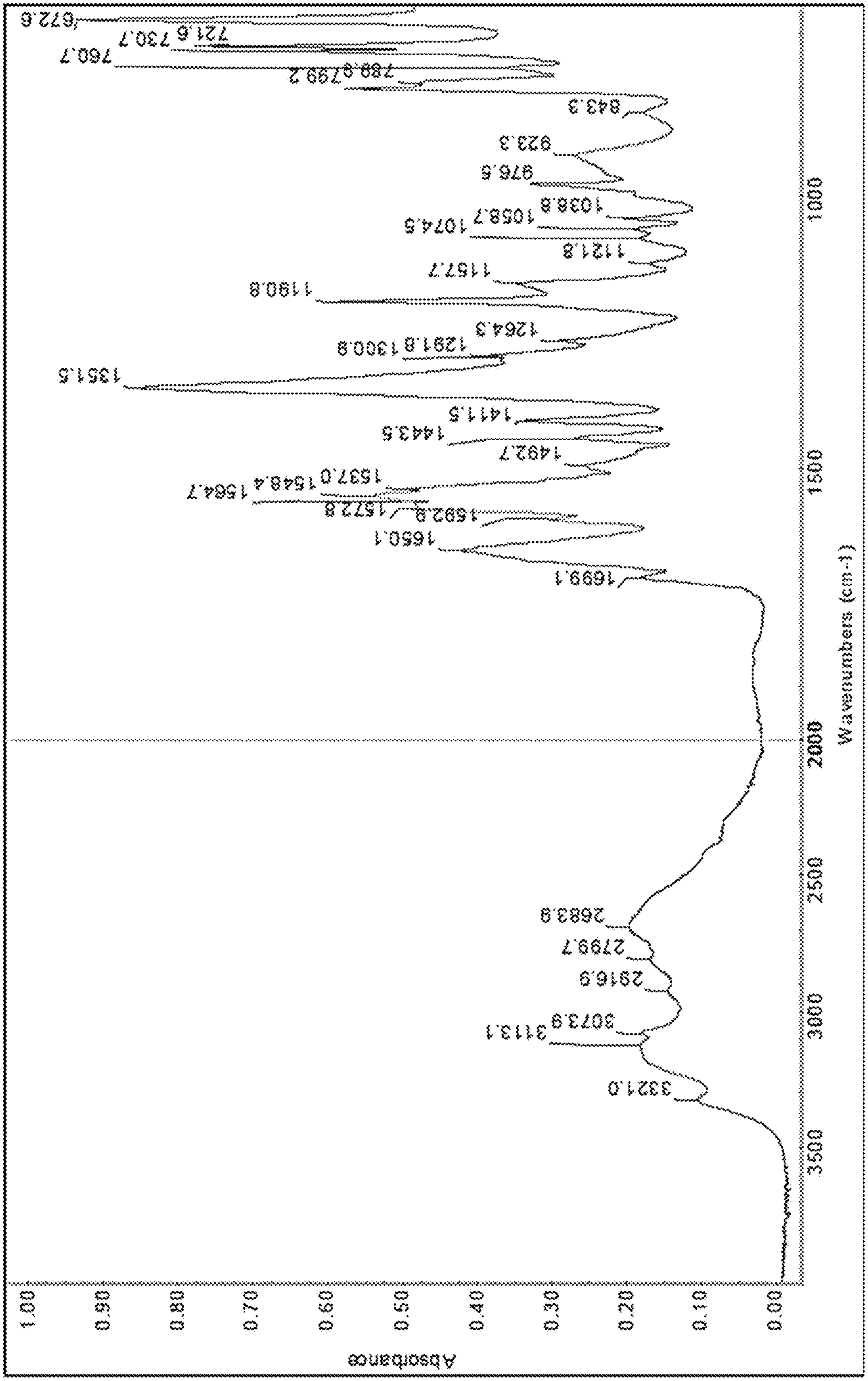
FIG. 3 shows an FT-IR spectrum of a lamotrigine hemifumarate anhydrate.

In some embodiments, the lamotrigine hemifumarate anhydrate has a Fourier-transform infrared spectroscopy spectrum substantially the same as in FIG. 3.

In some embodiments, the lamotrigine hemifumarate anhydrate has an x-ray powder diffraction (XRPD) pattern comprising one or more peaks at about 7.0° 2θ, about 13.4° 2θ, about 14.1° 2θ, about 15.1° 2θ, about 17.5° 2θ, about 22.1° 2θ, and about 24.9° 2θ; is characterized by a differential scanning calorimetry (DSC) thermogram with an endothermic peak at about 273° C.; and/or has a melt onset near 272° C. as measured by DSC.

In another aspect, the present disclosure relates to lamotrigine co-crystals and hydrates and solvates thereof. In some embodiments, the co-crystal comprises lamotrigine and a salting agent (such as, for example, fumaric acid, hydrochloric acid, TSA, MSA, and disodium fumarate). In some embodiments, the present disclosure relates to a crystalline form of lamotrigine and a dicarboxylic acid, wherein the crystalline form is selected from a co-crystal of lamotrigine and the dicarboxylic acid, and hydrates and solvates thereof. In some embodiments, the dicarboxylic acid is fumaric acid.

In some embodiments, the lamotrigine salt or co-crystal, or a hydrate or solvate thereof, has a D90 of less than about 200 μm, less than about 150 μm, less than about 120 μm, less than about 100 μm, less than about 80 μm, less than about 60 μm, less than about 40 μm. In some embodiments, the D90 ranges from about 5 μm to about 150 μm, from about 10 μm to about 120 μm, from about 20 μm to about 100 μm, or from about 30 μm to about 90 μm. In some embodiments, the D90 ranges from about 25 μm to about 75 μm, from about 30 μm to about 50 μm, or from about 40 μm to about 50 μm.

In some embodiments, the lamotrigine salt or co-crystal, or a hydrate or solvate thereof, exhibits greater solubility in an aqueous solvent or solvents as compared to lamotrigine (free base). In some embodiments, the solubility is measured by methods in the United States Pharmacopeia (USP). In some embodiments, the aqueous solvent comprises water.

In some embodiments, the lamotrigine salt or co-crystal, or a hydrate or solvate thereof, has an increased blood concentration when administered to a subject as compared to lamotrigine (free base) when administered to a subject.

In some embodiments, the lamotrigine salt or co-crystal, or a hydrate or solvate thereof, exhibits an improved absorption and pharmacokinetic (PK) profile when administered to a subject as compared to lamotrigine (free base) when administered to a subject.

In some embodiments, the lamotrigine salt or co-crystal, or a hydrate or solvate thereof, exhibits an increased rate of dissolution as compared to lamotrigine (free base). In some embodiments, the dissolution is measured by methods in the United States Pharmacopeia (USP). In some embodiments, the dissolution is measured in water, FaSSGF, FaSSIF, or FeSSIF. In some embodiments, the dissolution is measured in water.

In some embodiments, the lamotrigine salt or co-crystal, or a hydrate or solvate thereof, exhibits a sustained release profile as compared to lamotrigine (free base) when administered to a subject. In some embodiments, the release profile is measured by methods in the United States Pharmacopcia (USP), such as the USP dissolution apparatus 2 in 900 mL of pH 6.8 at 50 RPM.

In some embodiments, the lamotrigine salt or co-crystal, or a hydrate or solvate thereof, is more stable in aqueous solutions than lamotrigine (free base). In some embodiments, the lamotrigine salt or co-crystal, or a hydrate or solvate thereof, is more stable in aqueous solutions than lamotrigine (free base) in that less Lamotrigine Impurity C is formed in solution. In some embodiments, the lamotrigine salt or co-crystal, or a hydrate or solvate thereof, is more stable in aqueous solutions than lamotrigine (free base) in that the lamotrigine does not become hydrated.

In some embodiments, the stability of the aqueous solutions comprising lamotrigine salt or co-crystal, or a hydrate or solvate thereof, is measured after being stored at about 5° C. for a period of time. In some embodiments, the stability of the aqueous solutions comprising lamotrigine salt or co-crystal, or a hydrate or solvate thereof, is measured after being stored at room temperature (about 25° C.) for a period of time. In some embodiments, the stability of the aqueous solutions comprising lamotrigine salt or co-crystal, or a hydrate or solvate thereof, is measured after being stored at about 40° C. for a period of time. In some embodiments, the period of time is less than about 1 month. In some embodiments, the period of time is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, or more. In some embodiments, the period of time is at least about 24 months. In some embodiments, the period of time is about 1 month, about 2 months, about 3 months, about 4 months, about 5 months, about 6 months, about 7 months, about 8 months, about 9 months, about 10 months, about 11 months, about 12 months, or more. In some embodiments, the period of time is about 6 months. In some embodiments, the period of time is about 24 months.

In some embodiments, the stability of the aqueous solutions comprising lamotrigine salt or co-crystal, or a hydrate or solvate thereof, is measured after being subjected to accelerated stability conditions. In some embodiments, the accelerated stability conditions are about 40° C. and about 75% relative humidity (RH) for a period of time. In some embodiments, the accelerated stability conditions are about 60° C. at room temperature for a period of time. In some embodiments, the period of time is less than about 1 month. In some embodiments, the period of time is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, or more. In some embodiments, the period of time is at least about 24 months. In some embodiments, the period of time is about 1 month, about 2 months, about 3 months, about 4 months, about 5 months, about 6 months, about 7 months, about 8 months, about 9 months, about 10 months, about 11 months, about 12 months, or more. In some embodiments, the period of time is about 6 months. In some embodiments, the period of time is about 24 months.

Stability can be measured by, for example, UPLC.

In another aspect, the present disclosure relates to methods of preparing a lamotrigine salt or co-crystal, or a hydrate or solvate thereof, comprising combining lamotrigine (free base) with a carboxylic acid. In some embodiments, the carboxylic acid is a dicarboxylic acid. In some embodiments, the carboxylic acid is fumaric acid.

In some embodiments, the lamotrigine is combined with the carboxylic acid in an aqueous solution. In some embodiments, the aqueous solution is water. In some embodiments, after the addition of the lamotrigine and the carboxylic acid, the pH of the aqueous solution is adjusted to a pH in a range from about 2 to about 7, from about 3 to about 6, or from about 4 to about 5. In some embodiments, the pH of the aqueous solution is adjusted to a pH of about 4.

In one aspect, the present disclosure relates to a pharmaceutical composition comprising a lamotrigine salt or co-crystal, or hydrate or solvate thereof, and at least one pharmaceutically acceptable excipient. In some embodiments, the composition is a solid. In some embodiments, the composition is in the form of a powder. In some embodiments, the composition is in the form of a liquid, such as a suspension.

In some embodiments, the solid composition (such as a powder composition) is suitable for reconstitution in a pharmaceutically acceptable carrier. In some embodiments, the reconstituted composition is a suspension. In some embodiments, a suspension is achieved within about 60 seconds after the composition is reconstituted with water. In some embodiments, the suspension is homogeneous.

In some embodiments, when present in a composition, the lamotrigine salt or co-crystal, or a hydrate or solvate thereof, tastes less bitter than lamotrigine (free base). Without being bound by theory, it is theorized that the taste "masking" by the salt or co-crystal is related to the amount of "free fraction" lamotrigine (i.e., the amount of solubilized lamotrigine) in the composition.

In some embodiments, in a liquid composition comprising a lamotrigine salt or co-crystal, or hydrate or solvate thereof, the amount of solubilized lamotrigine (free base) is less than about 1.00%. In some embodiments, the amount of solubilized lamotrigine is from about 0.01% to about 1.00%. In some embodiments, the amount of solubilized lamotrigine is from about 0.01% to about 0.90%, from about 0.01% to about 0.80%, from about 0.01 to about 0.70%, from about 0.01% to about 0.60%, from about 0.01% to about 0.50%, from about 0.01% to about 0.40%, from about 0.01% to about 0.30%, from about 0.01% to about 0.20%, or from about 0.01% to about 0.10%.

In some embodiments, when the composition is in the form of a liquid, the composition is stable after being stored at about 5° C. for a period of time. In some embodiments, the composition is stable after being stored at room temperature (about 25° C.) for a period of time. In some embodiments, the composition is stable after being stored at about 40° C. for a period of time. In some embodiments, the period of time is less than about 1 month. In some embodiments, the period of time is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, or more. In some embodiments, the period of time is at least about 24 months. In some embodiments, the period of time is about 1 month, about 2 months, about 3 months, about 4 months, about 5 months, about 6 months, about 7 months, about 8 months, about 9 months, about 10 months, about 11 months, about 12 months, or more. In some embodiments, the period of time is about 6 months. In some embodiments, the period of time is about 24 months.

In some embodiments, the composition is stable after being subjected to accelerated stability conditions. In some embodiments, the accelerated stability conditions are about 40° C. and about 75% relative humidity (RH) for a period of time. In some embodiments, the accelerated stability conditions are about 60° C. at room temperature for a period of time. In some embodiments, the period of time is less than about 1 month. In some embodiments, the period of time is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, or more. In some embodiments, the period of time is at least about 24 months. In some embodiments, the period of time is about 1 month, about 2 months, about 3 months, about 4 months, about 5 months, about 6 months, about 7 months, about 8 months, about 9 months, about 10 months, about 11 months, about 12 months, or more. In some embodiments, the period of time is about 6 months. In some embodiments, the period of time is about 24 months.

In some embodiments, when the composition is a suspension, the suspension may be stable for at least 3 months. In some embodiments, the suspension is stable for at least 4 months, at least 5 months, at least 6 months, at least 7 months, at least 8 months, or at least 9 months. In some embodiments, the suspension is stable for at least 12 months. In some embodiments, the suspension is stable for at least 24 months. In some embodiments, the suspension is stable after being stored at about 5° C. for a period of time, at room temperature (about 25° C.) for a period of time, at about 40° C. for a period of time, or after being subjected to accelerated stability conditions for a period of time. Stability can be measured by, for example, UPLC.

In some embodiments, the suspension maintains a sedimentation volume ratio of more than about 0.7, more than about 0.8, or more than about 0.9 for a period of at least about 10 hours, at least about 12 hours, at least about 15 hours, at least about 18 hours, at least about 20 hours, at least about 24 hours, at least about 30 hours, or at least about 48 hours after the composition is reconstituted.

In some embodiments, the sedimentation volume ratio is achieved within about 5 minutes, about 3 minutes, about 2 minutes, about 60 seconds, about 45 seconds, or about 30 seconds after the composition is reconstituted to a suspension. Various mechanical means, such as shaking, swirling, heating, or any combination thereof can be used to promote a uniform suspension.

In some embodiments, less than about 8%, less than about 5%, less than about 3%, less than about 1%, or less than about 0.5% of the lamotrigine or its salt or co-crystal is converted into its hydrate form within about 5 hours, within about 10 hours, within about 12 hours, within about 15 hours, within about 20 hours, within about 24 hours, within about 30 hours, or within about 48 hours after the composition is reconstituted into a suspension. In some embodiments, less than about 5% of lamotrigine or its salt or co-crystal exists in its hydrate form within about 24 hours after the composition is reconstituted into a suspension. The amount of hydration can be measured by, for example, UPLC.

In some embodiments, less than about 5%, less than about 3%, less than about 1%, less than about 0.5%, less than about 0.2%, or less than about 0.1% of the lamotrigine or its salt or co-crystal is decomposed (for example, into Lamotrigine Impurity C) in about 10 hours, in about 20 hours, in about 24 hours, in about 2 days, in about 3 days, or in about 1 week after the composition is reconstituted into a suspension. In some embodiments, less than about 0.5% of lamotrigine or its salt or co-crystal decomposes within about 24 hours after the composition is reconstituted into the suspension.

In some embodiments, less than about 5%, less than about 3%, less than about 1%, less than about 0.5%, less than about 0.2%, or less than about 0.1% of the lamotrigine or its salt or co-crystal is decomposed (for example, into Lamotrigine Impurity C) after being stored at about 5° C. for a period of time, at room temperature (about 25° C.) for a period of time, at about 40° C. for a period of time, or under accelerated stability conditions for a period of time. In some embodiments, the period of time is less than about 1 month. In some embodiments, the period of time is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, or more. In some embodiments, the period of time is at least about 24 months. In some embodiments, the period of time is about 1 month, about 2 months, about 3 months, about 4 months, about 5 months, about 6 months, about 7 months, about 8 months, about 9 months, about 10 months, about 11 months, about 12 months, or more. In some embodiments, the period of time is about 6 months. In some embodiments, the period of time is about 24 months. Decomposition can be measured by, for example, UPLC.

In some embodiments, the suspension provides an in vitro release of at least about 95%, at least about 90%, at least about 85%, at least about 80%, at least about 70%, or at least about 60% of lamotrigine in a medium of pH of 1 after 5 minutes. In some embodiments, the suspension provides an in vitro release of at least about 85% of lamotrigine (free base) in a pH 1 medium after 5 minutes. In some embodiments, the release is measured by a method in the United States Pharmacopeia (USP), for example using a USP dissolution apparatus 1 or USP dissolution apparatus 2. In some embodiments, the release is measured using a USP dissolution apparatus 2 in 900 mL of pH 6.8 at 50 RPM.

In some embodiments, the suspension provides a release of lamotrigine that is bioequivalent to non-suspension formulation of lamotrigine at the same dose. Examples of non-suspension formulations of lamotrigine include Lamictal® tablets, Lamictal® chewable dispersible tablets, and Lamictal® orally disintegrating tablets.

In some embodiments, in the compositions disclosed herein, the at least one pharmaceutically acceptable excipient is selected from surface active agents, sweeteners, lubricants, glidants, diluents, smoothing agents, suspension agents, film forming substances, buffering agents, coating assistants, and any combination thereof. In some embodiments, the at least one pharmaceutically acceptable excipient is selected from a salting agent, a pH adjuster, a suspending agent, a preservative, a sweetener, an antifoaming agent, an anti-caking agent, and any combination thereof.

In some embodiments, the at least one pharmaceutically acceptable excipient is a salting agent. In some embodiments, the salting agent is present in an amount ranging from about 0.10% w/w to about 10.00% w/w based on the total weight of the composition. In some embodiments, the salting agent is present in an amount ranging from about 0.10% w/w to about 5.00% w/w based on the total weight of the composition. In some embodiments, the salting agent is present in an amount ranging from about 0.10% w/w to about 1.00% w/w based on the total weight of the composition. In some embodiments, the salting agent is present in an amount ranging from about 0.10% w/w to about 0.75% w/w based on the total weight of the composition. In some embodiments, the salting agent is present in an amount ranging from about 0.10% w/w to about 0.70% w/w based on the total weight of the composition. In some embodiments, the salting agent is present in an amount of about 0.10% w/w based on the total weight of the composition. In some embodiments, the salting agent is present in an amount of about 0.70% w/w based on the total weight of the composition. In some embodiments, the salting agent is chosen from fumaric acid, disodium fumarate, hydrochloric acid, toluenesulfonic acid (TSA), and methanesulfonic acid (MSA). In some embodiments, the salting agent is fumaric acid or disodium fumarate.

In some embodiments, the at least one pharmaceutically acceptable excipient is a pH adjuster. In some embodiments, the pH adjuster is present in an amount ranging from about 0.001% w/w to about 0.050% w/w based on the total weight of the composition. In some embodiments, the pH adjuster is present in an amount ranging from about 0.001% w/w to about 0.020% w/w based on the total weight of the composition. In some embodiments, the pH adjuster is present in an amount ranging from about 0.001% w/w to about 0.100% w/w based on the total weight of the composition. In some embodiments, the pH adjuster is present in an amount ranging from about 0.004% w/w to about 0.050% w/w based on the total weight of the composition. In In some embodiments, the pH adjuster is present in an amount ranging from about 0.004% w/w to about 0.020% w/w based on the total weight of the composition. In some embodiments, the pH adjuster is present in an amount ranging from about 0.004% w/w to about 0.100% w/w based on the total weight of the composition. In some embodiments, the pH adjuster is selected from sodium hydroxide, hydrochloric acid, phosphoric acid, disodium fumarate, and any combination thereof. In some embodiments, the pH adjuster is selected from sodium hydroxide, hydrochloric acid, and any combination thereof.

In some embodiments, the at least one pharmaceutically acceptable excipient is a suspending agent. In some embodiments, the suspending agent is present in an amount ranging from about 0.10% w/w to about 10.00% w/w based on the total weight of the composition. In some embodiments, the suspending agent is present in an amount ranging from about 0.10% w/w to about 5.00% w/w based on the total weight of the composition. In some embodiments, the suspending agent is present in an amount ranging from about 0.10% w/w to about 2.00% w/w based on the total weight of the composition. In some embodiments, the suspending agent is present in an amount ranging from about 0.10% w/w to about 0.50% w/w based on the total weight of the composition. In some embodiments, the suspending agent is present in an amount ranging from about 0.10% w/w to about 0.15% w/w based on the total weight of the composition. In some embodiments, the suspending agent is present in an amount of about 0.10% w/w based on the total weight of the composition. In some embodiments, the suspending agent is present in an amount of about 0.15% w/w based on the total weight of the composition.

In some embodiments, when the composition is in the form of a suspension, the suspending agent reduces the formation of lamotrigine hydrate in the suspension, as compared to an equivalent dose of the lamotrigine (free base) in an equivalent suspension but without the suspending agent.

In some embodiments, the ratio between the lamotrigine salt or co-crystal, or hydrate or solvate thereof, and the suspending agent is in a range from about 20:1 to about 1:5 by weight. In some embodiments, the ratio ranges from about 15:1 to about 1:5, from about 10:1 to about 1:5, from about 5:1 to about 1:5, from about 10:1 to about 2:1, from about 10:1 to about 1:1, from about 8:1 to about 4:1, from about 6:1 to about 3:1, or from about 6:1 to about 4:1. In some embodiments, the ratio is about 5:1 by weight.

In some embodiments, the suspending agent is selected from a hydrocolloid gum (such as xanthan gum, guar gum, locust bean gum, gum tragacanth, veegum, sodium alginate, carrageenan), a cellulosic derivative (such as sodium carboxymethylcellulose, hydroxypropyl cellulose, methyl cellulose, hydroxypropyl methylcellulose), a polysaccharide (such as starch and pregelatinized starch), an alginate (such as sodium alginate), an acrylic acid copolymer (such as a carbopol), polyvinylpyrrolidone ("PVP"), aluminum magnesium silicate, and any combination thereof. In some embodiments, the suspending agent is selected from hydroxyethyl cellulose, hydroxypropyl methylcellulose, xanthan gum, microcrystalline cellulose, sodium carboxymethyl cellulose, and any combination thereof. In some embodiments, the suspending agent is a hydrocolloid gum. In some embodiments, the suspending agent is xanthan gum.

In some embodiments, the at least one pharmaceutically acceptable excipient is a preservative. In some embodiments, the preservative is present in an amount ranging from about 0.10% w/w to about 1.00% w/w based on the total weight of the composition. In some embodiments, the preservative is present in an amount ranging from about 0.10% w/w to about 0.50% w/w based on the total weight of the composition. In some embodiments, the preservative is present in an amount of about 0.10% w/w based on the total weight of the composition. In some embodiments, the preservative is selected from sodium benzoate and benzyl alcohol.

In some embodiments, the at least one pharmaceutically acceptable excipient is a sweetener. In some embodiments, the sweetener is present in an amount ranging from about 0.10% w/w to about 1.00% w/w based on the total weight of the composition. In some embodiments, the sweetener is present in an amount ranging from about 0.10% w/w to about 0.50% w/w based on the total weight of the composition. In some embodiments, the sweetener is present in an amount of about 0.30% w/w based on the total weight of the composition. In some embodiments, the sweetener is selected from sucralose, glucose, sorbitol, aspartame, saccharin sodium, and any combination thereof. In some embodiments, the sweetener is sucralose.

In some embodiments, the at least one pharmaceutically acceptable excipient is an antifoaming agent. In some embodiments, the antifoaming agent is present in an amount ranging from about 0.10% w/w to about 1.00% w/w based on the total weight of the composition. In some embodiments, the antifoaming agent is present in an amount ranging from about 0.10% w/w to about 0.50% w/w based on the total weight of the composition. In some embodiments, the antifoaming agent is present in an amount of about 0.20% w/w based on the total weight of the composition. In some embodiments, the antifoaming agent is a simethicone emulsion, such as simethicone emulsion (30%) USP.

In some embodiments, the at least one pharmaceutically acceptable excipient is an anti-caking agent. In some embodiments, the anti-caking agent is present in an amount ranging from about 0.10% w/w to about 1.00% w/w based on the total weight of the composition. In some embodiments, the anti-caking agent is present in an amount ranging from about 0.10% w/w to about 0.50% w/w based on the total weight of the composition. In some embodiments, the anti-caking agent is present in an amount of about 0.50% w/w based on the total weight of the composition. In some embodiments, the anti-caking agent is silicon dioxide.

In some embodiments, the at least one pharmaceutically acceptable excipient is a diluent. In some embodiments, the diluent is present in an amount ranging from about 10% to about 90% by weight of the composition, for example when the composition is a powder. In some embodiments, the diluent is selected from sucrose, dextrose, mannitol, sorbitol, maltitol, starch, lactose, microcrystalline cellulose, and any combination thereof. In some embodiments, the diluent is sucrose.

In some embodiments, the diluent has a D90 ranging from about 1 μm to about 600 μm, from about 5 μm to about 500 μm, from about 10 μm to about 500 μm, from about 20 μm to about 400 μm, from about 30 μm to about 200 μm, or from about 50 μm to about 180 μm. In some embodiments, the diluent (such as sucrose) has a D90 ranging from about 50 μm to about 400 μm.

In some embodiments, the diluent is mixed with the suspending agent.

In some embodiments, the at least one pharmaceutically acceptable excipient is a flavoring agent. In some embodiments, the amount of the flavoring agent in the composition is between about 0.1% to about 5.0% w/w based on the total weight of the composition. In some embodiments, the flavoring agent is selected from grenadine flavor, berry flavor, strawberry flavor, banana flavor, orange flavor and peppermint flavor.

In some embodiments, the at least one pharmaceutically acceptable excipient is a lubricant. In some embodiments, the lubricant is present in the composition in an amount ranging from about 0.1% to about 5.0% w/w based on the total weight of the composition. In some embodiments, the lubricant is selected from silicon dioxide, magnesium stearate, talc, sodium stearyl fumarate, and any combination thereof.

In some embodiments, when the composition is in the form of a suspension, the composition further comprises a buffering agent. In some embodiments, when the composition is in the form of a suspension, the buffer concentration is in an amount ranging from about 10 mM to about 200 mM, from about 10 mM to about 100 mM, or from about 10 mM to about 50 mM. In some embodiments, the buffering agent is selected from sodium citrate, citric acid, tartaric acid, potassium citrate, sodium bicarbonate, potassium bicarbonate, sodium dihydrogen phosphate, disodium hydrogen phosphate, sodium hydroxide, and potassium dihydrogen phosphate. In some embodiments, the compositions herein do not contain a buffering agent. In some embodiments, the compositions herein do not contain citric acid.

In some embodiments, the composition described herein comprises a salting agent and a suspending agent. In some embodiments, the composition described herein comprises a salting agent and a pH adjuster. In some embodiments, the composition described herein comprises a suspending agent and a pH adjuster. In some embodiments, the composition described herein comprises a salting agent, a pH adjuster, a suspending agent, and an antifoaming agent. In some embodiments, the composition described herein comprises a salting agent, a pH adjuster, a suspending agent, an antifoaming agent, and an anti-caking agent. In some embodiments, the composition described herein comprises a salting agent, a pH adjuster, a suspending agent, an antifoaming agent, an anti-caking agent, and a preservative.

In some embodiments, when the composition is in the form of a suspension, the pH of the suspension ranges from about 3.0 to about 7.0, from about 3.0 to about 6.0, or from about 3.0 to about 5.0. In some embodiments, the pH ranges from about 3.0 to about 5.0. In some embodiments, the pH ranges from about 3.5 to about 5.0. In some embodiments, the pH ranges from about 3.6 to about 4.8. In some embodiments, the pH ranges from about 4.0 to about 4.5.

In some embodiments, the suspension has a pH of from about 3.5 to about 5.0, from about 3.6 to about 4.8, from about 3.6 to about 4.6, from about 3.6 to about 4.1, from about 3.6 to about 4.0, from about 3.6 to about 4.1, from about 4.0 to about 4.5, from about 4.0 to about 4.1, or from about 4.3 to about 5.0. In some embodiments, the suspension has a pH of about 4.0. In some embodiments, the suspension has a pH of about 4.6.

In some embodiments, the lamotrigine salt or co-crystal, or hydrate or solvate thereof, is present in the composition in an amount that is equivalent to an amount ranging from about 0.1% to about 10.0% lamotrigine (free base) by weight of the composition. In some embodiments, the lamotrigine salt or co-crystal, or hydrate or solvate thereof, is present in the composition in an amount that is equivalent to an amount ranging from about 0.1% to about 5.0% lamotrigine (free base) by weight of the composition. In some embodiments, the lamotrigine salt or co-crystal, or hydrate or solvate thereof, is present in the composition in an amount that is equivalent to an amount ranging from about 0.1% to about 4.5%, from about 0.1% to about 4.0%, from about 0.1% to about 3.5%, from about 0.1% to about 3.0%, from about 0.1% to about 2.5%, from about 0.1% to about 2.0%, from about 0.1% to about 1.5%, from about 0.1% to about 1.0%, or from about 0.1% to about 0.5% lamotrigine (free base) by weight of the composition. In some embodiments, the lamotrigine salt or co-crystal, or hydrate or solvate thereof, is present in the composition in an amount that is equivalent to an amount ranging from about 0.5% to about 2.5% lamotrigine (free base) by weight of the composition.

In some embodiments, the lamotrigine salt or co-crystal, or hydrate or solvate thereof, is present in an amount that is equivalent to an amount of about 0.5% lamotrigine (free base) by weight of the composition. In some embodiments, the lamotrigine salt or co-crystal, or hydrate or solvate thereof, is present in an amount that is equivalent to an amount of about 2.5% lamotrigine (free base) by weight of the composition.

In some embodiments, when the composition is in the form of a suspension, the lamotrigine salt or co-crystal, or hydrate or solvate thereof, is present in a range in the composition in an amount that is equivalent to from about 1 mg/mL to about 50 mg/mL lamotrigine (free base). In some embodiments, when the composition is in the form of a suspension, the lamotrigine salt or co-crystal, or hydrate or solvate thereof, is present in a range in the composition in an amount that is equivalent to from about 2 mg/mL to about 30 mg/mL or from about 5 mg/mL to about 25 mg/mL lamotrigine (free base).

In some embodiments, when the composition is in the form of a suspension, the lamotrigine salt or co-crystal, or hydrate or solvate thereof, is present in an amount equivalent to about 5 mg/mL lamotrigine (free base). In some embodiments, when the composition is in the form of a suspension, the lamotrigine salt or co-crystal, or hydrate or solvate thereof, is present in an amount equivalent to about 25 mg/mL lamotrigine (free base).

In some embodiments, the compositions comprising a lamotrigine salt or co-crystal, or a hydrate or solvate thereof, exhibit an improved absorption and pharmacokinetic (PK) profile when administered to a subject as compared to a composition comprising lamotrigine (free base) when administered to a subject.

In some embodiments, the compositions comprising a lamotrigine salt or co-crystal, or a hydrate or solvate thereof, exhibit an increased rate of dissolution as compared to a composition comprising lamotrigine (e.g., Lamictal®). In some embodiments, the dissolution is measured by methods in the United States Pharmacopcia (USP). In some embodiments, the dissolution is measured in water, FaSSGF, FaSSIF, or FeSSIF. In some embodiments, the dissolution is measured in water.

In some embodiments, the compositions comprising a lamotrigine salt or co-crystal, or a hydrate or solvate thereof, exhibit a sustained release profile as compared to a composition comprising lamotrigine (e.g., Lamictal®) when administered to a subject. In some embodiments, the release profile is measured by methods in the United States Pharmacopcia (USP), such as the USP dissolution apparatus 2 in 900 mL of pH 6.8 at 50 RPM.

In some embodiments, when the composition is in the form of a dry solid (e.g., a powder), the composition is prepared by mixing the lamotrigine salt or co-crystal, or hydrate or solvate thereof, and at least one pharmaceutical excipient. In some embodiments, the lamotrigine salt or co-crystal, or hydrate or solvate thereof, is mixed with a suspending agent and/or a diluent. Exemplary methods of preparation include dry powder blending, wet granulation, dry granulation by compaction or slugging, spray drying, hot melt extrusion, extrusion spheronization, and fluidized bed granulation. In some embodiments, the lamotrigine salt or co-crystal, or hydrate or solvate thereof, and excipient(s) have a particle size that is suitable for passing through certain mesh, for example mesh 20, mesh 40, mesh 60, mesh 80, or mesh 100.

In some embodiments, when the composition is in the form of a liquid (e.g., a suspension), the composition is prepared by reconstituting a dry composition (e.g., a powder) with a pharmaceutically acceptable carrier. In some embodiments, the liquid composition is prepared by adding water to the dry composition and mixing thoroughly. In some embodiments, the preparation of the liquid composition further comprises the use of a measuring cup or a syringe. In some embodiments, the use of the cup or syringe allows a precise dosage to be obtained.

In some embodiments, the pharmaceutically acceptable carrier is present in an amount ranging from about 25% w/w to about 99% w/w based on the total weight of the liquid composition. In some embodiments, the pharmaceutically acceptable carrier is present in an amount ranging from about 25% w/w to about 99%, from about 50% to about 99%, from about 75% to about 99%, from about 90% to about 99%, or from about 95% to about 99% w/w based on the total weight of the liquid composition. In some embodiments, the pharmaceutically acceptable carrier is present in an amount of about 95% w/w based on the total weight of the liquid composition. In some embodiments, the pharmaceutically acceptable carrier is present in an amount of about 98% w/w based on the total weight of the liquid composition.

In some embodiments, the pharmaceutically acceptable carrier is water, such as purified water. In some embodiments, the pharmaceutically acceptable carrier is an aqueous solution containing one or more additional excipients.

In some embodiments, the reconstituted composition that is in the form of a suspension provides longer stability, dose titration accuracy, and better compliance compared with conventional non-suspension dosage forms (e.g., Lamictal®).

In some embodiments, when the composition is in the form of a liquid (e.g., a suspension), the liquid composition is easier to swallow than a known composition comprising lamotrigine (e.g., Lamictal®). In some embodiments, the liquid composition provides case of dosing. In some embodiments, the liquid composition increases patient compliance due to, for example, case of dosing. In some embodiments, the liquid composition provides more accurate dosing compared to, for example, known compositions (e.g., Lamictal®). In some embodiments, the liquid composition comprises minimal ingredients in order to, for example, reduce the potential for reactions, such as allergic reactions, to the composition. In some embodiments, the liquid composition is ready-to-use. In some embodiments, the liquid composition is suitable for administration without diluting the composition prior to administration. In some embodiments, the liquid composition is shelf stable. In some embodiments, the liquid composition is suitable for oral delivery. In some embodiments, the liquid composition is in the form of an oral dosage form.

In one aspect, the present disclosure relates to a kit comprising: (i) a first container comprising a lamotrigine salt or co-crystal, or a hydrate or solvate thereof, or a pharmaceutical composition comprising a lamotrigine salt or co-crystal, or hydrate or solvate thereof; and (ii) a second container comprising a vehicle.

In some embodiments, the first container comprises a lamotrigine salt or co-crystal, or a hydrate or solvate thereof. In some embodiments, the first container comprises a pharmaceutical composition comprising a lamotrigine salt or co-crystal, or hydrate or solvate thereof, and at least one excipient.

In some embodiments, the lamotrigine salt or co-crystal, or a hydrate or solvate thereof, or a pharmaceutical composition in the first container is in the form of a powder. In some embodiments, the powder has a particle size that is suitable for passing through certain mesh, for example mesh 20, mesh 40, mesh 60, mesh 80, or mesh 100.

In some embodiments, the vehicle in the second container comprises water. In some embodiments, the vehicle in the second container comprises a pH adjuster. In some embodiments, the vehicle in the second container comprises a salting agent. In some embodiments, the vehicle in the second container comprises a suspending agent. In some embodiments, the vehicle in the second container comprises a salting agent and a pH adjuster. In some embodiments, the vehicle in the second container comprises a salting agent, a pH adjuster, and a suspending agent.

In some embodiments, the second container comprises from about 10 mL to about 500 mL of the vehicle. In some embodiments, the second container comprises from about 25 mL to about 400 mL of the vehicle. In some embodiments, the second container comprises about 25 mL of the vehicle, about 50 mL of the vehicle, about 75 mL of the vehicle, about 100 mL of the vehicle, about 125 mL of the vehicle, about 150 mL of the vehicle, about 175 mL of the vehicle, about 200 mL of the vehicle, about 225 mL of the vehicle, about 250 mL of the vehicle, about 275 mL of the vehicle, about 300 mL of the vehicle, about 325 mL of the vehicle, about 350 mL of the vehicle, about 375 mL of the vehicle, or about 400 mL of the vehicle. In some embodiments, the second container comprises about 50 mL of the vehicle. In some embodiments, the second container comprises about 100 mL of the vehicle. In some embodiments, the second container comprises about 200 mL of the vehicle. In some embodiments, the second container comprises about 300 mL of the vehicle.

In some embodiments, the kit further comprises a tool for scraping the lamotrigine salt or co-crystal, or a hydrate or solvate thereof, or a pharmaceutical composition in the first container into the vehicle in the second container or for scraping the vehicle in the second container into the lamotrigine salt or co-crystal, or a hydrate or solvate thereof, or a pharmaceutical composition in the first container.

In some embodiments, when the contents of the first container are combined with the vehicle in the second container, the resultant combination is in the form of a suspension.

In some embodiments, the resultant combination comprises a lamotrigine fumarate salt (for example, a lamotrigine hemifumarate anhydrate).

In some embodiments, the resultant combination comprises from about 5 mg/ml to about 50 mg/mL of lamotrigine or a salt or co-crystal thereof, or a hydrate or solvate thereof. In some embodiments, the resultant combination comprises a dose of about 5 mg/ml of lamotrigine or a salt or co-crystal thereof, or a hydrate or solvate thereof. In some embodiments, the resultant combination comprises about 25 mg/mL of lamotrigine or a salt or co-crystal thereof, or a hydrate or solvate thereof. In some embodiments, the resultant combination comprises about 50 mg/mL of lamotrigine or a salt or co-crystal thereof, or a hydrate or solvate thereof.

In some embodiments, the resultant combination comprises an amount of lamotrigine or a salt or co-crystal thereof, or a hydrate or solvate thereof, that is equivalent to from about 5 mg/mL to about 50 mg/mL of lamotrigine (free base). In some embodiments, the resultant combination comprises an amount of lamotrigine or a salt or co-crystal thereof, or a hydrate or solvate thereof, that is equivalent to about 5 mg/mL of lamotrigine (free base). In some embodiments, the resultant combination comprises an amount of lamotrigine or a salt or co-crystal thereof, or a hydrate or solvate thereof, that is equivalent to about 25 mg/ml of lamotrigine (free base). In some embodiments, the resultant combination comprises an amount of lamotrigine or a salt or co-crystal thereof, or a hydrate or solvate thereof, that is equivalent to about 50 mg/mL of lamotrigine (free base).

In some embodiments, the resultant combination is stable. In some embodiments, the resultant combination is stable after being stored at about 5° C., at about room temperature, at about 40° C., or after being subjected to accelerated stability conditions for a period time, for example, for about 6 months or about 24 months. In some embodiments, the resultant combination comprises less than about 1% solubilized lamotrigine (free base).

In some embodiments, the resultant combination has a pH of from about 3.0 to about 5.0, for example, about 3.5 to about 5.0, from about 3.6 to about 4.8, from about 3.6 to about 4.6, from about 3.6 to about 4.1, from about 3.6 to about 4.0, from about 3.6 to about 4.1, from about 4.0 to about 4.5, from about 4.0 to about 4.1, or from about 4.3 to about 5.0.

In some embodiments, the resultant combination is any of the compositions described herein.

In another aspect, the present disclosure relates to methods of treating a disease or condition using a lamotrigine salt or co-crystal, or a hydrate or solvate thereof, a pharmaceutical composition, or a kit as disclosed herein. Examples of the disease or condition include epilepsy, bipolar disorder (e.g. of bipolar I disorder and bipolar II disorder), depression, and neurofibromatosis. Examples of epilepsy include tonic-clonic seizures (includes simple partial, complex partial and secondarily generalized seizures). As such, a lamotrigine salt or co-crystal, or a hydrate or solvate thereof, a pharmaceutical composition, or a kit as disclosed herein may be useful as an adjunctive therapy for the following seizure types in patents with epilepsy: partial on-set seizures, primary generalized tonic-clonic (PGTC) seizures; and/or generalized seizures of Lennox-Gastaut syndrome. In addition, a lamotrigine salt or co-crystal, or a hydrate or solvate thereof, a pharmaceutical composition, or a kit as disclosed herein may also be useful for conversion to monotherapy in subjects with partial-onset seizures who are receiving treatment with a single antiepileptic drug (AED), such as carbamazepine, phenytoin, phenobarbital, primidone, or valproate. Further, a lamotrigine salt or co-crystal, or a hydrate or solvate thereof, a pharmaceutical composition, or a kit as disclosed herein may also be useful for the maintenance treatment of bipolar I disorder to delay the time to occurrence of mood episodes (depression, mania, hypomania, mixed episodes) in patients treated for acute mood episodes with standard therapy.

In some embodiments, the lamotrigine salt or co-crystal, or hydrate or solvate thereof, the pharmaceutical composition, or the kit as disclosed herein is an adjuvant therapy in partial seizures (e.g., focal onset tonic-clonic, atypical absence, myoclonic, and due to Lennox-Gastaut syndrome). In some embodiments, the lamotrigine salt or co-crystal, or hydrate or solvate thereof, the pharmaceutical composition, or the kit as disclosed herein is an alternative therapy for absence seizure and atypical absence, myoclonic, and atonic seizures. Other exemplary applications include treatment of peripheral neuropathy, trigeminal neuralgia, cluster headaches, migraines, and neuropathic pain.

In some embodiments, the present disclosure relates to methods of treating epilepsy using a lamotrigine salt or co-crystal, or hydrate or solvate thereof, a pharmaceutical composition, or a kit as disclosed herein. In some embodiments, the treatment is used as a monotherapy. In some embodiments, the treatment is used as an adjunctive therapy.

In some embodiments, the method of treating a subject with epilepsy comprises administering to a subject in need thereof a lamotrigine salt or co-crystal, or a hydrate or solvate thereof, or a pharmaceutical composition as disclosed herein. In some embodiments, the method of treating a subject with epilepsy comprises combining the first container and the second container in a kit as disclosed herein and administering the resultant combination to the subject.

In some embodiments, the lamotrigine salt or co-crystal, or a hydrate or solvate thereof, pharmaceutical composition, or resultant combination is used as a monotherapy. In some embodiments, the monotherapy is for subjects aged about 16 years or older. In some embodiments, the monotherapy is for subjects suffering from partial-onset seizures. In some embodiments, the subjects with partial-onset seizures are or were receiving treatment with another antiepileptic drug (such as, for example, carbamazepine, phenytoin, phenobarbital, primidone, or valproate).

In some embodiments, the lamotrigine salt or co-crystal, or a hydrate or solvate thereof, pharmaceutical composition, or resultant combination is used as an adjunctive therapy. In some embodiments, the adjunctive therapy is for subjects aged about 2 years or older. In some embodiments, the adjunctive therapy is for subjects suffering from partial-onset seizures. In some embodiments, the adjunctive therapy is for subjects suffering from primary generalized tonic-clonic seizures. In some embodiments, the adjunctive therapy is for subjects suffering from generalized seizures of Lennox-Gastaut syndrome. When referring to a subject suffering from seizures and the like, it should be understood that even a patient who has single seizure can be consider to be "a subject suffering from seizures."

In some embodiments, the present disclosure relates to methods of treating bipolar disorder using a lamotrigine salt or co-crystal, or hydrate or solvate thereof, a pharmaceutical composition, or a kit as disclosed herein.

In some embodiments, the method of treating a subject with bipolar disorder comprises administering to a subject in need thereof a lamotrigine salt or co-crystal, or a hydrate or solvate thereof, or a pharmaceutical composition as disclosed herein. In some embodiments, the method of treating a subject with bipolar disorder comprises combining the first container and the second container in a kit as disclosed herein and administering the resultant combination to the subject.

In some embodiments, the lamotrigine salt or co-crystal, or a hydrate or solvate thereof, pharmaceutical composition, or resultant combination is used as a maintenance treatment of a bipolar disorder, such as bipolar I disorder. In some embodiments, the lamotrigine salt or co-crystal, or a hydrate or solvate thereof, pharmaceutical composition, or resultant combination is used as a maintenance treatment of bipolar I disorder to delay the time to occurrence of mood episodes in subjects treated for acute mood episodes with standard therapy.

In some embodiments, the present disclosure relates to methods of treating a disease or condition using a lamotrigine salt or co-crystal, or hydrate or solvate thereof, a pharmaceutical composition, or a kit as disclosed herein, wherein the disease or condition is selected from partial on-set seizures, primary generalized tonic-clonic seizures, generalized seizures of Lennox-Gastaut syndrome, bipolar I disorder, acute mood episodes, acute manic episodes, and mixed mood episodes.

In some embodiments, in any of the methods disclosed herein, the subject self-administers the lamotrigine salt or co-crystal, or a hydrate or solvate thereof, or the pharmaceutical composition, or the resultant combination from the kit.

In some embodiments, in any of the methods disclosed herein, someone other than the subject administers the lamotrigine salt or co-crystal, or a hydrate or solvate thereof, or the pharmaceutical composition, or the resultant combination from the kit to the subject.

In some embodiments, the lamotrigine salt or co-crystal, or a hydrate or solvate thereof, or the pharmaceutical composition, or the resultant combination is administered in a dose of from about 1 mg to about 1000 mg of lamotrigine (free base) per day. In some embodiments, the dose is from about 1 mg to about 700 mg of lamotrigine (free base) per day. In some embodiments, the dose is from about 1 mg to about 500 mg of lamotrigine (free base) per day.

In some embodiments, the lamotrigine salt or co-crystal, or a hydrate or solvate thereof, or the pharmaceutical composition, or the resultant combination is administered in a dose of from about 25 mg to about 700 mg of lamotrigine (free base) per day.

In some embodiments, the lamotrigine salt or co-crystal, or a hydrate or solvate thereof, or the pharmaceutical composition, or the resultant combination is administered in a dose of from about 100 mg to about 200 mg of lamotrigine (free base) per day.

In some embodiments, the lamotrigine salt or co-crystal, or a hydrate or solvate thereof, or the pharmaceutical composition, or the resultant combination is administered in a dose of from about 100 mg to about 400 mg of lamotrigine (free base) per day.

In some embodiments, the lamotrigine salt or co-crystal, or a hydrate or solvate thereof, or the pharmaceutical composition, or the resultant combination is administered in a dose of from about 225 mg to about 375 mg of lamotrigine (free base) per day.

In some embodiments, the lamotrigine salt or co-crystal, or a hydrate or solvate thereof, or the pharmaceutical composition, or the resultant combination is administered in a dose of from about 300 mg to about 500 mg of lamotrigine (free base) per day.

These In some embodiments, the lamotrigine salt or co-crystal, or a hydrate or solvate thereof, or the pharmaceutical composition, or the resultant combination is administered in a dose of about 25 mg of lamotrigine (free base) every other day. In some embodiments, the dose is about 50 mg of lamotrigine (free base) per day. In some embodiments, the dose is about 100 mg of lamotrigine (free base) per day. In some embodiments, the dose is about 150 mg of lamotrigine (free base) per day. In some embodiments, the dose is about 200 mg of lamotrigine (free base) per day. In some embodiments, the dose is about 250 mg of lamotrigine (free base) per day. In some embodiments, the dose is about 300 mg of lamotrigine (free base) per day. In some embodiments, the dose is about 350 mg of lamotrigine (free base) per day. In some embodiments, the dose is about 400 mg of lamotrigine (free base) per day. In some embodiments, the dose is about 450 mg of lamotrigine (free base) per day. In some embodiments, the dose is about 500 mg of lamotrigine (free base) per day. In some embodiments, the dose is about 550 mg of lamotrigine (free base) per day. In some embodiments, the dose is about 600 mg of lamotrigine (free base) per day. In some embodiments, the dose is about 650 mg of lamotrigine (free base) per day. In some embodiments, the dose is about 700 mg of lamotrigine (free base) per day.

In some embodiments, the lamotrigine salt or co-crystal, or a hydrate or solvate thereof, or the pharmaceutical composition, or the resultant combination is administered in a dose of from about 1 mg to about 10 mg of lamotrigine (free base) per day. In some embodiments, the dose is about 2 mg of lamotrigine (free base) per day or every other day. In some embodiments, the dose is about 3 mg of lamotrigine (free base) per day or every other day. In some embodiments, the dose is about 4 mg of lamotrigine (free base) per day. In some embodiments, the dose is about 5 mg of lamotrigine (free base) per day. In some embodiments, the dose is about 6 mg of lamotrigine (free base) per day or every other day. In some embodiments, the dose is about 7 mg of lamotrigine (free base) per day or every other day. In some embodiments, the dose is about 8 mg of lamotrigine (free base) per day. In some embodiments, the dose is about 9 mg of lamotrigine (free base) per day or every other day. In some embodiments, the dose is about 10 mg of lamotrigine (free base) per day.

In some embodiments, the lamotrigine salt or co-crystal, or a hydrate or solvate thereof, or the pharmaceutical composition, or the resultant combination is administered in a dose of from about 0.10 mg to about 25 mg of lamotrigine (free base) per kilogram of the subject's weight per day. In some embodiments, the dose is from about 0.15 mg to about 15 mg of lamotrigine (free base) per kilogram of the subject's weight per day. In some embodiments, the dose is from about 0.3 mg to about 3.0 mg of lamotrigine (free base) per kilogram of the subject's weight per day.

In some embodiments, the lamotrigine salt or co-crystal, or a hydrate or solvate thereof, or the pharmaceutical composition, or the resultant combination is administered in a dose of about 0.15 mg of lamotrigine (free base) per kilogram of the subject's weight per day. In some embodiments, the dose is about 0.30 mg of lamotrigine (free base) per kilogram of the subject's weight per day. In some embodiments, the dose is about 0.60 mg of lamotrigine (free base) per kilogram of the subject's weight per day. In some embodiments, the dose is about 1.20 mg of lamotrigine (free base) per kilogram of the subject's weight per day.

In some embodiments, the lamotrigine salt or co-crystal, or a hydrate or solvate thereof, or the pharmaceutical composition, or the resultant combination is administered in a dose of from about 1 mg to about 15 mg of lamotrigine (free base) per kilogram of the subject's weight per day. In some embodiments, the dose is from about 1 mg to about 5 mg of lamotrigine (free base) per kilogram of the subject's weight per day. In some embodiments, the dose is from about 1 mg to about 3 mg of lamotrigine (free base) per kilogram of the subject's weight per day. In some embodiments, the dose is from about 4.5 mg to about 7.5 mg of lamotrigine (free base) per kilogram of the subject's weight per day. In some embodiments, the dose is from about 5 mg to about 15 mg of lamotrigine (free base) per kilogram of the subject's weight per day.

Compositions Comprising Lamotrigine or Salts or Co-Crystals Thereof, Kits, and Methods In one aspect, the present disclosure relates to pharmaceutical composition comprising lamotrigine or a salt or co-crystal thereof, or a hydrate or solvate thereof, wherein the composition is a liquid with a pH of from about 3.0 to about 5.0.

In another aspect, the present disclosure relates to a pharmaceutical composition comprising from about 5 mg/mL to about 50 mg/mL of lamotrigine or a salt or co-crystal thereof, or a hydrate or solvate thereof, wherein the composition is in the form of a liquid. In some embodiments, the liquid composition comprises about 5 mg/mL of lamotrigine or a salt or co-crystal thereof, or a hydrate or solvate thereof. In some embodiments, the liquid composition comprises about 25 mg/mL of lamotrigine or a salt or co-crystal thereof, or a hydrate or solvate thereof. In some embodiments, the liquid composition comprises about 50 mg/mL of lamotrigine or a salt or co-crystal thereof, or a hydrate or solvate thereof.

In another aspect, the liquid composition comprising an amount of lamotrigine or a salt or co-crystal thereof, or a hydrate or solvate thereof, that is equivalent to from about 5 mg/mL to about 50 mg/mL of lamotrigine (free base). In another aspect, the liquid composition comprises an amount of lamotrigine or a salt or co-crystal thereof, or a hydrate or solvate thereof, that is equivalent to about 5 mg/mL of lamotrigine (free base). In another aspect, the liquid composition comprises an amount of lamotrigine or a salt or co-crystal thereof, or a hydrate or solvate thereof, that is equivalent to about 25 mg/mL of lamotrigine (free base). In another aspect, the liquid composition comprises an amount of lamotrigine or a salt or co-crystal thereof, or a hydrate or solvate thereof, that is equivalent to about 50 mg/mL of lamotrigine (free base).

In another aspect, the present disclosure relates to a pharmaceutical composition comprising lamotrigine or a salt or co-crystal thereof, or a hydrate or solvate thereof, wherein the composition is a liquid and the amount of lamotrigine or salt or co-crystal thereof, or a hydrate or solvate thereof, in the liquid is stable for about 6 months or more. In another aspect, the present disclosure relates to a pharmaceutical composition comprising lamotrigine or a salt or co-crystal thereof, or a hydrate or solvate thereof, wherein the composition is a liquid and the composition is stable for about 6 months or more. In some embodiments, the composition is stable after being stored at about 5° C., at about room temperature, at about 40° C., or after being subjected to accelerated stability conditions.

In another aspect, the present disclosure relates to a pharmaceutical composition comprising a salt or co-crystal of lamotrigine, wherein the composition is in the form of a liquid.

In another aspect, the present disclosure relates to a pharmaceutical composition comprising lamotrigine and a salting agent, wherein the composition is in the form of a liquid.

In some embodiments, in a pharmaceutical composition disclosed herein, the composition comprises lamotrigine. In some embodiments, in a pharmaceutical composition disclosed herein, the composition comprises a lamotrigine salt. In some embodiments, in a pharmaceutical composition disclosed herein, the composition comprises a lamotrigine co-crystal. In some embodiments, in a pharmaceutical composition disclosed herein, the composition comprises lamotrigine and a lamotrigine salt. In some embodiments, in a pharmaceutical composition disclosed herein, the composition comprises lamotrigine and a lamotrigine co-crystal. In some embodiments, in a pharmaceutical composition disclosed herein, the composition comprises lamotrigine, a lamotrigine salt, and a lamotrigine co-crystal.

In some embodiments, the lamotrigine salt is a fumarate salt, a hydrochloric acid salt, toluenesulfonic acid (TSA) salt, or methanesulfonic acid (MSA) salt. In some embodiments, the lamotrigine salt is a lamotrigine dicarboxylic acid salt. In some embodiments, the lamotrigine salt is a lamotrigine monofumarate, a lamotrigine hemifumarate, a lamotrigine difumarate, or a hydrate and solvate thereof. In some embodiments, the lamotrigine salt or hydrate or solvate thereof is selected from a lamotrigine hemifumarate anhydrate, a lamotrigine hemifumarate solvate, and a lamotrigine hemifumarate hydrate. In some embodiments, the lamotrigine salt or hydrate or solvate thereof is a lamotrigine hemifumarate anhydrate. In some embodiments, the lamotrigine salt or hydrate or solvate thereof is a lamotrigine hemifumarate anhydrate as disclosed herein. For example, in some embodiments, the stoichiometry of the lamotrigine hemifumarate anhydrate is in a range from about 0.50:1 fumarate/lamotrigine to about 0.99:1 fumarate/lamotrigine.

In some embodiments, the lamotrigine co-crystal comprises lamotrigine and a salting agent. In some embodiments, the salting agent is a dicarboxylic acid. In some embodiments, the salting agent is chosen from fumaric acid, disodium fumarate, hydrochloric acid, toluenesulfonic acid (TSA), and methanesulfonic acid (MSA). In some embodiments, the lamotrigine co-crystal comprises lamotrigine, a salting agent, and a lamotrigine salt.

In some embodiments, in a pharmaceutical composition disclosed herein, the pH of the pharmaceutical composition is from about 3.5 to about 5.0. In some embodiments, the pH is from about 3.6 to about 4.8. In some embodiments, the pH is from about 4.0 to about 4.5. In some embodiments, the pH is from about 4.0 to about 5.0. In some embodiments, the pH is from about 4.5 to about 5.0.

In some embodiments, in a pharmaceutical composition disclosed herein, the pH is of from about 3.5 to about 5.0, from about 3.6 to about 4.8, from about 3.6 to about 4.6, from about 3.6 to about 4.1, from about 3.6 to about 4.0, from about 3.6 to about 4.1, from about 4.0 to about 4.5, from about 4.0 to about 4.1, or from about 4.3 to about 5.0. In some embodiments, the pH is about 4.0. In some embodiments, the pH is about 4.6.

In some embodiments, the pH of a pharmaceutical composition disclosed herein is from about 3.0 to about 4.5, from about 3.5 to about 4.5, or from about 4.0 to about 4.5. In some embodiments, the pH is from about 3.0 to about 4.0, from about 3.5 to about 4.0, or from about 3.0 to about 3.5. In some embodiments, the pH is about 3.0, about 3.5, about 4.0, about 4.5, or about 5.0.

In some embodiments, in a pharmaceutical composition disclosed herein, the composition comprises from about 5 mg/mL to about 50 mg/mL lamotrigine or a salt or co-crystal thereof, or a hydrate or solvate thereof. In some embodiments, the composition comprises from about 2 mg/mL to about 30 mg/mL or from about 5 mg/mL to about 25 mg/mL lamotrigine or a salt or co-crystal thereof, or a hydrate or solvate thereof. In some embodiments, the composition comprises about 5 mg/mL lamotrigine or a salt or co-crystal thereof, or a hydrate or solvate thereof. In some embodiments, the composition comprises about 25 mg/mL lamotrigine or a salt or co-crystal thereof, or a hydrate or solvate thereof. In some embodiments, the composition comprises about 50 mg/mL lamotrigine or a salt or co-crystal thereof, or a hydrate or solvate thereof.

In some embodiments, the liquid composition comprising an amount of lamotrigine or a salt or co-crystal thereof, or a hydrate or solvate thereof, that is equivalent to from about 5 mg/mL to about 50 mg/mL of lamotrigine (free base). In another aspect, the liquid composition comprises an amount of lamotrigine or a salt or co-crystal thereof, or a hydrate or solvate thereof, that is equivalent to about 5 mg/mL of lamotrigine (free base). In some embodiments, the liquid composition comprises an amount of lamotrigine or a salt or co-crystal thereof, or a hydrate or solvate thereof, that is equivalent to about 25 mg/mL of lamotrigine (free base). In some embodiments, the liquid composition comprises an amount of lamotrigine or a salt or co-crystal thereof, or a hydrate or solvate thereof, that is equivalent to about 50 mg/ml of lamotrigine (free base).

In some embodiments, in a pharmaceutical composition disclosed herein, the composition comprises a lamotrigine salt or co-crystal, or a hydrate or solvate thereof, in an amount that is equivalent to from about 5 mg/mL to about 50 mg/mL lamotrigine (free base). In some embodiments, the composition comprises a lamotrigine salt or co-crystal there, or a hydrate or solvate thereof, present in an amount that is equivalent to from about 2 mg/mL to about 30 mg/mL or from about 5 mg/mL to about 25 mg/mL lamotrigine (free base). In some embodiments, the composition comprises a lamotrigine salt or co-crystal thereof, or a hydrate or solvate thereof, present in an amount that is equivalent to about 5 mg/mL lamotrigine (free base). In some embodiments, the composition comprises a lamotrigine salt or co-crystal thereof, or a hydrate or solvate thereof, present in an amount that is equivalent to about 25 mg/mL lamotrigine (free base).

In some embodiments, in a pharmaceutical composition disclosed herein, the composition comprises an amount of lamotrigine ranging from about 0.1% to about 10.0% by weight of the composition. In some embodiments, the pharmaceutical composition comprises an amount of lamotrigine ranging from about 0.1% to about 5.0% by weight of the composition. In some embodiments, the pharmaceutical composition comprises an amount of lamotrigine ranging from about 0.1% to about 4.5%, from about 0.1% to about 4.0%, from about 0.1% to about 3.5%, from about 0.1% to about 3.0%, from about 0.1% to about 2.5%, from about 0.1% to about 2.0%, from about 0.1% to about 1.5%, from about 0.1% to about 1.0%, or from about 0.1% to about 0.5% by weight of the composition. In some embodiments, the pharmaceutical composition comprises an amount of lamotrigine ranging from about 0.5% to about 2.5% by weight of the composition.

In some embodiments, the pharmaceutical composition comprises about 0.5% lamotrigine by weight of the composition. In some embodiments, the pharmaceutical composition comprises about 2.5% lamotrigine by weight of the composition.

In some embodiments, in a pharmaceutical composition disclosed herein, the pharmaceutical composition comprises a lamotrigine salt or co-crystal in an amount that is equivalent to an amount ranging from about 0.1% to about 10.0% lamotrigine (free base) by weight of the composition. In some embodiments, the pharmaceutical composition comprises a lamotrigine salt or co-crystal in an amount that is equivalent to an amount ranging from about 0.1% to about 5.0% lamotrigine (free base) by weight of the composition. In some embodiments, the pharmaceutical composition comprises a lamotrigine salt or co-crystal in an amount that is equivalent to an amount ranging from about 0.1% to about 4.5%, from about 0.1% to about 4.0%, from about 0.1% to about 3.5%, from about 0.1% to about 3.0%, from about 0.1% to about 2.5%, from about 0.1% to about 2.0%, from about 0.1% to about 1.5%, from about 0.1% to about 1.0%, or from about 0.1% to about 0.5% lamotrigine (free base) by weight of the composition. In some embodiments, the pharmaceutical composition comprises a lamotrigine salt or co-crystal in an amount that is equivalent to an amount ranging from about 0.5% to about 2.5% lamotrigine (free base) by weight of the composition.

In some embodiments, the pharmaceutical composition comprises a lamotrigine salt or co-crystal in an amount that is equivalent to about 0.5% lamotrigine (free base) by weight of the composition. In some embodiments, the pharmaceutical composition comprises a lamotrigine salt or co-crystal in an amount that is equivalent to about 2.5% lamotrigine (free base) by weight of the composition.

In some embodiments, in a pharmaceutical composition disclosed herein, the amount of solubilized lamotrigine (free base) is less than about 1%. In some embodiments, the amount of solubilized lamotrigine is from about 0.01% to about 1.00%. In some embodiments, the amount of solubilized lamotrigine is from about 0.01% to about 0.90%, from about 0.01% to about 0.80%, from about 0.01 to about 0.70%, from about 0.01% to about 0.60%, from about 0.01% to about 0.50%, from about 0.01% to about 0.40%, from about 0.01% to about 0.30%, from about 0.01% to about 0.20%, or from about 0.01% to about 0.10%.

In some embodiments, in a pharmaceutical composition disclosed herein, the lamotrigine or salt or co-crystal thereof, or a hydrate or solvate thereof, has a D90 of less than about 200 μm, less than about 150 μm, less than about 120 μm, less than about 100 μm, less than about 80 μm, less than about 60 μm, less than about 40 μm. In some embodiments, the D90 ranges from about 5 μm to about 150 μm, from about 10 μm to about 120 μm, from about 20 μm to about 100 μm, or from about 30 μm to about 90 μm. In some embodiments, the D90 ranges from about 25 μm to about 75 μm, from about 30 μm to about 50 μm, or from about 40 μm to about 50 μm.

In some embodiments, in the pharmaceutical compositions disclosed herein, the composition comprises an excipient selected from selected from surface active agents, sweeteners, lubricants, glidants, diluents, smoothing agents, suspension agents, film forming substances, buffering agents, coating assistants, and any combination thereof. In some embodiments, in a pharmaceutical composition disclosed herein, the composition comprises an excipient selected from a pH adjuster; a suspending agent; a preservative; a sweetener; an antifoaming agent; an anti-caking agent; a pharmaceutically acceptable carrier; a salting agent; and any combination thereof.

In some embodiments, the pH adjuster is present in an amount ranging from about 0.001% w/w to about 0.050% w/w based on the total weight of the composition. In some embodiments, the pH adjuster is present in an amount ranging from about 0.001% w/w to about 0.020% w/w based on the total weight of the composition. In some embodiments, the pH adjuster is present in an amount ranging from about 0.001% w/w to about 0.100% w/w based on the total weight of the composition. In some embodiments, the pH adjuster is present in an amount ranging from about 0.004% w/w to about 0.050% w/w based on the total weight of the composition. In In some embodiments, the pH adjuster is present in an amount ranging from about 0.004% w/w to about 0.020% w/w based on the total weight of the composition. In some embodiments, the pH adjuster is present in an amount ranging from about 0.004% w/w to about 0.100% w/w based on the total weight of the composition. In some embodiments, the pH adjuster is selected from sodium hydroxide, hydrochloric acid, phosphoric acid, disodium fumarate, and any combination thereof. In some embodiments, the pH adjuster is selected from sodium hydroxide, hydrochloric acid, and any combination thereof In some embodiments, the suspending agent is present in an amount ranging from about 0.10% w/w to about 10.00% w/w based on the total weight of the composition. In some embodiments, the suspending agent is present in an amount ranging from about 0.10% w/w to about 5.00% w/w based on the total weight of the composition. In some embodiments, the suspending agent is present in an amount ranging from about 0.10% w/w to about 2.00% w/w based on the total weight of the composition. In some embodiments, the suspending agent is present in an amount ranging from about 0.10% w/w to about 0.50% w/w based on the total weight of the composition. In some embodiments, the suspending agent is present in an amount ranging from about 0.10% w/w to about 0.15% w/w based on the total weight of the composition. In some embodiments, the suspending agent is present in an amount of about 0.10% w/w based on the total weight of the composition. In some embodiments, the suspending agent is present in an amount of about 0.15% w/w based on the total weight of the composition.

In some embodiments, the suspending agent reduces the formation of lamotrigine hydrate in the suspension, as compared to an equivalent dose of the lamotrigine (free base) in an equivalent suspension but without the suspending agent.

In some embodiments, the ratio between the lamotrigine or salt or co-crystal thereof, or a hydrate or solvate thereof, and the suspending agent is in a range from about 20:1 to about 1:5 by weight. In some embodiments, the ratio ranges from about 15:1 to about 1:5, from about 10:1 to about 1:5, from about 5:1 to about 1:5, from about 10:1 to about 2:1, from about 10:1 to about 1:1, from about 8:1 to about 4:1, from about 6:1 to about 3:1, or from about 6:1 to about 4:1. In some embodiments, the ratio is about 5:1 by weight.

In some embodiments, the suspending agent is selected from a hydrocolloid gum (such as xanthan gum, guar gum, locust bean gum, gum tragacanth, veegum, sodium alginate, carrageenan), a cellulosic derivative (such as sodium carboxymethylcellulose, hydroxypropyl cellulose, methyl cellulose, hydroxypropyl methylcellulose), a polysaccharide (such as starch and pregelatinized starch), an alginate (such as sodium alginate), an acrylic acid copolymer (such as a carbopol), polyvinylpyrrolidone ("PVP"), aluminum magnesium silicate, and any combination thereof. In some embodiments, the suspending agent is selected from hydroxyethyl cellulose, hydroxypropyl methylcellulose, xanthan gum, microcrystalline cellulose, sodium carboxymethyl cellulose, and any combination thereof. In some embodiments, the suspending agent is a hydrocolloid gum. In some embodiments, the suspending agent is xanthan gum.

In some embodiments, the preservative is present in an amount ranging from about 0.10% w/w to about 1.00% w/w based on the total weight of the composition. In some embodiments, the preservative is present in an amount ranging from about 0.10% w/w to about 0.50% w/w based on the total weight of the composition. In some embodiments, the preservative is present in an amount of about 0.10% w/w based on the total weight of the composition. In some embodiments, the preservative is selected from sodium benzoate and benzyl alcohol.

In some embodiments, the sweetener is present in an amount ranging from about 0.10% w/w to about 1.00% w/w based on the total weight of the composition. In some embodiments, the sweetener is present in an amount ranging from about 0.10% w/w to about 0.50% w/w based on the total weight of the composition. In some embodiments, the sweetener is present in an amount of about 0.30% w/w based on the total weight of the composition. In some embodiments, the sweetener is selected from sucralose, glucose, sorbitol, aspartame, saccharin sodium, and any combination thereof. In some embodiments, the sweetener is sucralose.

In some embodiments, the antifoaming agent is present in an amount ranging from about 0.10% w/w to about 1.00% w/w based on the total weight of the composition. In some embodiments, the antifoaming agent is present in an amount ranging from about 0.10% w/w to about 0.50% w/w based on the total weight of the composition. In some embodiments, the antifoaming agent is present in an amount of about 0.20% w/w based on the total weight of the composition. In some embodiments, the antifoaming agent is a simethicone emulsion.

In some embodiments, the anti-caking agent is present in an amount ranging from about 0.10% w/w to about 1.00% w/w based on the total weight of the composition. In some embodiments, the anti-caking agent is present in an amount ranging from about 0.10% w/w to about 0.50% w/w based on the total weight of the composition. In some embodiments, the anti-caking agent is present in an amount of about 0.50% w/w based on the total weight of the composition. In some embodiments, the anti-caking agent is silicon dioxide.

In some embodiments, the pharmaceutically acceptable carrier is present in an amount ranging from about 25% w/w to about 99% w/w based on the total weight of the liquid composition. In some embodiments, the pharmaceutically acceptable carrier is present in an amount ranging from about 25% w/w to about 99%, from about 50% to about 99%, from about 75% to about 99%, from about 90% to about 99%, or from about 95% to about 99% w/w based on the total weight of the liquid composition. In some embodiments, the pharmaceutically acceptable carrier is present in an amount of about 95% w/w based on the total weight of the liquid composition. In some embodiments, the pharmaceutically acceptable carrier is present in an amount of about 98% w/w based on the total weight of the liquid composition. In some embodiments, the pharmaceutically acceptable carrier is water, such as purified water. In some embodiments, the pharmaceutically acceptable carrier is an aqueous solution containing one or more additional excipients.

In some embodiments, the salting agent is present in an amount ranging from about 0.10% w/w to about 10.00% w/w based on the total weight of the composition. In some embodiments, the salting agent is present in an amount ranging from about 0.10% w/w to about 5.00% w/w based on the total weight of the composition. In some embodiments, the salting agent is present in an amount ranging from about 0.10% w/w to about 1.00% w/w based on the total weight of the composition. In some embodiments, the salting agent is present in an amount ranging from about 0.10% w/w to about 0.75% w/w based on the total weight of the composition. In some embodiments, the salting agent is present in an amount ranging from about 0.10% w/w to about 0.70% w/w based on the total weight of the composition. In some embodiments, the salting agent is present in an amount of about 0.10% w/w based on the total weight of the composition. In some embodiments, the salting agent is present in an amount of about 0.70% w/w based on the total weight of the composition. In some embodiments, the salting agent is chosen from fumaric acid, disodium fumarate, hydrochloric acid, toluenesulfonic acid (TSA), and methanesulfonic acid (MSA). In some embodiments, the salting agent is fumaric acid or disodium fumarate.

In some embodiments, the diluent is present in an amount ranging from about 10% to about 90% by weight of the composition. In some embodiments, the diluent is selected from sucrose, dextrose, mannitol, sorbitol, maltitol, starch, lactose, microcrystalline cellulose, and any combination thereof. In some embodiments, the diluent is sucrose.

In some embodiments, the diluent has a D90 ranging from about 1 μm to about 600 μm, from about 5 μm to about 500 μm, from about 10 μm to about 500 μm, from about 20 μm to about 400 μm, from about 30 μm to about 200 μm, or from about 50 μm to about 180 μm. In some embodiments, the diluent (such as sucrose) has a D90 ranging from about 50 μm to about 400 μm.

In some embodiments, the diluent is mixed with the suspending agent.

In some embodiments, the amount of the flavoring agent in the composition is between about 0.1% to about 5.0% w/w based on the total weight of the composition. In some embodiments, the flavoring agent is selected from grenadine flavor, berry flavor, strawberry flavor, banana flavor, orange flavor and peppermint flavor.

In some embodiments, the lubricant is present in the composition in an amount ranging from about 0.1% to about 5.0% w/w based on the total weight of the composition. In some embodiments, the lubricant is selected from silicon dioxide, magnesium stearate, talc, sodium stearyl fumarate, and any combination thereof.

In some embodiments, the buffer concentration is in an amount ranging from about 10 mM to about 200 mM, from about 10 mM to about 100 mM, or from about 10 mM to about 50 mM. In some embodiments, the buffering agent is selected from sodium citrate, citric acid, fumaric acid, tartaric acid, potassium citrate, sodium bicarbonate, potassium bicarbonate, sodium dihydrogen phosphate, disodium hydrogen phosphate, sodium hydroxide, and potassium dihydrogen phosphate. In some embodiments, the compositions herein do not contain a buffering agent. In some embodiments, the compositions herein do not contain citric acid.

In some embodiments, a composition as described herein comprises a salting agent and a suspending agent. In some embodiments, the composition comprises a salting agent and a pH adjuster. In some embodiments, the composition comprises a suspending agent and a pH adjuster. In some embodiments, the composition comprises a salting agent, a pH adjuster, a suspending agent, and an antifoaming agent. In some embodiments, the composition comprises a salting agent, a pH adjuster, a suspending agent, an antifoaming agent, and an anti-caking agent. In some embodiments, the composition comprises a salting agent, a pH adjuster, a suspending agent, an antifoaming agent, an anti-caking agent, and a preservative.

In some embodiments, a composition as described herein is stable after being stored at about 5° C. for a period of time. In some embodiments, the composition is stable after being stored at room temperature (about 25° C.) for a period of time. In some embodiments, the composition is stable after being stored at about 40° C. for a period of time. In some embodiments, the period of time is less than about 1 month. In some embodiments, the period of time is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, or more. In some embodiments, the period of time is at least about 24 months. In some embodiments, the period of time is about 1 month, about 2 months, about 3 months, about 4 months, about 5 months, about 6 months, about 7 months, about 8 months, about 9 months, about 10 months, about 11 months, about 12 months, or more. In some embodiments, the period of time is about 6 months. In some embodiments, the period of time is about 24 months.

In some embodiments, a composition as described herein is stable after being subjected to accelerated stability conditions. In some embodiments, the accelerated stability conditions are about 40° C. and about 75% relative humidity (RH) for a period of time. In some embodiments, the accelerated stability conditions are about 60° C. at room temperature for a period of time. In some embodiments, the period of time is less than about 1 month. In some embodiments, the period of time is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, or more. In some embodiments, the period of time is at least about 24 months. In some embodiments, the period of time is about 1 month, about 2 months, about 3 months, about 4 months, about 5 months, about 6 months, about 7 months, about 8 months, about 9 months, about 10 months, about 11 months, about 12 months, or more. In some embodiments, the period of time is about 6 months. In some embodiments, the period of time is about 24 months.

In some embodiments, in a pharmaceutical composition disclosed herein, the composition is in the form of a suspension. In some embodiments, the suspension is homogeneous.

In some embodiments, when the composition is a suspension, the suspension may be stable for at least 3 months. In some embodiments, the suspension is stable for at least 4 months, at least 5 months, at least 6 months, at least 7 months, at least 8 months, or at least 9 months. In some embodiments, the suspension is stable for at least 6 months. In some embodiments, the suspension is stable for at least 12 months. In some embodiments, the suspension is stable for at least 24 months. In some embodiments, the suspension is stable after being stored at about 5° C. for a period of time, at room temperature (about 25° C.) for a period of time, at about 40° C. for a period of time, or after being subjected to accelerated stability conditions for a period of time as discussed herein. Stability can be measured by, for example, UPLC.

In some embodiments, the suspension maintains a sedimentation volume ratio of more than about 0.7, more than about 0.8, or more than about 0.9 for a period of at least about 10 hours, at least about 12 hours, at least about 15 hours, at least about 18 hours, at least about 20 hours, at least about 24 hours, at least about 30 hours, or at least about 48 hours after the composition is reconstituted. In some embodiments, the sedimentation volume ratio is achieved within about 5 minutes, about 3 minutes, about 2 minutes, about 60 seconds, about 45 seconds, or about 30 seconds after the composition is reconstituted to a suspension. Various mechanical means, such as shaking, swirling, heating, or any combination thereof can be used to promote a uniform suspension.

In some embodiments, in a pharmaceutical composition disclosed herein, less than about 5%, less than about 3%, less than about 1%, less than about 0.5%, less than about 0.2%, or less than about 0.1% of the lamotrigine or salt or co-crystal thereof, or a hydrate or solvate thereof, is decomposed (for example, into Lamotrigine Impurity C) in about 10 hours, in about 20 hours, in about 24 hours, in about 2 days, in about 3 days, or in about 1 week after the composition is prepared (for example, in the form of a suspension). In some embodiments, less than about 0.5% of the lamotrigine or salt or co-crystal thereof, or a hydrate or solvate thereof, decomposes within about 24 hours after the composition is reconstituted into a suspension.

In some embodiments, in a pharmaceutical composition disclosed herein, less than about 5%, less than about 3%, less than about 1%, less than about 0.5%, less than about 0.2%, or less than about 0.1% of the lamotrigine or salt or co-crystal thereof, or a hydrate or solvate thereof, is decomposed (for example, into Lamotrigine Impurity C) when measured after being stored at about 5° C. for a period of time, at room temperature (about 25° C.) for a period of time, at about 40° C. for a period of time, or under accelerated stability conditions for a period of time. In some embodiments, the period of time is less than about 1 month. In some embodiments, the period of time is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, or more. In some embodiments, the period of time is at least about 24 months. In some embodiments, the period of time is about 1 month, about 2 months, about 3 months, about 4 months, about 5 months, about 6 months, about 7 months, about 8 months, about 9 months, about 10 months, about 11 months, about 12 months, or more. In some embodiments, the period of time is about 6 months. In some embodiments, the period of time is about 24 months. Decomposition can be measured by, for example, UPLC.

In some embodiments, the pharmaceutical compositions disclosed herein provide an in vitro release of at least about 95%, at least about 90%, at least about 85%, at least about 80%, at least about 70%, or at least about 60% of lamotrigine in a medium of pH of 1 after 5 minutes. In some embodiments, the pharmaceutical composition provides an in vitro release of at least about 85% of lamotrigine (free base) in a pH 1 medium after 5 minutes. In some embodiments, the release is measured by a method in the United States Pharmacopeia (USP), for example using a USP dissolution apparatus 1 or USP dissolution apparatus 2. In some embodiments, the release is measured using a USP dissolution apparatus 2 in 900 mL of pH 6.8 at 50 RPM.

In some embodiments, the pharmaceutical compositions disclosed herein provide a release of lamotrigine that is bioequivalent to non-suspension formulation of lamotrigine (e.g., Lamictal®) at the same dose.

In some embodiments, the pharmaceutical compositions disclosed herein exhibit an improved absorption and pharmacokinetic (PK) profile when administered to a subject as compared to a known composition comprising lamotrigine (e.g., Lamictal®) when administered to a subject.

In some embodiments, the pharmaceutical compositions disclosed herein exhibit an increased rate of dissolution as compared to a known composition comprising lamotrigine (e.g., Lamictal®). In some embodiments, the dissolution is measured by methods in the United States Pharmacopeia (USP). In some embodiments, the dissolution is measured in water, FaSSGF, FaSSIF, or FeSSIF. In some embodiments, the dissolution is measured in water.

In some embodiments, the compositions comprising a lamotrigine salt or co-crystal, or a hydrate or solvate thereof, exhibit a sustained release profile as compared to a known composition comprising lamotrigine (e.g., Lamictal®) when administered to a subject. In some embodiments, the release profile is measured by methods in the United States Pharmacopeia (USP), such as the USP dissolution apparatus 2 in 900 mL of pH 6.8 at 50 RPM.

In some embodiments, when the composition is in the form of a dry solid (e.g., a powder), the composition is prepared by mixing the lamotrigine or salt or co-crystal thereof, or a hydrate or solvate thereof, and at least one pharmaceutical excipient. In some embodiments, the lamotrigine or salt or co-crystal thereof, or a hydrate or solvate thereof, is mixed with a suspending agent, and/or a diluent. Exemplary methods of preparation include dry powder blending, wet granulation, dry granulation by compaction or slugging, spray drying, hot melt extrusion, extrusion spheronization, and fluidized bed granulation. In some embodiments, the lamotrigine or salt or co-crystal thereof, or a hydrate or solvate thereof, and the excipient(s), individually or when mixed together, have a particle size that is suitable for passing through certain mesh, for example mesh 20, mesh 40, mesh 60, mesh 80, or mesh 100. In some embodiments, the lamotrigine or salt or co-crystal thereof, or a hydrate or solvate thereof, and the excipient(s), individually or when mixed together, have a particle size distribution of D90 not more than 60 μm.

In some embodiments, when the composition is in the form of a liquid (e.g., a suspension), the composition is prepared by reconstituting a dry composition (e.g., a powder) with a pharmaceutically acceptable carrier (e.g., water optionally comprising other excipients). In some embodiments, the liquid composition is prepared by adding water to the dry composition and mixing thoroughly. In some embodiments, the preparation of the liquid composition further comprises the use of a measuring cup or a syringe. In some embodiments, the use of the cup or syringe allows a precise dosage to be obtained.

In some embodiments, when the composition is in the form of a liquid (e.g., a suspension), the liquid composition is easier to swallow than a known composition comprising lamotrigine (e.g., Lamictal®). In some embodiments, the liquid composition provides case of dosing. In some embodiments, the liquid composition increases patient compliance due to, for example, case of dosing. In some embodiments, the liquid composition provides more accurate dosing compared to, for example, known compositions (e.g., Lamictal®). In some embodiments, the liquid composition comprises minimal ingredients in order to, for example, reduce the potential for reactions, such as allergic reactions, to the composition. In some embodiments, the liquid composition is ready-to-use. In some embodiments, the liquid composition is suitable for administration without diluting the composition prior to administration. In some embodiments, the liquid composition is shelf stable. In some embodiments, the liquid composition is suitable for oral delivery. In some embodiments, the liquid composition is in the form of an oral dosage form.

In one aspect, the present disclosure relates to a kit comprising: (i) a first container comprising lamotrigine, a lamotrigine salt or co-crystal, or a hydrate or solvate thereof, or a pharmaceutical composition comprising lamotrigine, a lamotrigine salt or co-crystal, or hydrate or solvate thereof; and (ii) a second container comprising a vehicle.

In some embodiments, the first container comprises lamotrigine. In some embodiments, the first container comprises a lamotrigine salt or co-crystal, or a hydrate or solvate thereof. In some embodiments, the first container comprises a pharmaceutical composition comprising lamotrigine, a lamotrigine salt or co-crystal, or hydrate or solvate thereof, and at least one excipient.

In some embodiments, the contents in the first container are in the form of a powder. In some embodiments, the powder has a particle size that is suitable for passing through certain mesh, for example mesh 20, mesh 40, mesh 60, mesh 80, or mesh 100.

In some embodiments, the vehicle in the second container comprises water. In some embodiments, the vehicle in the second container comprises a pH adjuster. In some embodiments, the vehicle in the second container comprises a salting agent. In some embodiments, the vehicle in the second container comprises a suspending agent. In some embodiments, the vehicle in the second container comprises a salting agent and a pH adjuster. In some embodiments, the vehicle in the second container comprises a salting agent, a pH adjuster, and a suspending agent.

In some embodiments, the second container comprises from about 10 mL to about 500 mL of the vehicle. In some embodiments, the second container comprises from about 25 mL to about 400 mL of the vehicle. In some embodiments, the second container comprises about 25 mL of the vehicle, about 50 mL of the vehicle, about 75 mL of the vehicle, about 100 mL of the vehicle, about 125 mL of the vehicle, about 150 mL of the vehicle, about 175 mL of the vehicle, about 200 mL of the vehicle, about 225 mL of the vehicle, about 250 mL of the vehicle, about 275 mL of the vehicle, about 300 mL of the vehicle, about 325 mL of the vehicle, about 350 mL of the vehicle, about 375 mL of the vehicle, or about 400 mL of the vehicle. In some embodiments, the second container comprises about 50 mL of the vehicle. In some embodiments, the second container comprises about 100 mL of the vehicle. In some embodiments, the second container comprises about 200 mL of the vehicle. In some embodiments, the second container comprises about 300 mL of the vehicle.

In some embodiments, the kit further comprises a tool for scraping the contents in the first container into the vehicle in the second container or for scraping the vehicle in the second container into the contents in the first container.

In some embodiments, when the contents of the first container are combined with the vehicle in the second container, the resultant combination is in the form of a suspension.

In some embodiments, the resultant combination comprises a lamotrigine fumarate salt, for example, a lamotrigine hemifumarate anhydrate.

In some embodiments, the resultant combination comprises from about 5 mg/ml to about 50 mg/mL of lamotrigine or a salt or co-crystal thereof, or a hydrate or solvate thereof. In some embodiments, the resultant combination comprises about 5 mg/mL of lamotrigine or a salt or co-crystal thereof, or a hydrate or solvate thereof. In some embodiments, the resultant combination comprises about 25 mg/mL of lamotrigine or a salt or co-crystal thereof, or a hydrate or solvate thereof. In some embodiments, the resultant combination comprises about 50 mg/mL of lamotrigine or a salt or co-crystal thereof, or a hydrate or solvate thereof.

In some embodiments, the resultant combination comprises an amount of lamotrigine or a salt or co-crystal thereof, or a hydrate or solvate thereof, that is equivalent to from about 5 mg/mL to about 50 mg/mL of lamotrigine (free base). In some embodiments, the resultant combination comprises an amount of lamotrigine or a salt or co-crystal thereof, or a hydrate or solvate thereof, that is equivalent to about 5 mg/mL of lamotrigine (free base). In some embodiments, the resultant combination comprises an amount of lamotrigine or a salt or co-crystal thereof, or a hydrate or solvate thereof, that is equivalent to about 25 mg/ml of lamotrigine (free base). In some embodiments, the resultant combination comprises an amount of lamotrigine or a salt or co-crystal thereof, or a hydrate or solvate thereof, that is equivalent to about 50 mg/mL of lamotrigine (free base).

In some embodiments, the resultant combination is stable. In some embodiments, the resultant combination is stable after being stored at about 5° C., at about room temperature, at about 40° C., or after being subjected to accelerated stability conditions for a period time, for example, for about 6 months or about 24 months. In some embodiments, the resultant combination comprises less than about 1% solubilized lamotrigine (free base).

In some embodiments, the resultant combination has a pH of from about 3.0 to about 5.0, for example, from about 3.6 to about 4.8, from about 3.6 to about 4.6, from about 3.6 to about 4.1, from about 3.6 to about 4.0, from about 3.6 to about 4.1, from about 4.0 to about 4.5, from about 4.0 to about 4.1, or from about 4.3 to about 5.0.

In some embodiments, the resultant combination is any of the compositions described herein.

In another aspect, the present disclosure relates to methods of treating a disease or condition using a pharmaceutical composition disclosed herein. Examples of the disease or condition include epilepsy, bipolar disorder (e.g. of bipolar I disorder and bipolar II disorder), depression, and neurofibromatosis. Examples of epilepsy include tonic-clonic seizures (includes simple partial, complex partial and secondarily generalized seizures). As such, a pharmaceutical composition disclosed herein may be useful as an adjunctive therapy for the following seizure types in patents with epilepsy: partial on-set seizures, primary generalized tonic-clonic (PGTC) seizures; and/or generalized seizures of Lennox-Gastaut syndrome. In addition, a pharmaceutical composition disclosed herein may also be useful for conversion to monotherapy in subjects with partial-onset seizures who are receiving treatment with a single antiepileptic drug (AED), such as carbamazepine, phenytoin, phenobarbital, primidone, or valproate. Further, a pharmaceutical composition as disclosed herein may also be useful for the maintenance treatment of bipolar I disorder to delay the time to occurrence of mood episodes (depression, mania, hypomania, mixed episodes) in patients treated for acute mood episodes with standard therapy.

In some embodiments, the pharmaceutical composition disclosed herein is an adjuvant therapy in partial seizures (e.g., focal onset tonic-clonic, atypical absence, myoclonic, and due to Lennox-Gastaut syndrome). In some embodiments, the pharmaceutical composition disclosed herein is an alternative therapy for absence seizure and atypical absence, myoclonic, and atonic seizures. Other exemplary applications include treatment of peripheral neuropathy, trigeminal neuralgia, cluster headaches, migraines, and neuropathic pain.

In some embodiments, the present disclosure relates to methods of treating epilepsy using pharmaceutical composition disclosed herein. In some embodiments, the treatment is used as a monotherapy. In some embodiments, the treatment is used as an adjunctive therapy.

In some embodiments, the method of treating a subject with epilepsy comprises administering to a subject in need thereof a pharmaceutical composition as disclosed herein. In some embodiments, the method of treating a subject with epilepsy comprises combining the first container and the second container in a kit as disclosed herein and administering the resultant combination to the subject.

In some embodiments, the pharmaceutical composition or resultant combination is used as a monotherapy. In some embodiments, the monotherapy is for subjects aged about 16 years or older. In some embodiments, the monotherapy is for subjects suffering from partial-onset seizures. In some embodiments, the subjects with partial-onset seizures are or were receiving treatment with another antiepileptic drug (such as, for example, carbamazepine, phenytoin, phenobarbital, primidone, or valproate).

In some embodiments, the pharmaceutical composition or resultant combination is used as an adjunctive therapy. In some embodiments, the adjunctive therapy is for subjects aged about 2 years or older. In some embodiments, the adjunctive therapy is for subjects suffering from partial-onset seizures. In some embodiments, the adjunctive therapy is for subjects suffering from primary generalized tonic-clonic seizures. In some embodiments, the adjunctive therapy is for subjects suffering from generalized seizures of Lennox-Gastaut syndrome. When referring to a subject suffering from seizures and the like, it should be understood that even a single seizure is enough to consider a subject to be “a subject suffering from seizures.”

In some embodiments, the present disclosure relates to methods of treating bipolar disorder using pharmaceutical composition disclosed herein.

In some embodiments, the method of treating a subject with bipolar disorder comprises administering to a subject in need thereof a pharmaceutical composition as disclosed herein. In some embodiments, the method of treating a subject with bipolar disorder comprises combining the first container and the second container in a kit as disclosed herein and administering the resultant combination to the subject.

In some embodiments, the pharmaceutical composition or resultant combination is used as a maintenance treatment of a bipolar disorder, such as bipolar I disorder. In some embodiments, the pharmaceutical composition or resultant combination is used as a maintenance treatment of bipolar I disorder to delay the time to occurrence of mood episodes in subjects treated for acute mood episodes with standard therapy.

In some embodiments, the present disclosure relates to methods of treating a disease or condition using a pharmaceutical composition disclosed herein, wherein the disease or condition is selected from partial on-set seizures, primary generalized tonic-clonic seizures, generalized seizures of Lennox-Gastaut syndrome, bipolar I disorder, acute mood episodes, acute manic episodes, and mixed mood episodes.

In some embodiments, in any of the methods disclosed herein, the subject self-administers the lamotrigine salt or co-crystal, or a hydrate or solvate thereof, or the pharmaceutical composition, or the resultant combination from the kit.

In some embodiments, in any of the methods disclosed herein, someone other than the subject administers the lamotrigine salt or co-crystal, or a hydrate or solvate thereof, or the pharmaceutical composition, or the resultant combination from the kit to the subject.

In some embodiments, the lamotrigine salt or co-crystal, or a hydrate or solvate thereof, or the pharmaceutical composition, or the resultant combination is administered in a dose of from about 1 mg to about 1000 mg of lamotrigine (free base) per day. In some embodiments, the dose is from about 1 mg to about 700 mg of lamotrigine (free base) per day. In some embodiments, the dose is from about 1 mg to about 500 mg of lamotrigine (free base) per day.

In some embodiments, the lamotrigine salt or co-crystal, or a hydrate or solvate thereof, or the pharmaceutical composition, or the resultant combination is administered in a dose of from about 25 mg to about 700 mg of lamotrigine (free base) per day.

In some embodiments, the lamotrigine salt or co-crystal, or a hydrate or solvate thereof, or the pharmaceutical composition, or the resultant combination is administered in a dose of from about 100 mg to about 200 mg of lamotrigine (free base) per day.

In some embodiments, the lamotrigine salt or co-crystal, or a hydrate or solvate thereof, or the pharmaceutical composition, or the resultant combination is administered in a dose of from about 100 mg to about 400 mg of lamotrigine (free base) per day.

In some embodiments, the lamotrigine salt or co-crystal, or a hydrate or solvate thereof, or the pharmaceutical composition, or the resultant combination is administered in a dose of from about 225 mg to about 375 mg of lamotrigine (free base) per day.

In some embodiments, the lamotrigine salt or co-crystal, or a hydrate or solvate thereof, or the pharmaceutical composition, or the resultant combination is administered in a dose of from about 300 mg to about 500 mg of lamotrigine (free base) per day.

These In some embodiments, the lamotrigine salt or co-crystal, or a hydrate or solvate thereof, or the pharmaceutical composition, or the resultant combination is administered in a dose of about 25 mg of lamotrigine (free base) every other day. In some embodiments, the dose is about 50 mg of lamotrigine (free base) per day. In some embodiments, the dose is about 100 mg of lamotrigine (free base) per day. In some embodiments, the dose is about 150 mg of lamotrigine (free base) per day. In some embodiments, the dose is about 200 mg of lamotrigine (free base) per day. In some embodiments, the dose is about 250 mg of lamotrigine (free base) per day. In some embodiments, the dose is about 300 mg of lamotrigine (free base) per day. In some embodiments, the dose is about 350 mg of lamotrigine (free base) per day. In some embodiments, the dose is about 400 mg of lamotrigine (free base) per day. In some embodiments, the dose is about 450 mg of lamotrigine (free base) per day. In some embodiments, the dose is about 500 mg of lamotrigine (free base) per day. In some embodiments, the dose is about 550 mg of lamotrigine (free base) per day. In some embodiments, the dose is about 600 mg of lamotrigine (free base) per day. In some embodiments, the dose is about 650 mg of lamotrigine (free base) per day. In some embodiments, the dose is about 700 mg of lamotrigine (free base) per day.

In some embodiments, the lamotrigine salt or co-crystal, or a hydrate or solvate thereof, or the pharmaceutical composition, or the resultant combination is administered in a dose of from about 1 mg to about 10 mg of lamotrigine (free base) per day. In some embodiments, the dose is about 2 mg of lamotrigine (free base) per day or every other day. In some embodiments, the dose is about 3 mg of lamotrigine (free base) per day or every other day. In some embodiments, the dose is about 4 mg of lamotrigine (free base) per day. In some embodiments, the dose is about 5 mg of lamotrigine (free base) per day. In some embodiments, the dose is about 6 mg of lamotrigine (free base) per day or every other day. In some embodiments, the dose is about 7 mg of lamotrigine (free base) per day or every other day. In some embodiments, the dose is about 8 mg of lamotrigine (free base) per day. In some embodiments, the dose is about 9 mg of lamotrigine (free base) per day or every other day. In some embodiments, the dose is about 10 mg of lamotrigine (free base) per day.

In some embodiments, the lamotrigine salt or co-crystal, or a hydrate or solvate thereof, or the pharmaceutical composition, or the resultant combination is administered in a dose of from about 0.10 mg to about 25 mg of lamotrigine (free base) per kilogram of the subject's weight per day. In some embodiments, the dose is from about 0.15 mg to about 15 mg of lamotrigine (free base) per kilogram of the subject's weight per day. In some embodiments, the dose is from about 0.3 mg to about 3.0 mg of lamotrigine (free base) per kilogram of the subject's weight per day.

In some embodiments, the lamotrigine salt or co-crystal, or a hydrate or solvate thereof, or the pharmaceutical composition, or the resultant combination is administered in a dose of about 0.15 mg of lamotrigine (free base) per kilogram of the subject's weight per day. In some embodiments, the dose is about 0.30 mg of lamotrigine (free base) per kilogram of the subject's weight per day. In some embodiments, the dose is about 0.60 mg of lamotrigine (free base) per kilogram of the subject's weight per day. In some embodiments, the dose is about 1.20 mg of lamotrigine (free base) per kilogram of the subject's weight per day.

In some embodiments, the lamotrigine salt or co-crystal, or a hydrate or solvate thereof, or the pharmaceutical composition, or the resultant combination is administered in a dose of from about 1 mg to about 15 mg of lamotrigine (free base) per kilogram of the subject's weight per day. In some embodiments, the dose is from about 1 mg to about 5 mg of lamotrigine (free base) per kilogram of the subject's weight per day. In some embodiments, the dose is from about 1 mg to about 3 mg of lamotrigine (free base) per kilogram of the subject's weight per day. In some embodiments, the dose is from about 4.5 mg to about 7.5 mg of lamotrigine (free base) per kilogram of the subject's weight per day. In some embodiments, the dose is from about 5 mg to about 15 mg of lamotrigine (free base) per kilogram of the subject's weight per day.

ENUMERATED EMBODIMENTS

Embodiment 1. A crystalline form of a lamotrigine salt selected from a lamotrigine dicarboxylic acid salt, and hydrates and solvates thereof.

Embodiment 2. A crystalline form of lamotrigine and a dicarboxylic acid, wherein the crystalline form is selected from a co-crystal of lamotrigine and the dicarboxylic acid, and hydrates and solvates thereof.

Embodiment 3. The crystalline form of embodiment 1 or 2, wherein the dicarboxylic acid is fumaric acid.

Embodiment 4. The crystalline form of embodiment 1 or 3, wherein the lamotrigine salt is selected from a lamotrigine monofumarate, a lamotrigine hemifumarate, a lamotrigine difumarate, and hydrates and solvates thereof.

Embodiment 5. The crystalline form of the immediately preceding embodiment, wherein the lamotrigine salt is selected from a lamotrigine hemifumarate anhydrate, a lamotrigine hemifumarate solvate, and a lamotrigine hemifumarate hydrate.

Embodiment 6. The crystalline form of the immediately preceding embodiment, wherein the lamotrigine salt is a lamotrigine hemifumarate anhydrate.

Embodiment 7. The crystalline form of the immediately preceding embodiment, wherein the stoichiometry of the lamotrigine hemifumarate anhydrate is in a range from about 0.50:1 fumarate/lamotrigine to about 0.99:1 fumarate/lamotrigine.

Embodiment 8. The crystalline form of the immediately preceding embodiment, wherein the stoichiometry of the lamotrigine hemifumarate anhydrate is in a range from about 0.50:1 fumarate/lamotrigine to about 0.60:1 fumarate/lamotrigine.

Embodiment 9. The crystalline form of any one of embodiments 5-7, wherein the lamotrigine hemifumarate anhydrate has a powder x-ray diffraction pattern comprising one or more peaks at about 7.0° 2θ, about 13.4° 2θ, about 14.1° 2θ, about 15.1° 2θ, about 17.5° 2θ, about 22.1° 2θ, and about 24.9° 2θ.

Embodiment 10. The crystalline form of any one of embodiments 5-8, wherein the lamotrigine hemifumarate anhydrate has a powder x-ray diffraction pattern comprising two or more peaks at about 7.0° 2θ, about 11.7° 2θ, about 12.4° 2θ, about 13.4° 2θ, about 14.1° 2θ, about 15.1° 2θ, about 16.5° 2θ, about 16.9° 2θ, about 17.5° 2θ, about 19.0° 2θ, about 19.3° 2θ, about 19.9° 2θ, about 20.0° 2θ, about 20.3° 2θ, about 21.3° 2θ, about 21.4° 2θ, about 22.1° 2θ, about 23.1° 2θ, about 23.8° 2θ, about 24.9° 2θ, about 25.7° 2θ, about 26.1° 2θ, about 26.6° 2θ, about 26.9° 2θ, about 27.7° 2θ, about 28.4° 2θ, about 28.9° 2θ, about 29.5° 2θ, and about 29.9° 2θ.

Embodiment 11. The crystalline form of any one of embodiments 5-10, wherein the lamotrigine hemifumarate anhydrate is characterized by a differential scanning calorimetry DSC thermogram with an endothermic peak at about 273° C.

Embodiment 12. The crystalline form of any one of embodiments 5-11, wherein the lamotrigine hemifumarate anhydrate has a powder x-ray diffraction pattern substantially the same as in FIG. 1.

Embodiment 13. The crystalline form of any one of embodiments 5-12, wherein the lamotrigine hemifumarate anhydrate which has a melt onset near 272° C. as measured by differential scanning calorimetry.

Embodiment 14. The crystalline form of any one of embodiments 5-13, wherein the lamotrigine hemifumarate anhydrate has a differential scanning calorimetry thermogram substantially the same as in FIG. 7.

Embodiment 15. The crystalline form of any one of embodiments 5-14, wherein the lamotrigine hemifumarate anhydrate has a Fourier-transform infrared spectroscopy spectrum substantially the same as in FIG. 3.

Embodiment 16. The crystalline form of any one of the preceding embodiments, wherein said crystalline form has one or more properties selected from:

a) greater solubility in an aqueous solvent or solvents as compared to lamotrigine;

b) an increased blood concentration as compared to lamotrigine when administered to a subject;

c) an improved absorption and pharmacokinetic (PK) profile as compared to lamotrigine when administered to a subject;

an increased rate of dissolution as compared to lamotrigine; and d) a sustained release profile as compared to lamotrigine when administered to a subject.

Embodiment 17. A pharmaceutical composition comprising a crystalline form of any one of the preceding embodiments and at least one pharmaceutically acceptable excipient.

Embodiment 18. The pharmaceutical composition of the immediately preceding embodiment, wherein the composition is a solid.

Embodiment 19. The pharmaceutical composition according to embodiment 17 or 18, wherein the composition is in the form of a powder.

Embodiment 20. The pharmaceutical composition of any one of embodiments 17-19, wherein the composition is suitable for reconstitution in a pharmaceutically acceptable carrier.

Embodiment 21. The pharmaceutical composition of any one of embodiments 17-20, wherein the at least one pharmaceutically acceptable excipient is selected from: a salting agent; a pH adjuster; a suspending agent; a preservative; a sweetener; an antifoaming agent; an anti-caking agent; and any combination thereof.

Embodiment 22. The pharmaceutical composition of embodiment 21, wherein the salting agent is fumaric acid or disodium fumarate.

Embodiment 23. The pharmaceutical composition of embodiment 21 or 22, wherein the pH adjuster is selected from sodium hydroxide, hydrochloric acid, phosphoric acid, disodium fumarate, and any combination thereof.

Embodiment 24. The pharmaceutical composition of any one of embodiments 21-23, wherein the suspending agent is selected from hydroxyethyl cellulose, hydroxypropyl methylcellulose, xanthan gum, microcrystalline cellulose, sodium carboxymethyl cellulose, and any combination thereof.

Embodiment 25. The pharmaceutical composition of any one of embodiments 21-24, wherein the preservative is selected from sodium benzoate and benzyl alcohol.

Embodiment 26. The pharmaceutical composition of any one of embodiments 21-25, wherein the sweetener is selected from sucralose, glucose, sorbitol, aspartame, saccharin sodium, and any combination thereof.

Embodiment 27. The pharmaceutical composition of any one of embodiments 21-26, wherein the antifoaming agent is a simethicone emulsion.

Embodiment 28. The pharmaceutical composition of any one of embodiments 21-27, wherein the anti-caking agent is silicon dioxide.

Embodiment 29. The pharmaceutical composition of any one of embodiments 20-28, wherein the pharmaceutically acceptable carrier is water.

Embodiment 30. A kit comprising:

a first container comprising crystalline form of any one of embodiments 1-16 or a pharmaceutical composition of any one of embodiments 17-28; and a second container comprising a vehicle.

Embodiment 31. The kit of the immediately preceding embodiment, wherein the crystalline form or composition in the first container is in the form of a powder.

Embodiment 32. The kit of embodiment 30 or 31, wherein the vehicle in the second container comprises water.

Embodiment 33. The kit of any one of embodiments 30-32, wherein the vehicle in the second container further comprises a pH adjuster.

Embodiment 34. The kit of any one of embodiments 30-33, wherein the kit further comprises a tool for scraping the crystalline form or composition in the first container into the vehicle in the second container.

Embodiment 35. A pharmaceutical composition comprising lamotrigine or a salt or co-crystal thereof, or a hydrate or solvate thereof, wherein the composition is a liquid with a pH of from about 3.0 to about 5.0.

Embodiment 36. The pharmaceutical composition of the immediately preceding embodiment, wherein the pH is from about 3.0 to about 4.0.

Embodiment 37. The pharmaceutical composition of embodiment 35, wherein the pH is from about 4.5 to about 5.0.

Embodiment 38. A pharmaceutical composition comprising from about 5 mg/ml to about 50 mg/mL of lamotrigine or a salt or co-crystal thereof, or a hydrate or solvate thereof, wherein the composition is in the form of a liquid.

Embodiment 39. A pharmaceutical composition comprising lamotrigine or a salt or co-crystal thereof, or a hydrate or solvate thereof, wherein the composition is a liquid and the amount of lamotrigine or salt or co-crystal thereof, or a hydrate or solvate thereof, in the liquid is stable for about 6 months or more (for example, for about 24 months).

Embodiment 40. The pharmaceutical composition of any one of embodiments 35-37 or 39, wherein the composition comprises from about 5 mg/mL to about 50 mg/mL lamotrigine or a salt or co-crystal thereof, or a hydrate or solvate thereof.

Embodiment 41. The pharmaceutical composition of any one of embodiments 35-40, wherein the composition comprises from about 5 mg/mL to about 25 mg/mL lamotrigine or a salt or co-crystal thereof, or a hydrate or solvate thereof.

Embodiment 42. The pharmaceutical composition of the immediately preceding embodiment, wherein the composition comprises about 5 mg/mL lamotrigine or a salt or co-crystal thereof, or a hydrate or solvate thereof.

Embodiment 43. The pharmaceutical composition of embodiment 41, wherein the composition comprises about 25 mg/mL lamotrigine or a salt or co-crystal thereof, or a hydrate or solvate thereof.

Embodiment 44. The pharmaceutical composition of any one of embodiments 35-43, wherein the composition comprises lamotrigine.

Embodiment 45. The pharmaceutical composition of any one of embodiments 35-43, wherein the composition comprises a salt or co-crystal of lamotrigine, or a hydrate or solvate thereof.

Embodiment 46. The pharmaceutical composition of any one of embodiments 35-45, wherein the composition comprises lamotrigine and a salt or co-crystal of lamotrigine, or a hydrate or solvate thereof.

Embodiment 47. The pharmaceutical composition of any one of embodiments 35-43 or 45-46, wherein the salt of lamotrigine is a fumarate salt.

Embodiment 48. The pharmaceutical composition of the immediately preceding embodiment, wherein the salt of lamotrigine is a hemifumarate salt.

Embodiment 49. The pharmaceutical composition of the immediately preceding embodiment, wherein the hemifumarate salt is a hemifumarate anhydrate.

Embodiment 50. The pharmaceutical composition of the immediately preceding embodiment, wherein the stoichiometry of the lamotrigine hemifumarate anhydrate is in a range from 0.5:1 fumarate/lamotrigine to about 0.99:1 fumarate/lamotrigine.

Embodiment 51. A pharmaceutical composition comprising a salt or co-crystal of lamotrigine, or a hydrate or solvate thereof, wherein the composition is in the form of a liquid.

Embodiment 52. The pharmaceutical composition of the immediately preceding embodiment, wherein the salt of lamotrigine is a fumarate salt.

Embodiment 53. The pharmaceutical composition of the immediately preceding embodiment, wherein the salt of lamotrigine is a hemifumarate salt.

Embodiment 54. The pharmaceutical composition of the immediately preceding embodiment, wherein the hemifumarate salt is a hemifumarate anhydrate.

Embodiment 55. The pharmaceutical composition of the immediately preceding embodiment, wherein the stoichiometry of the lamotrigine hemifumarate anhydrate is in a range from about 0.5:1 fumarate/lamotrigine to about 0.99:1 fumarate/lamotrigine.

Embodiment 56. The pharmaceutical composition of any one of embodiments 51-55, wherein the composition comprises further comprises lamotrigine.

Embodiment 57. The pharmaceutical composition of any one of embodiments 35-50 and 56, wherein the amount of solubilized lamotrigine is less than about 1%.

Embodiment 58. A pharmaceutical composition comprising lamotrigine and a salting agent wherein the composition is in the form of a liquid.

Embodiment 59. The pharmaceutical composition of the immediately preceding embodiment, wherein the composition comprises from about 5 mg/mL to about 50 mg/ml lamotrigine or a salt or co-crystal thereof, or a hydrate or solvate thereof.

Embodiment 60. The pharmaceutical composition of the immediately preceding embodiment, wherein the composition comprises from about 5 mg/mL to about 25 mg/ml lamotrigine or a salt or co-crystal thereof, or a hydrate or solvate thereof.

Embodiment 61. The pharmaceutical composition of the immediately preceding embodiment, wherein the composition comprises about 5 mg/mL lamotrigine or a salt or co-crystal thereof, or a hydrate or solvate thereof.

Embodiment 62. The pharmaceutical composition of embodiment 60, wherein the composition comprises about 25 mg/mL lamotrigine or a salt or co-crystal thereof, or a hydrate or solvate thereof.

Embodiment 63. The pharmaceutical composition of any one of embodiments 58-62, wherein the composition further comprises a salt or co-crystal of lamotrigine, or a hydrate or solvate thereof.

Embodiment 64. The pharmaceutical composition of the immediately preceding embodiment, wherein the salt of lamotrigine is a fumarate salt.

Embodiment 65. The pharmaceutical composition of the immediately preceding embodiment, wherein the salt of lamotrigine is a hemifumarate salt.

Embodiment 66. The pharmaceutical composition of the immediately preceding embodiment, wherein the hemifumarate salt is a hemifumarate anhydrate.

Embodiment 67. The pharmaceutical composition of the immediately preceding embodiment, wherein the stoichiometry of the lamotrigine hemifumarate anhydrate is in a range from about 0.50:1 fumarate/lamotrigine to about 0.99:1 fumarate/lamotrigine.

Embodiment 68. The pharmaceutical composition of any one of embodiments 17, 21-29, and 35-67, wherein the amount of solubilized lamotrigine is less than about 1%.

Embodiment 69. The pharmaceutical composition of any one of embodiments 17, 21-29, and 38-68, wherein the pH is from about 3.0 to about 5.0.

Embodiment 70. The pharmaceutical composition of the immediately preceding embodiment, wherein the pH is from about 3.5 to about 5.0.

Embodiment 71. The pharmaceutical composition of embodiment 70, wherein the pH is from about 3.6 to about 4.8.

Embodiment 72. The pharmaceutical composition of any one of embodiments 17, 21-29, and 35-71, wherein the composition is in the form of a suspension.

Embodiment 73. The pharmaceutical composition of any one of embodiments 35-72, wherein the composition further comprises an excipient selected from a pH adjuster; a suspending agent; a preservative; a sweetener; an antifoaming agent; an anti-caking agent; a pharmaceutically acceptable carrier; and any combination thereof.

Embodiment 74. The pharmaceutical composition of the immediately preceding embodiment, wherein the suspending agent is selected from hydroxyethyl cellulose, hydroxypropyl methylcellulose, xanthan gum, microcrystalline cellulose, sodium carboxymethyl cellulose, and any combination thereof.

Embodiment 75. The pharmaceutical composition of embodiment 73 or 74, wherein the preservative is selected from sodium benzoate and benzyl alcohol.

Embodiment 76. The pharmaceutical composition of any one of embodiments 73-75, wherein the sweetener is selected from sucralose, glucose, sorbitol, aspartame, saccharin sodium, and any combination thereof.

Embodiment 77. The pharmaceutical composition of any one of embodiments 73-76, wherein the antifoaming agent is a simethicone emulsion.

Embodiment 78. The pharmaceutical composition of any one of embodiments 73-77, wherein the anti-caking agent is silicon dioxide.

Embodiment 79. The pharmaceutical composition of any one of embodiments 73-78, wherein the pharmaceutically acceptable carrier is water.

Embodiment 80. The pharmaceutical composition of any one of embodiments 35-79, wherein the composition further comprises a salting agent.

Embodiment 81. The pharmaceutical composition of any one of embodiments 35-80, wherein the salting agent is fumaric acid or disodium fumaric acid.

Embodiment 82. A kit comprising:

a first container comprising lamotrigine or a salt or co-crystal thereof, or a hydrate or solvate thereof, or a pharmaceutical composition of any one of embodiments 35-81; and a second container comprising a vehicle.

Embodiment 83. The kit of the immediately preceding embodiment, wherein the first container comprises lamotrigine or a salt or co-crystal thereof, or a hydrate or solvate thereof, which is in the form of a powder.

Embodiment 84. The kit of embodiment 30 or 31, wherein the vehicle in the second container comprises water.

Embodiment 85. The kit of any one of embodiments 30-32, wherein the vehicle in the second container further comprises a pH adjuster.

Embodiment 86. The kit of any one of embodiment 30 or 31, wherein the vehicle in the second container comprises a salting agent.

Embodiment 87. The kit of any one of embodiments 30-33, wherein the kit further comprises a tool for scraping the crystalline form or composition in the first container into the vehicle in the second container.

Embodiment 88. A method of treating a subject with epilepsy comprising administering to a subject in need thereof a crystalline form of any one of embodiments 1-16 or a pharmaceutical composition according to any one of embodiments 17-29 or 35-81.

Embodiment 89. A method of treating a subject with epilepsy, the method comprising combining the first container and the second container in a kit according to embodiments 30-34 or 82-87 and administering the resultant combination to the subject.

Embodiment 90. The method of embodiment 88 or 89, wherein the crystalline form, the pharmaceutical composition, or the resultant combination from the kit is used as a monotherapy.

Embodiment 91. The method of embodiment 90, wherein the subject suffers from partial-onset seizures.

Embodiment 92. The method of embodiment 88 or 89, wherein the crystalline form, the pharmaceutical composition, or the resultant combination from the kit is used as an adjunctive therapy.

Embodiment 93. The method of embodiment 92, wherein the subject suffers from partial-onset seizures, primary generalized tonic-clonic seizures, and/or generalized seizures of Lennox-Gastaut syndrome.

Embodiment 94. A method of treating a subject with bipolar disorder comprising administering to a subject in need thereof a crystalline form of any one of embodiments 1-16 or a pharmaceutical composition according to any one of embodiments 17-29 or 35-81.

Embodiment 95. A method of treating a subject with bipolar disorder, the method comprising combining the first container and the second container in a kit according to embodiments 30-34 or 82-87 and administering the resultant combination to the subject.

Embodiment 96. The method of embodiment 94 or 95, wherein the crystalline form, the pharmaceutical composition, or the resultant combination from the kit is used for maintenance treatment of bipolar I disorder.

Embodiment 97. The method of any one of embodiments 88-96, wherein the subject self-administers the crystalline form, the pharmaceutical composition, or the resultant combination from the kit.

Embodiment 98. The method of any one of embodiments 88-96, wherein someone other than the subject administers the crystalline form, the pharmaceutical composition, or the resultant combination from the kit to the subject.

Embodiment 99. The method of any one of embodiments 88-98, wherein a dose of from about 25 mg to about 700 mg of lamotrigine (free base) is administered per day.

Embodiment 100. The method of the immediately preceding embodiment, wherein a dose of about 200 mg, about 300 mg, about 400 mg, or about 500 mg of lamotrigine (free base) is administered per day or every other day.

Embodiment 101. The method of any one of embodiments 88-98, wherein a dose of from about 1 mg to about 15 mg of lamotrigine (free base) per kilogram of the subject's weight is administered per day.

Embodiment 102. The method of the immediately preceding embodiment, wherein a dose of about 5 mg of lamotrigine (free base) per kilogram of the subject's weight is administered per day or a dose of about 15 mg of lamotrigine (free base) per kilogram of the subject's weight is administered per day.

Embodiment 103. A liquid composition comprising from about 5 mg/mL to about 50 mg/mL of lamotrigine or a salt or co-crystal thereof, or a hydrate or solvate thereof.

Embodiment 104. The liquid composition according to embodiment 103, wherein the composition comprises about 5 mg/mL of lamotrigine or a salt or co-crystal thereof, or a hydrate or solvate thereof.

Embodiment 105. The liquid composition according to embodiment 103, wherein the composition comprises about 25 mg/mL of lamotrigine or a salt or co-crystal thereof, or a hydrate or solvate thereof.

Embodiment 106. The liquid composition according to any one of embodiments 103-105, wherein the composition comprises a salting agent.

Embodiment 107. The liquid composition according to any one of embodiments 103-106, wherein the composition comprises a suspending agent.

Embodiment 108. The liquid composition according to any one of embodiments 103-107, wherein the composition comprises a lamotrigine.

Embodiment 109. The liquid composition according to any one of embodiments 103-108, wherein the composition further comprises a lamotrigine fumarate.

Embodiment 110. The liquid composition according to the immediately preceding embodiment, wherein the lamotrigine fumarate is a lamotrigine hemifumarate anhydrate.

Embodiment 111. The liquid composition according to any one of embodiments 103-110, wherein the amount of solubilized lamotrigine in the composition is less than about 1%.

Embodiment 112. The liquid composition according to any one of embodiments 103-111, wherein the pH is from about 3.0 to about 5.0.

Embodiment 113. The liquid composition according to any one of embodiments 103-112, wherein the composition is stable for about six months after being stored at room temperature.

Embodiment 114. A liquid composition comprising lamotrigine and a salting agent.

Embodiment 115. The liquid composition according to embodiment 114, wherein the composition comprises a lamotrigine salt or co-crystal, or hydrate or solvate thereof.

Embodiment 116. The liquid composition according to embodiment 114 or 115, wherein the composition comprises an amount of lamotrigine or a salt or co-crystal thereof, or a hydrate or solvate thereof, that is equivalent to from about 5 mg/mL to about 50 mg/ml of lamotrigine (free base).

Embodiment 117. The liquid composition according to any one of embodiments 114-116, wherein the amount of solubilized lamotrigine in the composition is less than about 1%.

Embodiment 118. The liquid composition according to any one of embodiments 114-117, wherein the pH is from about 3.0 to about 5.0.

Embodiment 119. The liquid composition according to any one of embodiments 114-118, wherein the composition is stable for about six months after being stored at room temperature.

Embodiment 120. A method of treating a subject with a condition comprising administering to a subject in need thereof the pharmaceutical composition according to any one of embodiments 103-113, wherein the condition is selected from epilepsy and bipolar.

Embodiment 121. A method of treating a subject with a condition comprising administering to a subject in need thereof the pharmaceutical composition according to any one of embodiments 114-120, wherein the condition is selected from epilepsy and bipolar.

Embodiment 122. A crystalline form selected from: (i) a lamotrigine dicarboxylic acid salt, and hydrates and solvates thereof, and (ii) a co-crystal of lamotrigine and the dicarboxylic acid, and hydrates and solvates thereof.

Embodiment 123. The crystalline form of embodiment 122, wherein the lamotrigine salt is selected from a lamotrigine monofumarate, a lamotrigine hemifumarate, a lamotrigine difumarate, and hydrates and solvates thereof.

Embodiment 124. The crystalline form of the immediately preceding embodiment, wherein the lamotrigine hemifumarate is a lamotrigine hemifumarate anhydrate.

Embodiment 125. The crystalline form of the immediately preceding embodiment, wherein the lamotrigine hemifumarate anhydrate has an x-ray powder diffraction pattern comprising one or more peaks at about 7.0° 2θ, about 13.4° 2θ, about 14.1° 2θ, about 15.1° 2θ, about 17.5° 2θ, about 22.1° 2θ, and about 24.9° 2θ.

Embodiment 126. A kit comprising: a first container comprising lamotrigine or a salt or co-crystal thereof, or a hydrate or solvate thereof; and a second container comprising a vehicle and a salting agent.

EXAMPLES

Example 1. Preparation and Characterization of Lamotrigine Hemifumarate Anhydrate Lamotrigine (7.5 g) and fumaric acid (1.98 g) were added to 240 mL of purified water. The mixture was stirred with an overhead impeller stirrer for one hour. The overhead stirrer was replaced with an overhead homogenizer, and homogenization was initiated while the pH was adjusted to approximately 4 with 0.84 g of 5N sodium hydroxide (NaOH). The homogenizer was removed, and the solution was stirred for another hour. The resultant suspension was vacuum filtered through a 0.45 μm filter to collect the solids. The solids were dried in a desiccator at room temperature and studied using various analytical methods (see Table 1A and analytical methods example below).

The collected solid material was characterized by X-ray powder diffraction (XRPD) and solution $^1$H NMR was conducted to confirm its chemical identity and stoichiometry. The solid form was also characterized by FT-IR and Raman microscopy. Thermogravimetric analyses (TGA) and differential scanning calorimetry (DSC) were used to determine volatile content and melting point. Dynamic vapor sorption (DVS) with post-DVS X-ray powder diffraction (XRPD) analyses were also conducted to look for hygroscopicity and form-changes from exposure to moisture.

The material was identified as lamotrigine hemifumarate anhydrate (see Table 1A). The crystalline salt exhibited a 1:2 (acid/base) stoichiometry. The form was determined to be anhydrous and exhibited a melt onset with concomitant decomposition near 272° C. The form exhibited low hygroscopicity and remained unchanged by XRPD upon dynamically changing elevated humidity exposure at room temperature, indicating that it is physically stable within the timeframe evaluated.

The XRPD pattern of lamotrigine hemifumarate anhydrate was successfully indexed with a single unit cell which provides strong evidence that the pattern is representative of a single crystalline phase. Whole-pattern Pawley refinement was performed to accurately determine a tentative unit cell volume and cell parameters. The crystal system is monoclinic and the space group is P21/c (14) and provides cell parameters and a calculated volume as: a=12.828 Å, b=9.565 Å, c=10.971 Å, α=90°, β=101.836°, γ=90°, V=1317.6 Å3. With a formula weight of 314.13 g mol-1 and Z=4, the calculated density is 1.573 g cm-3. The observed peaks for XRPD pattern within the range of up to about 30° 2θ are shown in FIG. 1 and provided in Table 1B. The prominent peaks are provided in Table IC.

Based on the tentative indexing and refinement results, the unit cell contains four lamotrigine cations and two fumarate dianions. For the fumarate dianion to have an occupancy of 0.5 in the formula unit, it must be located at a crystallographic inversion center. The molecular volume of Lamotrigine Hemifumarate is estimated to be about 332 Å3 giving a total occupied unit cell volume of about 1327 Λ3. Consequently, no excess free volume remains for solvent or water, consistent with an anhydrous form.

Figure 2:
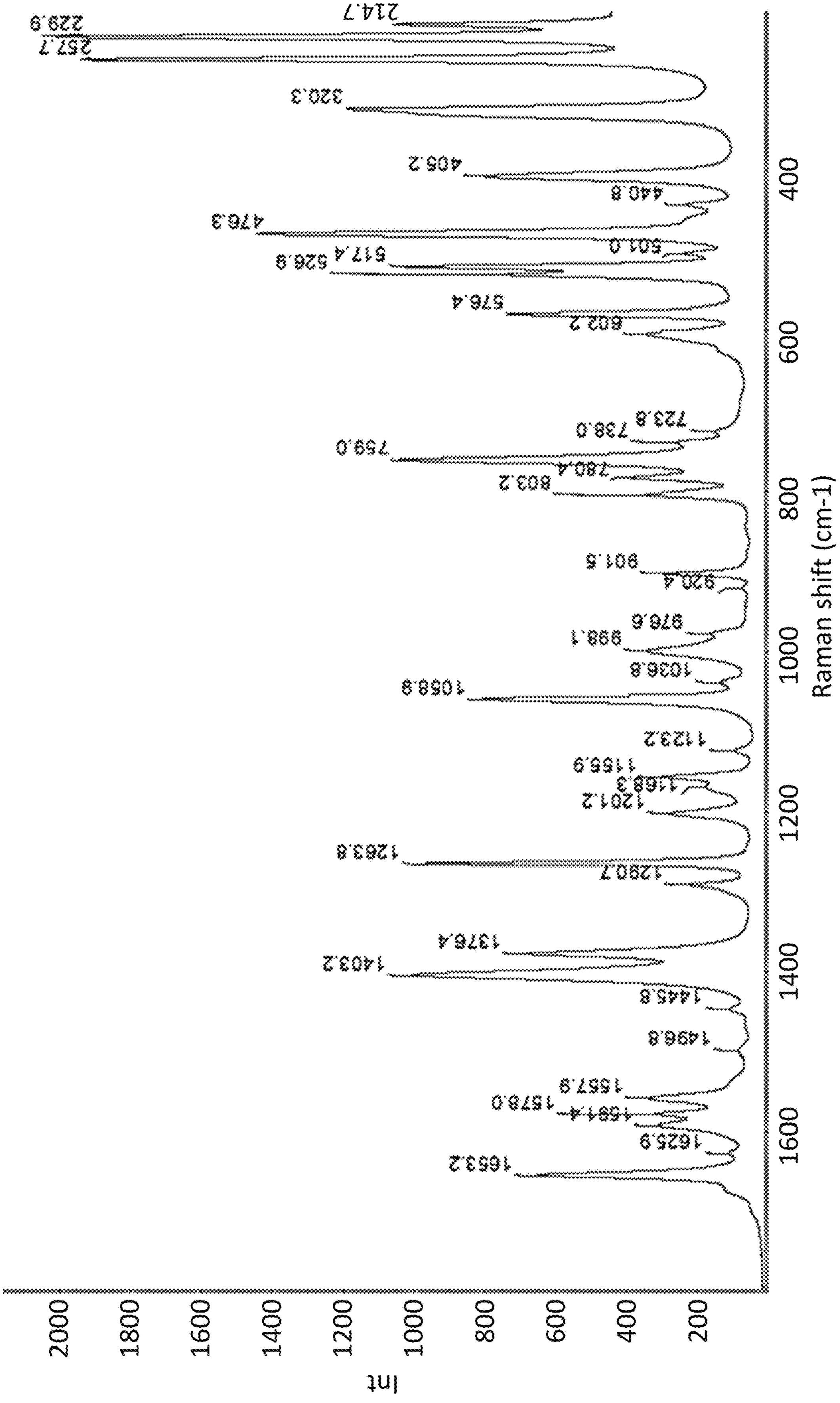
FIG. 2 shows a Raman spectrum of a lamotrigine hemifumarate anhydrate.

The Raman and FT-IR spectra are provided as orthogonal characterization techniques (FIG. 2 and FIG. 3, respectively). A reference spectrum of the lamotrigine free base can be found in the literature (see Ramya, T et al., "Structural and Qualitative Analysis of Lamotrigine", Int. *J. Neurorehabilitation Eng.* 1 (2014) 1-4). The Raman spectrum in FIG. 2 contains a strong peak at 1653 cm-1. This peak is not present in the lamotrigine free base spectrum and is likely due to the fumaric acid. Fumaric acid has a strong C═O stretch at 1685 cm-1. In FIG. 2, this peak has been shifted to 1653 cm-1. This shift is consistent with an interaction with another compound, such as lamotrigine. Literature reports for the infrared spectrum of the lamotrigine free base list the N—H stretch for the primary amine at 3448 cm-1 (see Chadha, R et al., "Multicomponent solids of lamotrigine with some selected coformers and their characterization by thermoanalytical, spectroscopic and X-ray diffraction methods", *Cryst Eng Comm.* 13 (2011) 6271-6284.). This peak is missing in the infrared spectrum in FIG. 3 (possibly shifted to 3321 cm-1), indicating that the amine NH moiety of lamotrigine is interacting with another compound (fumaric acid). Both Raman and infrared spectroscopy provide supportive evidence for the formulation of lamotrigine hemifumarate.

Figure 4:
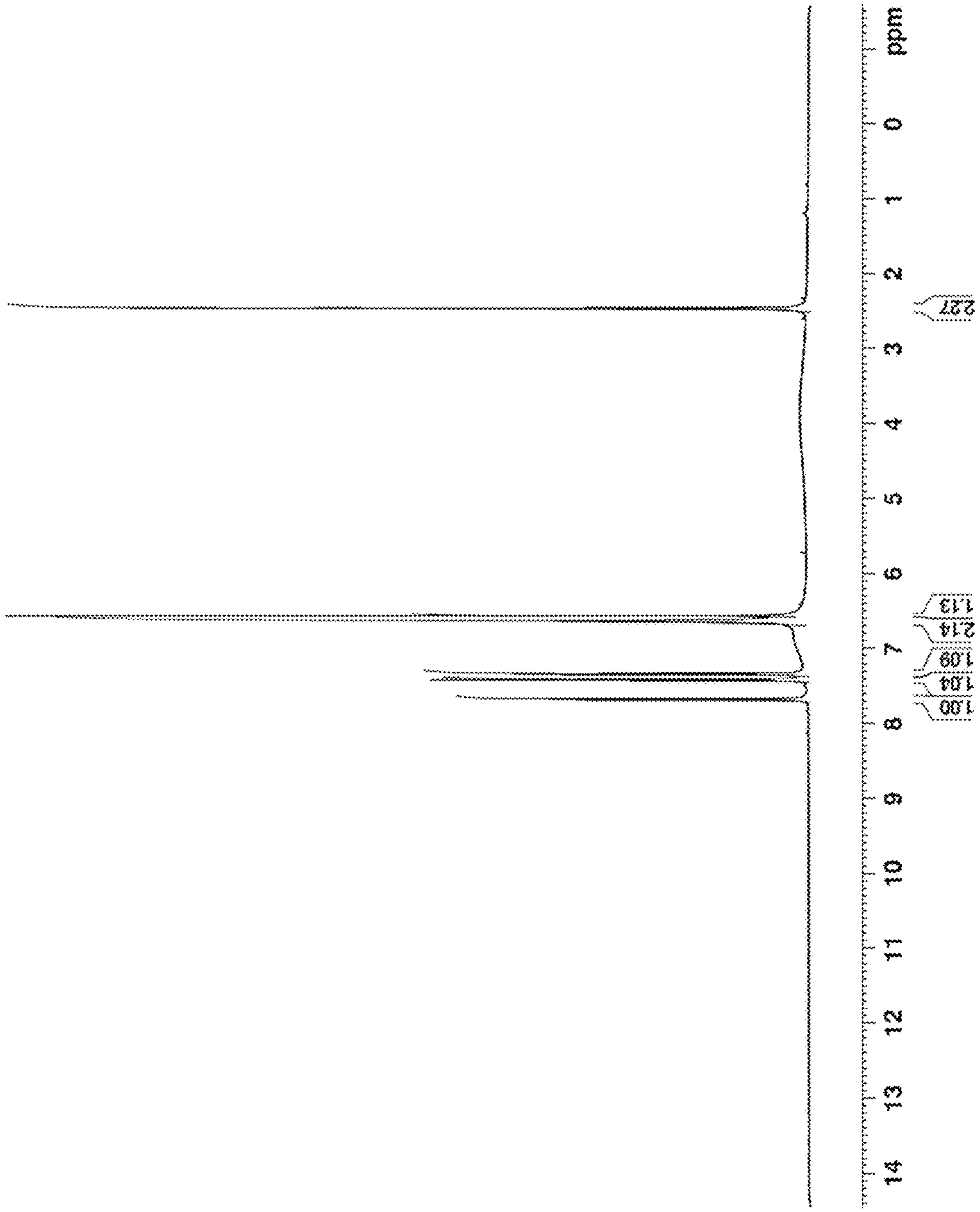
FIG. 4 shows a $^{1}H$ NMR spectrum of a lamotrigine hemifumarate anhydrate.
Figure 5A:
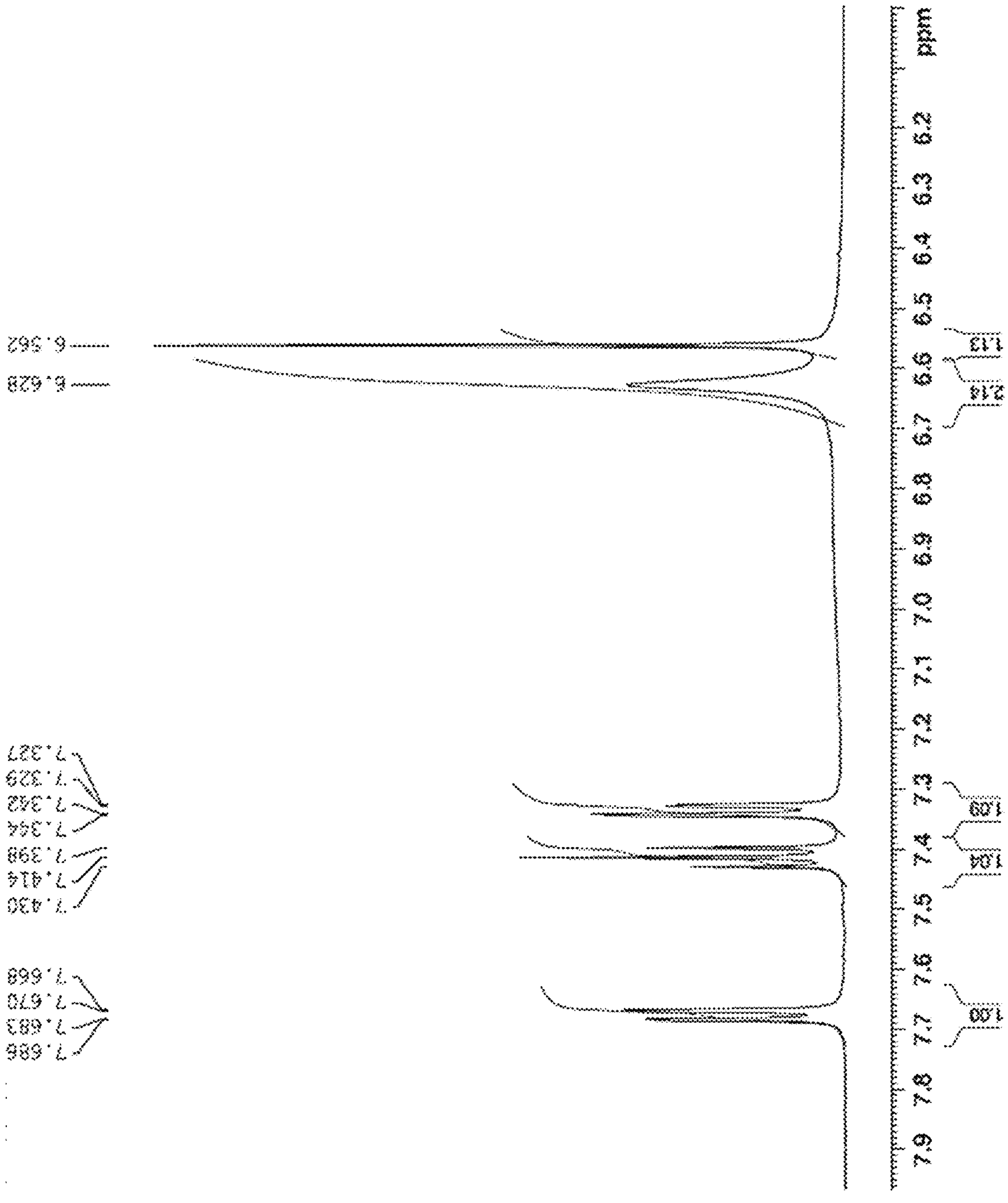
FIG. 5A shows the expanded $^{1}H$ NMR spectrum from FIG. 4 with proton magnetic resonance signal assignments.
Figures 5B, 5C:
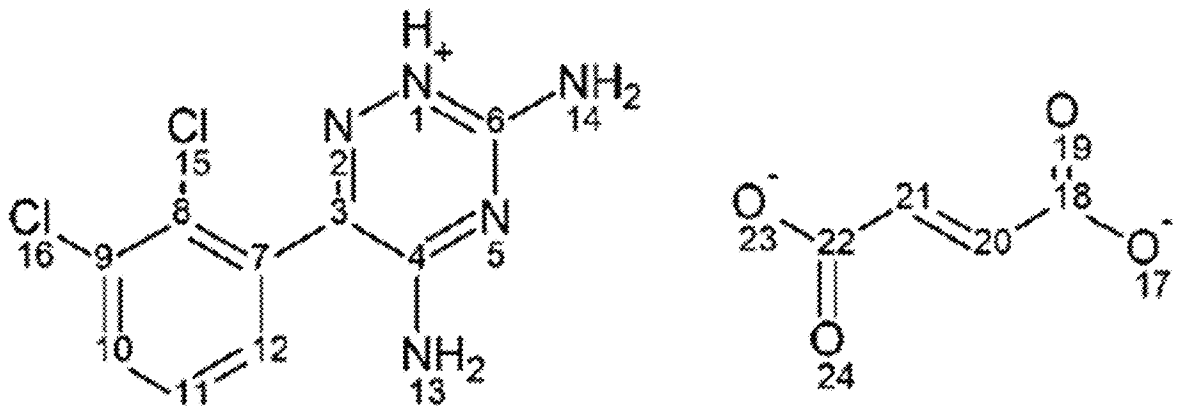
FIG. 5B shows the $^{1}H$ NMR spectroscopy data for lamotrigine hemifumarate anhydrate in DMSO-d6.
FIG. 5C shows the numbering in a lamotrigine hemifumarate, as it relates to the $^{1}H$ NMR spectroscopy data in FIG. 5B.

The obtained solution $^1$H NMR spectrum is shown in FIG. 4. FIG. 5 provides an enlarged spectrum along with assignments of proton magnetic resonance signals. The observed chemical shifts and apparent spin-spin couplings are in line with aromatic substitution on the ring and the known positions of the protons for lamotrigine, as documented in literature (see Beattie, K et al., Chapter 6—Lamotrigine. In *Profiles of Drug Substances, Excipients and Related Methodology*; Britain, H. G., Ed.; Academic Press, 2012; Vol. 37, pp. 245-285. https://doi.org/10.1016/b978-0-12-397220-0.00006-4). The one type of proton assigned to fumaric acid (6.56 ppm) has an integral value consistent with one-half mole equivalents (1:2 acid/base stoichiometry). Residual protons from the solvent DMSO-d6 are observed at 2.50 ppm.

Figure 6:
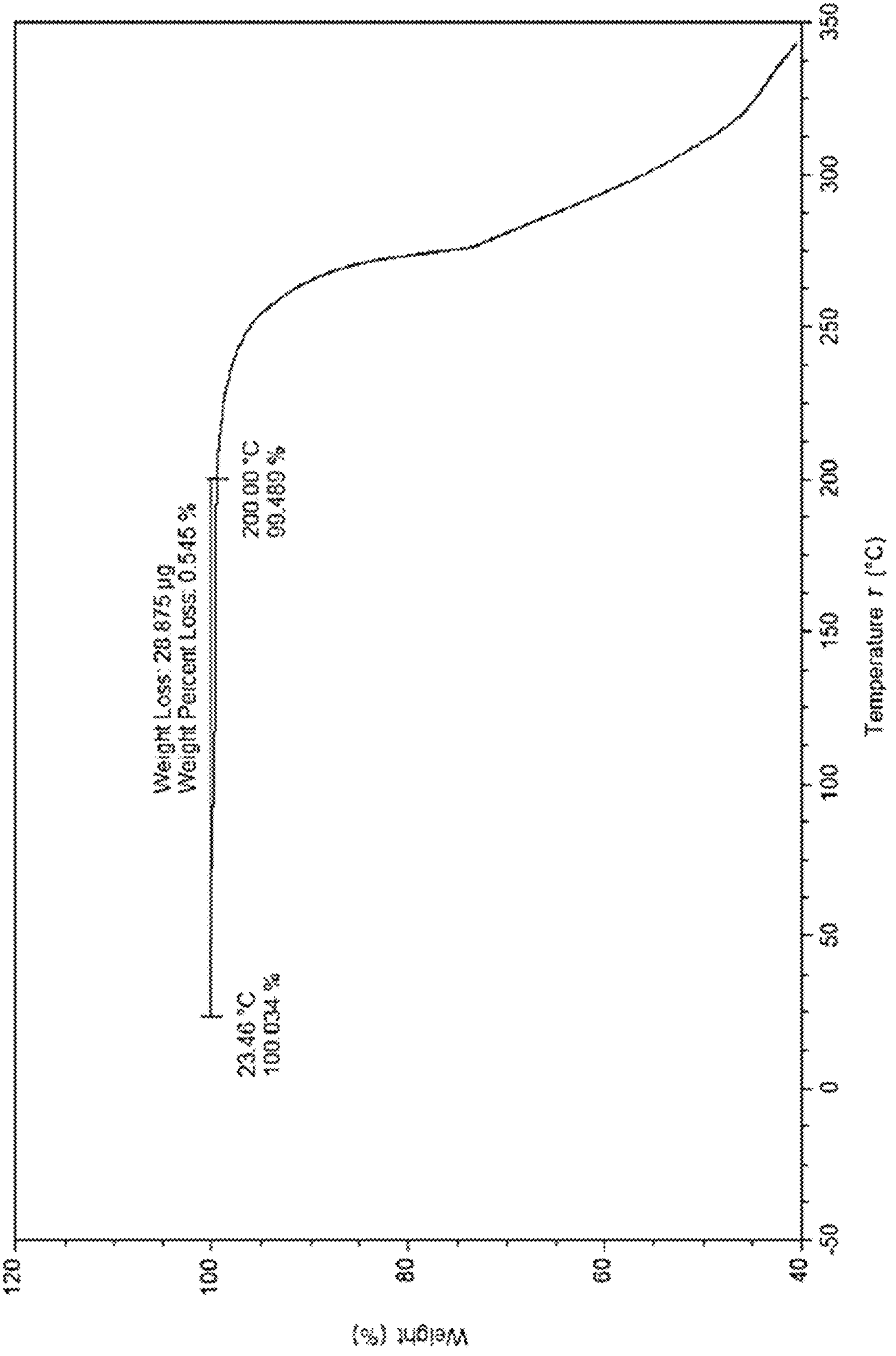
FIG. 6 shows a TGA thermogram of a lamotrigine hemifumarate anhydrate at 10° C./min.
Figure 7:
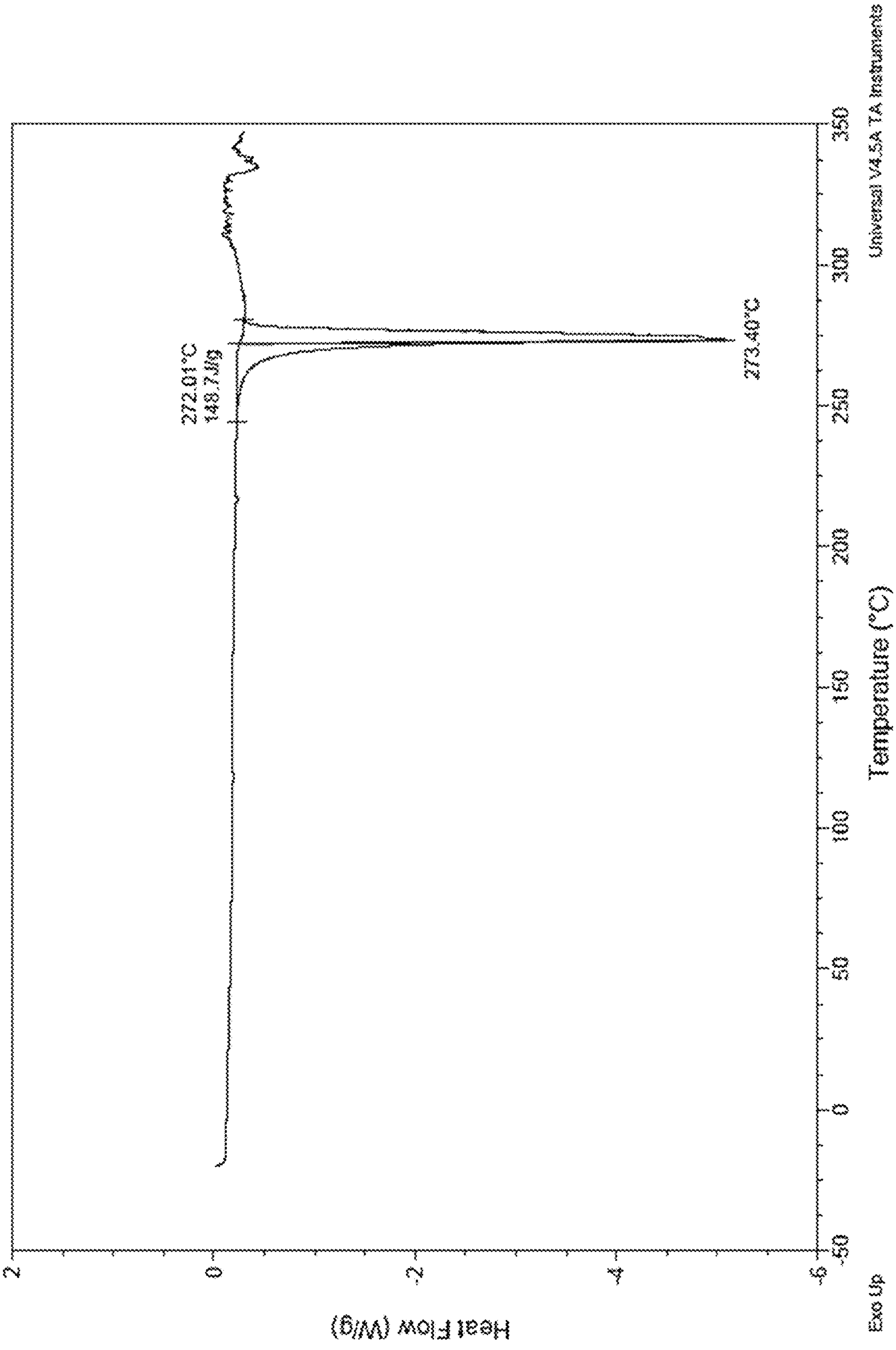
FIG. 7 shows a DSC thermogram of a lamotrigine hemifumarate anhydrate at 10° C./min.

Thermograms are presented in FIGS. 6 and 7. The TGA thermogram displays negligible weight loss up through 200° C., consistent with an anhydrous form. Subsequent weight loss beyond 250° C. is due to the thermal decomposition of lamotrigine (see Beattie 2012). The predominant endothermic thermal event observed by DSC (onset is 172.0° C., termination of fusion is 273.4° C., ΔHf=148.7 J/g) likely corresponds to melting and, based on the losses observed by TGA, is concomitant with decomposition.

The DVS isotherm indicates lamotrigine hemifumarate anhydrate exhibits low hygroscopicity from 5% to 95% RH (relative humidity). Hygroscopicity can be described as low, limited, or significant in part on concepts presented in reference. The reversible weight change through the sorption/desorption cycle was negligible. Equilibrium weight was achieved at each RH step. The material recovered from the DVS experiment remained physically unchanged, indicating that it is physically stable. Differences in peak intensities are due to poor orientation statistics from PO effects.

TABLE 1A

Characterization Results for Lamotrigine Hemifumarate Anhydrate

Figure 8:
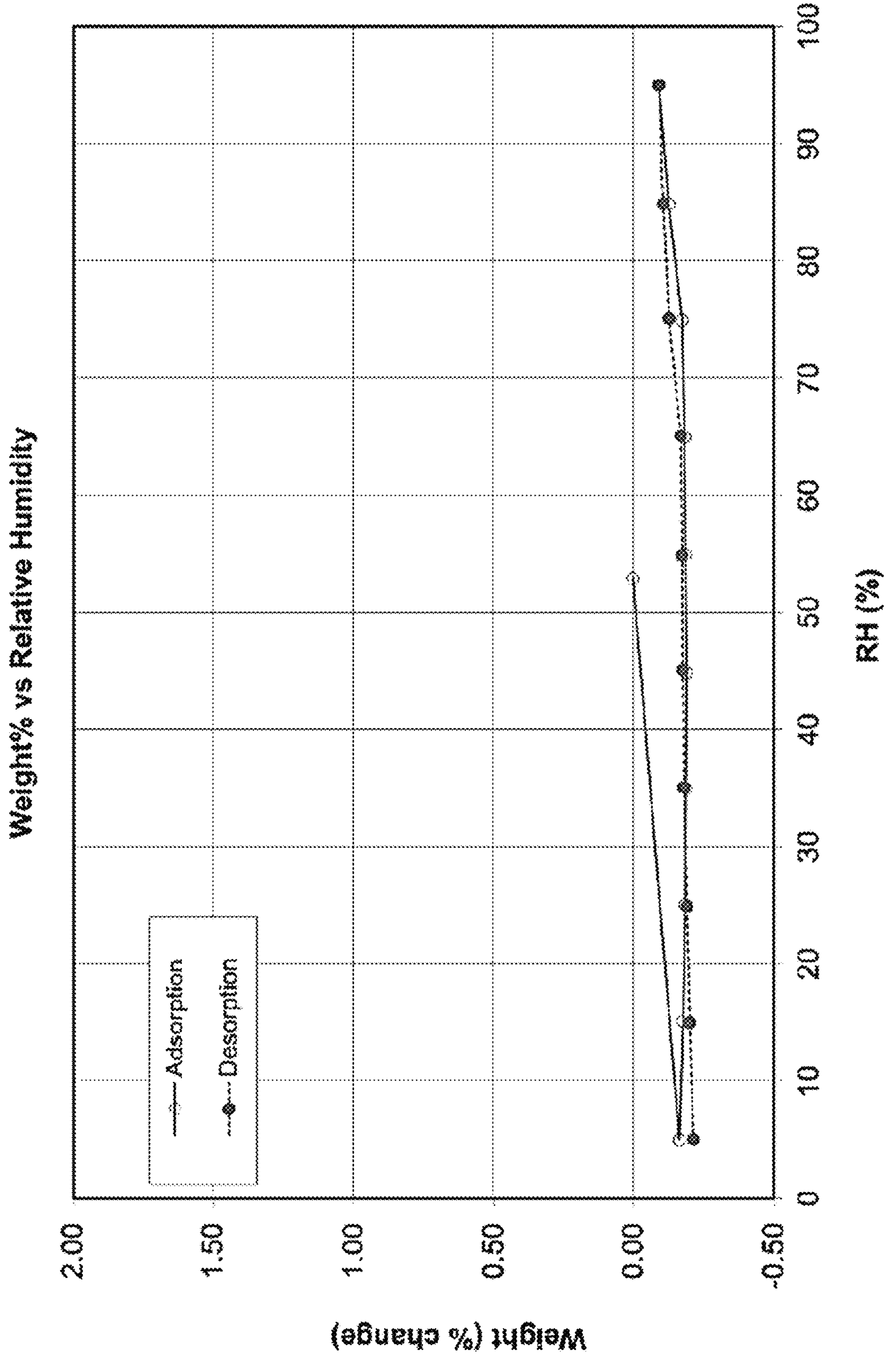
FIG. 8 shows a DVS isotherm of a lamotrigine hemifumarate anhydrate.
Figure 9:
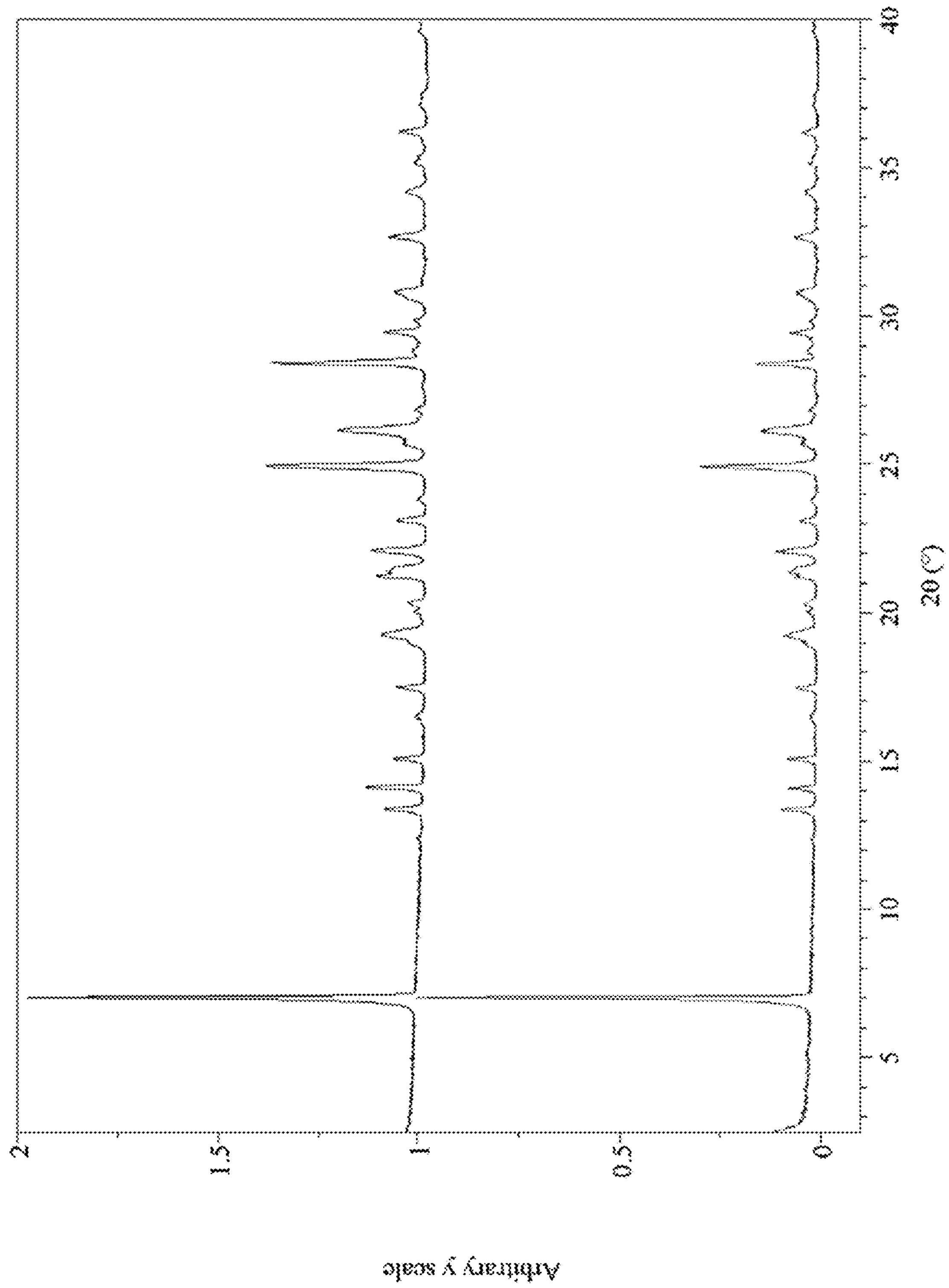
FIG. 9 shows XRPD patterns of a lamotrigine hemifumarate anhydrate before DVS analysis (top) and after DVS analysis (bottom).

| Test | Results | FIG. |
|---|---|---|
| XRPD | Crystalline representative of Lamotrigine Hemifumarate Anhydrate | FIG. 1 |
| Raman | Lamotrigine Hemifumarate Anhydrate | FIG. 2 |
| IR | Lamotrigine Hemifumarate Anhydrate | FIG. 3 |
| NMR | Consistent with chemical structure of lamotrigine and fumaric acid, integrated as 1:2 acid/base stoichiometry | FIG. 4 FIG. 5 |
| TGA | Negligible weight loss up to 200° C., which is consistent with an anhydrate. Weight loss above 250° C. associated with thermal degradation. | FIG. 6 |
| DSC | Melt with concomitant degradation, endo onset 272° C. (max 273° C., 148.7 J/g) | FIG. 7 |
| DVS | Low hygroscopicity from 5 to 95%, <0.2 reversible wt % change through cycle | FIG. 8 |
| Post DVS XRPD | Unchanged, identified as Lamotrigine Hemifumarate anhydrate | FIG. 9 |

TABLE 1B

Observed XRPD Peaks for Lamotrigine Hemifumarate Anhydrate

| °2θ | | d space (Å) | | Intensity (%) |
|---|---|---|---|---|
| 7.03 | ±0.20 | 12.564 | ±0.357 | 100 |
| 11.65 | ±0.20 | 7.590 | ±0.130 | 3 |
| 12.40 | ±0.20 | 7.132 | ±0.115 | 3 |
| 13.38 | ±0.20 | 6.612 | ±0.098 | 11 |
| 14.10 | ±0.20 | 6.276 | ±0.089 | 17 |
| 15.07 | ±0.20 | 5.874 | ±0.078 | 10 |
| 16.47 | ±0.20 | 5.378 | ±0.065 | 4 |
| 16.91 | ±0.20 | 5.239 | ±0.062 | 2 |
| 17.49 | ±0.20 | 5.067 | ±0.057 | 9 |
| 18.97 | ±0.20 | 4.674 | ±0.049 | 6 |
| 19.28 | ±0.20 | 4.600 | ±0.047 | 13 |
| 19.85 | ±0.20 | 4.469 | ±0.045 | 3 |
| 20.02 | ±0.20 | 4.432 | ±0.044 | 4 |
| 20.33 | ±0.20 | 4.365 | ±0.042 | 6 |
| 21.25 | ±0.20 | 4.178 | ±0.039 | 14 |
| 21.40 | ±0.20 | 4.149 | ±0.038 | 11 |
| 22.09 | ±0.20 | 4.021 | ±0.036 | 15 |
| 23.11 | ±0.20 | 3.846 | ±0.033 | 9 |
| 23.81 | ±0.20 | 3.734 | ±0.031 | 4 |
| 24.94 | ±0.20 | 3.567 | ±0.028 | 41 |
| 25.71 | ±0.20 | 3.462 | ±0.026 | 7 |
| 26.13 | ±0.20 | 3.408 | ±0.026 | 23 |
| 26.56 | ±0.20 | 3.353 | ±0.025 | 4 |
| 26.85 | ±0.20 | 3.318 | ±0.024 | 4 |
| 27.65 | ±0.20 | 3.224 | ±0.023 | 2 |
| 28.43 | ±0.20 | 3.137 | ±0.022 | 40 |
| 28.86 | ±0.20 | 3.091 | ±0.021 | 5 |
| 29.45 | ±0.20 | 3.031 | ±0.020 | 12 |
| 29.85 | ±0.20 | 2.991 | ±0.020 | 5 |

TABLE 1C

Prominent XRPD Peaks for Lamotrigine Hemifumarate Anhydrate

| °2θ | | d space (Å) | | Intensity (%) |
|---|---|---|---|---|
| 7.03 | ±0.20 | 12.564 | ±0.357 | 100 |
| 13.38 | ±0.20 | 6.612 | ±0.098 | 11 |
| 14.10 | ±0.20 | 6.276 | ±0.089 | 17 |
| 15.07 | ±0.20 | 5.874 | ±0.078 | 10 |
| 17.49 | ±0.20 | 5.067 | ±0.057 | 9 |
| 22.09 | ±0.20 | 4.021 | ±0.036 | 15 |
| 24.94 | ±0.20 | 3.567 | ±0.028 | 41 |

Example 2. Preparation of a Kit comprising Lamotrigine Hemifumarate Anhydrate and a Vehicle The following kits comprise two containers, in which the first container contains at least lamotrigine hemifumarate anhydrate and the second container contains a vehicle(s). The kits are designed such that the contents of the two containers can be mixed, resulting in a suspension of lamotrigine hemifumarate anhydrate in the vehicle. Mixing is conducted by adding the first container to the second container, or vice versa. Each container contains different ingredients as described below in Kits 1-7.

Kit 1. The first container contains at least lamotrigine hemifumarate anhydrate, and the second container contains at least water and a suspending agent.

Kit 2. The first container contains at least lamotrigine hemifumarate anhydrate, and the second container contains at least water and a pH adjuster.

Kit 3. The first container contains at least lamotrigine hemifumarate anhydrate, and the second container contains at least water, a suspending agent, a pH adjuster, and an antifoaming agent.

Kit 4. The first container contains at least lamotrigine hemifumarate anhydrate, and the second container contains at least water, a suspending agent, a pH adjuster, an anti-foaming agent, and an anti-caking agent.

Kit 5. The first container contains at least lamotrigine hemifumarate anhydrate, and the second container contains at least water, a suspending agent, a pH adjuster, an anti-foaming agent, an anti-caking agent, and a preservative.

Kit 6. The first container contains at least lamotrigine hemifumarate anhydrate and an anti-caking agent, and the second container contains at least water and a suspending agent.

Kit 7. The first container contains at least lamotrigine hemifumarate anhydrate and an anti-caking agent, and the second container contains at least water and a pH adjuster.

Example 3. Preparation of Lamotrigine Fumarate with Phosphoric Acid, Fumaric Acid, and Sodium Hydroxide Purified water (400 mL) was added to a first vessel along with a magnetic stir bar and stirring was initiated. The water was heated to approximately 60° C. Stirring was continued, and 3.4 g phosphoric acid and 8.0 g lamotrigine were added to the hot water and mixed until the lamotrigine was dissolved. The solution was cooled to approximately 25° C. Fumaric acid (3.6 g) was added to 320 mL of purified water in a second vessel and dissolved under stirring with approximately 14 g of 5N NaOH to facilitate the dissolution. The fumaric acid solution was then added to the lamotrigine solution, and the mixture was stirred for 30 minutes.

Example 4. Preparation of Lamotrigine Fumarate with Phosphoric Acid and Disodium Fumarate Purified water (500 mL) was added to a first vessel along with a magnetic stir bar and stirring was initiated. The water was heated to approximately 60° C. Stirring was continued, and 4.25 g phosphoric acid and 10.0 g lamotrigine were added to the hot water and mixed until the lamotrigine was dissolved. The solution was cooled to approximately 25° C. Disodium fumarate (6.25 g) was added to 400 mL of purified water in a second vessel and dissolved under stirring. The fumarate solution was then added to the lamotrigine solution with vigorous mixing, and the mixture was stirred for 30 to 60 minutes.

Example 5. Preparation of a Lamotrigine Fumarate with Solid Fumaric Acid

Purified water was added to a vessel along with a magnetic stir bar and stirring was initiated. Stirring was continued, and lamotrigine, sufficient to give 25 mg/mL, was added, and the solution was stirred (for about 15 min) until the lamotrigine was dispersed and partially dissolved. Fumaric acid was then added to the suspension to give 6.6 mg/mL. The pH was adjusted to pH 4.0 using 1N NaOH, and stirring continued for about 60 minutes. The resulting suspension was vacuum filtered through Whatman #5 filter paper, and the collected solids were dried. The melting point was determined to be 272° C.

Example 6. Preparation of a Lamotrigine Fumarate with a Fumaric Acid Solution and Solid Lamotrigine Purified water was added to a vessel along with a magnetic stir bar and stirring was initiated. Stirring was continued, and sufficient fumaric acid was added to give 6.6 mg/mL, and the solution was stirred (for about 15 min) until the fumaric acid dissolved. Lamotrigine powder was then added to the solution to give 25 mg/mL. The pH was adjusted to pH 4.0 using 1N NaOH, and stirring continued for about 60 minutes. The resulting suspension was vacuum filtered through Whatman #5 filter paper, and the collected solids were dried. The melting point was determined to be 272° C.

Example 7. Preparation of a Lamotrigine Fumarate with a Fumaric Acid Solution and Lamotrigine Suspension Purified water (50% of the final volume) was added to a first container along with fumaric acid sufficient to give 6.6 mg/mL in the final suspension. The preparation was stirred, and a small amount of 1N NaOH was added until the fumaric acid was dissolved.

Purified water (50% of the final volume) was added to a second container along with lamotrigine sufficient to give 25 mg/mL in the final suspension, and the suspension was mixed until the lamotrigine was well dispersed. The contents of the second container were then added to the first container while mixing for about 60 minutes. The resulting suspension was vacuum filtered through Whatman #5 filter paper, and the collected solids were dried. The melting point was determined to be 272° C.

The procedure was then repeated except the contents of the first container were added to the second container while mixing for about 60 minutes. The resulting suspension was vacuum filtered through Whatman #5 filter paper, and the collected solids were dried. The melting point was determined to be 272° C.

Example 8. Preparation of a Lamotrigine Fumarate with Phosphoric Acid and Disodium Fumaric Acid Purified water (about 50% of the final volume) was added to a first container along with disodium fumarate sufficient to give 2 mg/mL in the final suspension, and the suspension was mixed until the disodium fumarate was dissolved.

Purified water (about 50% of the final volume) was added to a second container along with sufficient lamotrigine to give 10 mg/mL in the final suspension. The suspension was heated to about 60° C. and ortho-phosphoric acid, sufficient to give 4.25 mg/mL in the final suspension, was added. The suspension was mixed until the lamotrigine was dissolved. The contents of the second container were added to the first container while mixing for about 15 minutes. The resulting suspension was vacuum filtered through Whatman #5 filter paper, and the collected solids were dried. The melting point was determined to be 272° C.

The procedure was repeated except the contents of the first container were added to the second container with mixing for about 15 minutes. The resulting suspension was vacuum filtered through Whatman #5 filter paper, and the collected solids were dried. The melting point was determined to be 272° C.

Example 9. Preparation of a Lamotrigine Fumarate with Citric Acid, Sulfuric Acid, and Disodium Fumaric Acid Purified water (about 50% of the final volume) was added to a first container along with disodium fumarate sufficient to give 2 mg/mL in the final suspension, and the suspension was mixed until the disodium fumarate was dissolved.

Purified water (about 50% of the final volume) was added to a second container along with lamotrigine, sufficient to give 10 mg/mL in the final suspension. The suspension was heated to 60° C. Citric acid, sufficient to give 1.19 mg/mL in the final suspension, and sulfuric acid, sufficient to give 4.25 mg/mL in the final suspension, were added to the second container, and the suspension was mixed until the lamotrigine was dissolved. The contents of the second container were added to the first container while mixing for about 15 minutes to form a lamotrigine fumarate formulation. The resulting suspension was vacuum filtered through Whatman #5 filter paper, and the collected solids were dried. The melting point was determined to be 272° C.

The procedure was repeated except the contents of the first container were added to the second container with mixing for about 15 minutes. The resulting suspension was vacuum filtered through Whatman #5 filter paper, and the collected solids were dried. The melting point was determined to be 272° C.

Example 10. Lamotrigine Fumarate Formulations Prepared with Phosphoric Acid

Formulations 1 and 2 were prepared containing the ingredients listed in Table 2. Both formulations contained a 1:1 mole ratio of fumarate to lamotrigine. Formulation 1 was prepared using the procedure of Example 3. After the fumarate salt was formed in situ, the HEC-HX was slowly added to the suspension with rapid mixing and was allowed to disperse and hydrate by mixing for about 1 hour. The remaining ingredients were then added individually and were allowed to dissolve or disperse before the next ingredient was added. The pH was measured, and phosphoric acid was added to achieve the target pH. The suspension was brought to final volume with additional purified water.

Formulation 2 was prepared using the procedure of Example 4. After the fumarate salt was formed in situ, the HEC-HX was slowly added to the suspension with rapid mixing and was allowed to disperse and hydrate by mixing for about 1 hour. The remaining ingredients were then added individually and were allowed to dissolve or disperse before the next ingredient was added. The pH was measured, and fumaric acid was added to achieve the target pH. The suspension was brought to the final volume with additional purified water.

The two formulations were dispensed into high density polyethylene (HDPE) bottles that were then capped and placed into storage at 5° C., 25° C., and 40° C. At periodic times, bottles were removed and analyzed for pH and by a stability-indicating UPLC method for the lamotrigine and sodium benzoate content and impurities. Results of the analyses are presented in Table 3.

TABLE 2

Compositions of Lamotrigine Fumarate Formulations Prepared with Phosphoric Acid

| | Formulation | |
|---|---|---|
| Component (mg/mL) | 1 | 2 |
| Phosphoric acid | 4.25 | 4.25 |
| Lamotrigine | 10.0 | 10.0 |
| Fumaric acid | 4.54 | — |
| Disodium fumarate | — | 6.25 |
| Hydroxyethyl cellulose (HEC-HX) | 3.5 | 3.5 |
| Sodium benzoate | 1.0 | 1.0 |
| Sucralose | 3.0 | 3.0 |
| Simethicone emulsion, 30% USP | 2.0 | 2.0 |
| Phosphoric acid for pH adjustment | q.s. pH 4.0 | — |
| Fumaric acid for pH adjustment | — | q.s. pH 4.0 |
| Purified water | q.s. | q.s. |

TABLE 3

Analysis of Lamotrigine Fumarate Formulations Prepared with Phosphoric Acid

| | | Formulation | |
|---|---|---|---|
| Test | Months | 1 | 2 |
| 5° C. Storage | | | |
| Lamotrigine assay (% initial) | 0 | 100.0 | 100.0 |
| | 1 | 99.0 | 101.9 |
| | 2 | 100.2 | 102.7 |
| | 3 | 98.0 | 100.9 |
| | 6 | 99.5 | 102.8 |
| Total impurities (wt % of Lamotrigine) | 0 | ND | ND |
| | 1 | 0.05 | ND |
| | 2 | ND | ND |
| | 3 | ND | ND |
| | 6 | ND | <0.05 |
| pH | 0 | 4.00 | 4.00 |
| | 1 | 4.03 | 3.99 |
| | 2 | 3.98 | 4.01 |
| | 3 | 3.92 | 4.04 |
| | 6 | 4.01 | 4.04 |
| 25° C. Storage | | | |
| Lamotrigine assay (% initial) | 0 | 100.0 | 100.0 |
| | 1 | 99.6 | 103.4 |
| | 2 | 99.8 | 103.1 |
| | 3 | 98.9 | 102.8 |
| | 6 | 99.9 | 102.9 |
| Total impurities (wt % of Lamotrigine) | 0 | ND | ND |
| | 1 | ND | ND |
| | 2 | ND | ND |
| | 3 | ND | ND |
| | 6 | ND | <0.05 |
| pH | 0 | 4.00 | 4.00 |
| | 1 | 3.97 | 3.99 |
| | 2 | 3.99 | 4.02 |
| | 3 | 3.94 | 4.06 |
| | 6 | 4.01 | 4.04 |
| 40° C. Storage | | | |
| Lamotrigine assay (% initial) | 0 | 100.0 | 100.0 |
| | 1 | 98.4 | 103.3 |
| | 2 | 99.9 | 103.1 |
| | 3 | 99.1 | 103.4 |
| | 6 | 101.3 | 104.5 |
| Total impurities (wt % of Lamotrigine) | 0 | ND | ND |
| | 1 | ND | ND |
| | 2 | ND | ND |
| | 3 | <0.05 | <0.05 |
| | 6 | <0.05 | <0.05 |
| pH | 0 | 4.00 | 4.00 |
| | 1 | 4.01 | 3.99 |
| | 2 | 3.99 | 4.02 |
| | 3 | 3.94 | 4.06 |
| | 6 | 4.00 | 4.04 |

ND = not detected

Example 11. Lamotrigine Fumarate Formulations Prepared at Differing Concentrations Formulations 3-9 were prepared with the ingredients listed in Table 4. Formulation 3 was prepared by adding lamotrigine (to give 1 mg/mL) and fumaric acid (to give 0.91 mg/mL) to about 80% of the final volume of purified water preheated to about 60° C., while mixing for about 1 hour. Disodium fumarate was added incrementally to adjust the pH to 4, then the HEC-HX was dispersed in the suspension. The formulation was mixed for about 2 hours and allowed to cool to room temperature. The remaining ingredients were added individually while mixing. The volume was brought to the final volume with purified water, and disodium fumarate (about 1.6 mg/mL) was added to adjust the final pH to 4.

Formulations 4-8 were prepared by adding lamotrigine and fumaric acid to about 80% of the final volume of purified water while mixing for about 1 hour. Disodium fumarate was added, and the formulations were mixed for about 1 to 2 hours. The HEC-HX was added and dispersed in the suspensions, and mixing continued for about 1 hour. The remaining ingredients were added individually while mixing. The volumes were brought to the final volume with purified water, and the pH was measured. Formulation 8 required about 1.7 mg/mL fumaric acid to adjust the pH to about 4, where no pH adjustments were needed for Formulations 4-7.

The formulations were dispensed into HDPE bottles, capped and induction sealed, and the samples were placed into stability storage at 5° C., 25° C., and 40° C. Samples were removed from storage after different storage periods and analyzed. The results for total impurities are presented in Table 5.

TABLE 4

Compositions of Lamotrigine Fumarate Formulations of Differing Concentrations

| | Formulation | | | | | | |
|---|---|---|---|---|---|---|---|
| Component (mg/mL) | 3 | 4 | 5 | 6 | 7 | 8 | 9 |
| Lamotrigine | 1.0 | 5.0 | 5.0 | 10.0 | 25.0 | 25.0 | 25.0 |
| Fumaric acid | 0.91 | 2.0 | 6.6 | 9.1 | 11.331 | 6.6 | 6.6 |
| Disodium fumarate | 1.62 | 2.46 | 8.25 | 22.7 | 19.9 | 8.25 | — |
| Hydroxyethyl cellulose (HEC-HX) | 3.5 | 3.5 | 3.5 | 3.5 | 3.5 | 3.5 | 3.5 |
| Sodium benzoate | 1.0 | 1.0 | 1.0 | 1.0 | 1.0 | 1.0 | 1.0 |
| Sucralose | 3.0 | 3.0 | 3.0 | 3.0 | 3.0 | 3.0 | 3.0 |
| Mixed berry flavor | — | — | 3.0 | — | — | — | — |
| Simethicone emulsion, 30% USP | 2.0 | 2.0 | 2.0 | 2.0 | 2.0 | 2.0 | 2.0 |
| Disodium fumarate for pH adjustment | q.s. pH 4 | — | — | — | — | — | — |
| Fumaric acid for pH adjustment | — | — | — | — | — | q.s. pH 4 | — |
| NaOH (5N) for pH adjustment | — | — | — | — | — | — | 3.55 |
| Purified water | q.s. | q.s. | q.s. | q.s. | q.s. | q.s. | q.s. |
| Final pH | 4.0 | 4.1 | 4.0 | 4.0 | 4.0 | 4.0 | 4.0 |
| Fumarate:lamotrigine mole ratio | 4.6:1 | 1.6:1 | 5.6:1 | 5.6:1 | 2.3:1 | 1.1:1 | 0.58:1 |

TABLE 5

Impurity Content of Lamotrigine Fumarate Formulations of Differing Concentrations

| | | Formulation | | | | | | |
|---|---|---|---|---|---|---|---|---|
| Test | Months | 3 | 4 | 5 | 6 | 7 | 8 | 9 |
| 5° C. Storage | | | | | | | | |
| Total impurities (wt % of Lamotrigine) | 0 | ND | ND | <0.05 | ND | ND | ND | ND |
| | 1 | <0.05 | ND | <0.05 | ND | ND | ND | ND |
| | 2 | 0.05 | ND | <0.05 | ND | ND | ND | ND |
| | 3 | 0.06 | <0.05 | <0.05 | ND | ND | ND | ND |
| | 6 | 0.06 | NT | NT | ND | ND | NT | ND |
| 25° C. Storage | | | | | | | | |
| Total impurities (wt % of Lamotrigine) | 0 | ND | ND | <0.05 | ND | ND | ND | ND |
| | 1 | 0.08 | <0.05 | <0.05 | ND | ND | ND | ND |
| | 2 | 0.11 | <0.05 | <0.05 | ND | ND | ND | ND |
| | 3 | 0.17 | <0.05 | <0.05 | <0.05 | ND | ND | ND |
| | 6 | 0.24 | <0.05 | <0.05 | <0.05 | ND | ND | ND |
| 40° C. Storage | | | | | | | | |
| Total impurities (wt % of Lamotrigine) | 0 | ND | ND | <0.05 | ND | ND | ND | ND |
| | 1 | 0.17 | 0.05 | <0.05 | ND | ND | ND | ND |
| | 2 | 0.31 | 0.05 | <0.05 | <0.05 | <0.05 | <0.05 | ND |
| | 3 | 0.50 | 0.05 | 0.07 | 0.08 | <0.05 | <0.05 | ND |
| | 6 | 0.78 | 0.09 | 0.19 | 0.17 | 0.05 | <0.05 | <0.05 |

NT = not tested;
ND = not detected

Example 12. Lamotrigine Fumarate Formulations Prepared with Different Methods of Mixing Formulations 10-17 were prepared with the ingredients listed in Table 6 using different methods of preparation. Formulations 10-13 and 15 were prepared by adding lamotrigine and fumaric acid to about 80% of the final volume of purified water while mixing with an overhead propeller paddle for about one hour. Then, sodium hydroxide was added, and the suspensions were stirred for about another two hours. At the time of sodium hydroxide addition, Formulations 11, 13, and 15 were subjected to mechanical homogenization using a rotor stator homogenizer for about five minutes, and Formulation 12 was subjected to sonication for about five minutes. At the end of this mixing period, the HEC-HX was added to and dispersed in each suspension, and overhead mixing was continued for about one additional hour. The remaining ingredients were added individually while mixing. The volumes were brought to the final volume with purified water, and the pH was measured.

Formulations 14, 16, and 17 were prepared using two vessels. The first vessel contained about 70% of the final volume of purified water, to which the lamotrigine and the first portion of fumaric acid was added with mixing for about an hour. Formulations 14 and 16 used overhead propeller paddle mixing, and Formulation 17 was mixed with a magnetic stir bar. The second vessel contained about 35% of the final volume of purified water, to which was added the second portion of fumaric acid and the sodium hydroxide to solubilize it with mixing. The contents of the second vessel were added to the first vessel with mechanical homogenization for about 5 minutes, and mixing continued for about 2 additional hours. At the end of this mixing period, the HEC-HX was added to each and dispersed in the suspensions, and mixing continued for about one additional hour. The remaining ingredients were added individually while mixing. The volumes were brought to the final volume with purified water, and the pH was measured.

TABLE 6

Compositions of Lamotrigine Fumarate Formulations Prepared with Different Mixing Conditions

| Component (mg/mL) | Formulation 10-12 | 13 | 14 | 15 | 16-17 |
|---|---|---|---|---|---|
| Lamotrigine | 5.0 | 5.0 | 5.0 | 25.0 | 25.0 |
| Fumaric acid-portion 1 | 6.6 | 2.5 | 1.4 | 12.6 | 7.2 |
| Fumaric acid-portion 2 | — | — | 1.1 | — | 5.4 |
| Hydroxyethyl cellulose (HEC-HX) | 3.5 | 3.5 | 3.5 | 3.5 | 3.5 |
| Sodium benzoate | 1.0 | 1.0 | 1.0 | 1.0 | 1.0 |
| Sucralose | 3.0 | 3.0 | 3.0 | 3.0 | 3.0 |
| Simethicone emulsion, 30% USP | 2.0 | 2.0 | 2.0 | 2.0 | 2.0 |
| 5N NaOH for pH adjustment | 14.72 | 2.8 | 2.8 | 18.2 | 18.2 |
| Purified water | q.s. | q.s. | q.s. | q.s. | q.s. |
| Final pH | 4.0 | 4.0 | 4.0 | 4.0 | 4.0 |
| Fumarate:lamotrigine mole ratio | 2.9:1 | 1.1:1 | 1.1:1 | 1.11:1 | 1.11:1 |

Example 13. Lamotrigine Fumarate Formulations of Varying pH

Formulations 18-23 were prepared with the components in Table 7 and Table 8. The formulations were prepared by adding the lamotrigine to purified water at approximately 80% of the final volume while mixing. The fumaric acid was then added, and the suspensions were allowed to mix for about 1 hour. Then, the HEC-HX was added with rapid mixing to disperse and hydrate the cellulose. The mixing continued for about 1 additional hour, then the remaining ingredients were added individually to allow each to dissolve before the next addition. The pH was measured and adjusted to the target pH with sodium hydroxide, then the formulations were brought to the final volume with purified water.

The formulations were dispensed into white, opaque, high-density polyethylene (HDPE) bottles, which were capped, induction sealed, and placed into storage at 5° C., 25° C., and 40° C. The bottles were removed from temperature storage at various times and analyzed for pH and lamotrigine, sodium benzoate, and impurity content. The results for the Formulas 18, 23, 24, and 28 when stored at 25° C. and 40° C. are provided in Table 9.

TABLE 7

Compositions of Lamotrigine Fumarate Formulations of Varying pH (5 mg/mL)

| Component (mg/mL) | Formulation 18 | 19 | 20 | 21 | 22 | 23 |
|---|---|---|---|---|---|---|
| Lamotrigine | 5.0 | 5.0 | 5.0 | 5.0 | 5.0 | 5.0 |
| Fumaric acid | 2.5 | 2.5 | 2.5 | 2.5 | 2.5 | 2.5 |
| Hydroxyethyl cellulose HX | 3.5 | 3.5 | 3.5 | 3.5 | 3.5 | 3.5 |
| Sodium benzoate | 1.0 | 1.0 | 1.0 | 1.0 | 1.0 | 1.0 |
| Sucralose | 3.0 | 3.0 | 3.0 | 3.0 | 3.0 | 3.0 |
| Simethicone emulsion | 2.0 | 2.0 | 2.0 | 2.0 | 2.0 | 2.0 |
| 5N NaOH | 1.46 | 2.15 | 4.61 | 4.65 | 4.67 | 4.68 |
| Purified water | q.s. | q.s. | q.s. | q.s. | q.s. | q.s. |
| pH | 3.6 | 3.8 | 4.2 | 4.4 | 4.6 | 4.8 |

TABLE 8

Compositions of Lamotrigine Fumarate Formulations of Varying pH (25 mg/mL)

| Component (mg/mL) | Formulation 24 | 25 | 26 | 27 | 28 |
|---|---|---|---|---|---|
| Lamotrigine | 25 | 25 | 25 | 25 | 25 |
| Fumaric acid | 12.6 | 12.6 | 12.6 | 12.6 | 12.6 |
| Hydroxyethyl cellulose HX | 3.5 | 3.5 | 3.5 | 3.5 | 3.5 |
| Sodium benzoate | 1.0 | 1.0 | 1.0 | 1.0 | 1.0 |
| Sucralose | 3.0 | 3.0 | 3.0 | 3.0 | 3.0 |
| Simethicone emulsion | 2.0 | 2.0 | 2.0 | 2.0 | 2.0 |
| 5N NaOH | 12.8 | 14.8 | 18.8 | 25.8 | 26.8 |
| Purified water | q.s. | q.s. | q.s. | q.s. | q.s. |
| pH | 3.6 | 3.8 | 4.2 | 4.6 | 4.8 |

TABLE 9

Analysis of Lamotrigine Fumarate Formulations of Various pH

| Test | Months | Formulation 18 | 23 | 24 | 28 |
|---|---|---|---|---|---|
| 25° C. Storage | | | | | |
| Lamotrigine assay | 0 | 100.0 | 100.0 | 100.0 | 100.0 |
| (% initial) | 1 | 102.3 | 102.9 | 102.7 | 103.5 |
| | 2 | 101.7 | 102.0 | 102.4 | 101.6 |
| | 3 | 101.2 | 101.6 | 99.4 | 100.2 |
| | 6 | 100.5 | 100.9 | 101.6 | 100.8 |
| | 9 | 103.8 | 105.2 | 104.3 | 104.8 |
| | 12 | 100.4 | 102.9 | 101.9 | 102.6 |

TABLE 9-continued

| Analysis of Lamotrigine Fumarate Formulations of Various pH | | | | | |
|---|---|---|---|---|---|
| | | Formulation | | | |
| Test | Months | 18 | 23 | 24 | 28 |
| USP Impurity C (wt % of Lamotrigine) | 0 | ND | ND | ND | ND |
| | 1 | ND | ND | ND | ND |
| | 2 | ND | ND | ND | ND |
| | 3 | <0.05 | ND | ND | ND |
| | 6 | ND | ND | ND | ND |
| | 9 | ND | ND | ND | ND |
| | 12 | <0.05 | <0.05 | ND | ND |
| Total impurities (wt % of Lamotrigine) | 0 | <0.05 | <0.05 | ND | ND |
| | 1 | <0.05 | <0.05 | ND | ND |
| | 2 | <0.05 | <0.05 | ND | ND |
| | 3 | <0.05 | <0.05 | ND | ND |
| | 6 | <0.05 | <0.05 | ND | ND |
| | 9 | <0.05 | <0.05 | <0.05 | <0.05 |
| | 12 | <0.05 | <0.05 | <0.05 | ND |
| pH | 0 | 3.60 | 4.80 | 3.65 | 4.87 |
| | 1 | 3.61 | 4.84 | 3.67 | 4.97 |
| | 2 | 3.60 | 4.82 | 3.65 | 4.96 |
| | 3 | 3.61 | 4.83 | 3.67 | 4.99 |
| | 6 | 3.64 | 4.85 | 3.69 | 5.02 |
| | 9 | 3.60 | 4.81 | 3.65 | 5.01 |
| | 12 | 3.64 | 4.85 | 3.69 | 5.08 |
| 40° C. Storage | | | | | |
| Lamotrigine assay (% initial) | 0 | 100.0 | 100.0 | 100.0 | 100.0 |
| | 1 | 102.6 | 102.7 | 103.9 | 105.0 |
| | 2 | 100.1 | 101.8 | 103.6 | 105.3 |
| | 3 | 99.7 | 99.4 | 100.5 | 101.0 |
| | 6 | 99.5 | 100.3 | 99.8 | 102.5 |
| USP Impurity C (wt % of Lamotrigine) | 0 | ND | ND | ND | ND |
| | 1 | <0.05 | <0.05 | ND | ND |
| | 2 | <0.05 | <0.05 | ND | ND |
| | 3 | <0.05 | <0.05 | ND | ND |
| | 6 | <0.05 | 0.06 | <0.05 | <0.05 |
| Total impurities (wt % of Lamotrigine) | 0 | <0.05 | <0.05 | ND | ND |
| | 1 | <0.05 | <0.05 | <0.05 | <0.05 |
| | 2 | <0.05 | <0.05 | ND | ND |
| | 3 | <0.05 | 0.05 | <0.05 | <0.05 |
| | 6 | 0.06 | 0.11 | <0.05 | <0.05 |
| pH | 0 | 3.60 | 4.80 | 3.65 | 4.87 |
| | 1 | 3.60 | 4.86 | 3.66 | 5.01 |
| | 2 | 3.59 | 4.85 | 3.65 | 5.02 |
| | 3 | 3.61 | 4.86 | 3.67 | 5.04 |
| | 6 | 3.64 | 4.89 | 3.69 | 5.08 |

ND = not detected

Example 14. Lamotrigine Fumarate Formulations of Varying Suspending and Preserving Agents Formulations 29-39 were prepared with the components in Table 10. Formulations 29-32, 34, and 35 were prepared by adding the lamotrigine to purified water at approximately 20% of the final volume with mixing. The fumaric acid was then added, and the suspensions were allowed to mix for about 1 hour using an overhead mixer. Sodium hydroxide was then added, and the suspensions were homogenized with a rotor/stator homogenizer for about 5 minutes, and mixing continued for about an hour. The HEC-HX, HPMC K1500, Xanthan gum, or microcrystalline cellulose and sodium carboxymethyl cellulose was added with rapid mixing to disperse and hydrate the cellulose. Mixing continued for about 1 additional hour, then the remaining ingredients were added individually to allow each to dissolve before the next addition. The suspensions were brought to the final volume with purified water, and the pH was measured.

Formulations 33 and 39 were prepared by adding the lamotrigine to each first vessel containing purified water at approximately 60% of the final volume while mixing. The fumaric acid was then added, and the suspensions were allowed to mix for about 1 hour using an overhead mixer. Sodium hydroxide was then added, and the suspensions were mixed for at least 30 minutes. The suspensions were homogenized for about 45 to 60 minutes while keeping the suspensions at about 25° C.±5° C. The silicon dioxide was added with mixing and homogenization. Xanthan gum was added while mixing to purified water at approximately 30% of the final volume in second vessels. The mixing continued until a clear solution was formed. The contents of the second vessel were added to the first vessel while mixing. The remaining ingredients were added individually to the first vessel while mixing to allow each to dissolve before the next addition. The pH was measured and adjusted to about 4 with additional HCl. The suspensions were then brought to the final volume with purified water.

Formulation 36 was prepared by adding the HEC-HX to a first vessel containing purified water at approximately 30% of the final volume while mixing, and heating the dispersion to about 60° C. When the cellulose was well dispersed, room temperature purified water, approximately 30% of the final volume, was added while mixing, and the formulation was allowed to come to room temperature while mixing. In a second vessel, lamotrigine and fumaric acid were added to purified water at approximately 20% of the final volume, and the suspension was mixed for about an hour. The sodium hydroxide was added to the second vessel, wherein mechanical homogenization was conducted for about 5 minutes, and then the suspension was mixed for about an hour. The contents of the second vessel were added to the first vessel while mixing. Mixing continued while the remaining ingredients were added individually to allow each to dissolve before the next addition. The suspension was brought to final volume with purified water, and the pH was measured.

TABLE 10

| Compositions of Lamotrigine Fumarate Formulations with Various Suspending and Preserving Agents | | | | | | | | | | | |
|---|---|---|---|---|---|---|---|---|---|---|---|
| | Formulation | | | | | | | | | | |
| Component (mg/mL) | 29 | 30 | 31 | 32 | 33 | 34 | 35 | 36 | 37 | 38 | 39 |
| Lamotrigine | 5.0 | 5.0 | 5.0 | 5.0 | 5.0 | 5.0 | 5.0 | 5.0 | 25.0 | 25.0 | 25.0 |
| Fumaric acid | 1.3 | 1.2 | 2.5 | 2.5 | 1.3 | 2.5 | 1.3 | 1.3 | 6.6 | 5.78 | 6.6 |
| HEC-HX | 3.5 | 4.0 | — | — | — | — | 4.0 | — | 4.0 | | |
| HPMC K1500 | — | — | 8.0 | — | — | — | — | — | — | | |
| Xanthan gum | — | — | — | 1.5 | 1.5 | — | — | — | — | | 1.5 |
| RC-591 | — | — | — | — | — | 12.0 | — | — | — | | |
| HEC-H | — | — | — | — | — | — | — | 4.0 | — | 4.0 | |
| MCC PH112 | — | — | — | — | — | — | — | 2.0 | — | | |
| Colloidal silicon dioxide | — | — | — | — | 5.0 | — | — | — | — | | 5.0 |

TABLE 10-continued

Compositions of Lamotrigine Fumarate Formulations with Various Suspending and Preserving Agents

| Component (mg/mL) | Formulation 29 | 30 | 31 | 32 | 33 | 34 | 35 | 36 | 37 | 38 | 39 |
|---|---|---|---|---|---|---|---|---|---|---|---|
| Sodium benzoate | 1.0 | 1.0 | 1.0 | 1.0 | 1.0 | 1.0 | — | 1.0 | 1.0 | 1.0 | 1.0 |
| Benzyl alcohol | — | — | — | — | — | — | 5.0 | — | | | |
| Sucralose | 3.0 | 3.0 | 3.0 | 3.0 | 3.0 | 3.0 | 3.0 | 3.0 | 3.0 | 3.0 | 3.0 |
| Simethicone Emulsion | 2.0 | 2.0 | 2.0 | 2.0 | 2.0 | 2.0 | 2.0 | 2.0 | 2.0 | 2.0 | 2.0 |
| 5N NaOH | 1.3 | 0.2 | 2.8 | 2.8 | 0.2 | 2.8 | 0.3 | 0.3 | 2.8 | 1.4 | 2.3 |
| Purified water | q.s. | q.s. | q.s. | q.s. | q.s. | q.s. | q.s. | q.s. | q.s. | q.s. | q.s. |
| pH | 4.0 | 4.0 | 4.0 | 4.0 | 4.0 | 4.0 | 4.0 | 4.0 | 4.0 | 4.0 | 4.0 |

HEC = Hydroxyethyl cellulose (H and HX are viscosity grades)
HPMC = Hydroxypropyl methylcellulose
RC-591 = Microcrystalline cellulose and sodium carboxymethyl cellulose
MCC = Microcrystalline cellulose (PH112 is a grade)

Example 15. Preparation of Lamotrigine Fumarate Formulation 43

Formula 43 at different strengths were prepared with the components in Table 12, using two different batches of lamotrigine. Xanthan gum was dissolved in a first vessel in 30% of water. 1N NaOH was prepared in a second vessel to be used it for adjusting the pH. 1N HCl was prepared in a third vessel to be used for adjusting the pH.

60% of water was dispensed into the main tank. Lamotrigine was added to the main tank and mixed for suitable time. Fumaric acid was added to the dispersion and mixed for suitable time. 1N NaOH was added and mixed for suitable time. The dispersion was homogenized until a PSD (Particle Size Distribution) of D90 not more than 60 μm was obtained. Cab-O-sil® silicon dioxide was added to the dispersion and homogenized for suitable time. The xanthan gum solution from the first vessel was added to the dispersion in the main tank and mixed for suitable time. Sodium benzoate, sucralose, and simethicone were then added and stirred for a suitable time after addition of each excipient. The pH was adjusted to 3.6 to 4.6 using 1N NaOH or 1N HCl. The final weight with water was adjusted and the suspension was filled into a suitable bottle and sealed.

TABLE 11

| Lamotrigine analysis | 5 mg/ml | 25 mg/ml |
|---|---|---|
| Lamotrigine Assay (%) | 99.9 | 100 |
| Assay of Sod benzoate (%) | 98.9 | 99.8 |
| Viscosity (cPs) | 32.8 | 35.3 |
| pH | 4.22 | 4.08 |

TABLE 11-continued

Lamotrigine analysis

| Particle size distribution | | |
|---|---|---|
| Parameter | μm | μm |
| D10 | 3.6 | 3.84 |
| D50 | 17.3 | 15.7 |
| D90 | 42.6 | 39.1 |
| **Impurity profile** | | |
| Impurity | % Imp | % Imp |
| Lamotrigine RC-C | ND | ND |
| Single Maximum | ND | ND |
| Total impurities | ND | ND |
| **Dissolution profile** | | |
| Time | % Dissolution | % Dissolution |
| 5 min | 99 | 98 |
| 10 min | 100 | 98 |
| 15 min | 100 | 98 |
| 20 min | 100 | 98 |
| 30 min | 100 | 98 |
| 45 min | 100 | 98 |
| 60 min | 100 | 98 |

ND = not detected

TABLE 12

Formulation 43—Lamotrigine Oral Suspension Formulations (5 mg/mL and 25 mg/mL)

| | | Strength | 5 mg/mL | | 25 mg/mL | |
|---|---|---|---|---|---|---|
| S. no. | Ingredients | Functional category | mg/mL | % w/w | mg/mL | % w/w |
| 1 | Lamotrigine USP | Active | 5.00 | 0.500 | 25.00 | 2.500 |
| 2 | Fumaric Acid NF | Salting agent | 1.32 | 0.132 | 6.60 | 0.660 |

TABLE 12-continued

Formulation 43—Lamotrigine Oral Suspension Formulations (5 mg/mL and 25 mg/mL)

| S. no. | Ingredients | Strength / Functional category | 5 mg/mL mg/mL | 5 mg/mL % w/w | 25 mg/mL mg/mL | 25 mg/mL % w/w |
|---|---|---|---|---|---|---|
| 3 | Sodium Hydroxide NF | pH adjuster | 0.04 | 0.004 | 0.20 | 0.020 |
| 4 | Xanthan gum NF | Suspending agent | 1.50 | 0.150 | 1.50 | 0.150 |
| 5 | Sodium Benzoate NF | Preservative | 1.00 | 0.100 | 1.00 | 0.100 |
| 6 | Sucralose NF | Sweetener | 3.00 | 0.300 | 3.00 | 0.300 |
| 7 | Simethicone Emulsion (30%) USP | Anti-foaming agent | 2.00 | 0.200 | 2.00 | 0.200 |
| 8 | Silicon dioxide | Anti-caking agent | 5.00 | 0.500 | 5.00 | 0.500 |
| 9 | 1N HCl or 1N NaOH | pH adjuster | Q.S. | Q.S. | Q.S. | Q.S. |
| 10 | Purified Water USP | Vehicle | Q.S. | 98.114 | Q.S. | 95.566 |
| | Total | | | 100.00 | — | 100.00 |

Example 16. Free Fraction of Lamotrigine in Lamotrigine Fumarate Formulations Several formulations were analyzed for the concentration of soluble lamotrigine during the formation of the lamotrigine fumarate and/or after final formulations were completed. The analysis was conducted by filtering one to two milliliter aliquots through nylon 0.2 μm filters, diluting the filtrate sample to 1:50, and analyzing them for lamotrigine content by Ultra High-Performance Liquid Chromatography (UHPLC) with ultraviolet detection.

Formulation 6 was prepared with differing amounts of sodium fumarate and sodium hydroxide to generate formulations at pH 2, 3, 4, 5, 6, and 7. These formulations and Formulations 33 and 39 were analyzed approximately 24 hours after preparation (see Table 14). Additional formulations were prepared with the components in Table 13.

Lamotrigine fumarate formation in Formulation 40 was accomplished by adding the lamotrigine and fumaric acid to 200 mL purified water with overhead stirring, which was continued for 30 minutes. The sodium hydroxide was then added, and the suspension was homogenized for about 5 minutes with concomitant stirring for 30 minutes.

Formulation 41 was prepared by adding the HEC-HX to 400 mL of purified water that was pre-heated to 70° C. The formulation was mixed with overhead stirring until the HEC-HX was well dispersed. Then, 400 mL of room temperature purified water was added, and the solution was brought to about 25° C. The lamotrigine and fumaric acid were added, and the suspension was mixed for 30 minutes. Sodium hydroxide was then added, and the suspension was homogenized for about 5 minutes with concomitant stirring for 30 minutes.

Formulations 42A and 42B were duplicate formulations, each prepared by adding the HEC-HX to 400 mL of purified water that was pre-heated to 70° C. in a first vessel. The formulations were mixed with overhead stirring until the HEC-HX was well dispersed. Then, 400 mL of room temperature purified water was added, and the solutions were brought to about 25° C. The lamotrigine was then added with continued mixing. Fumaric acid and sodium hydroxide were added to a second vessel containing 50 mL purified water, and mixed until the fumaric acid was dissolved. This solution was added to the first vessel while mixing, followed by homogenization of the formulation for 10 minutes.

Figure 10:
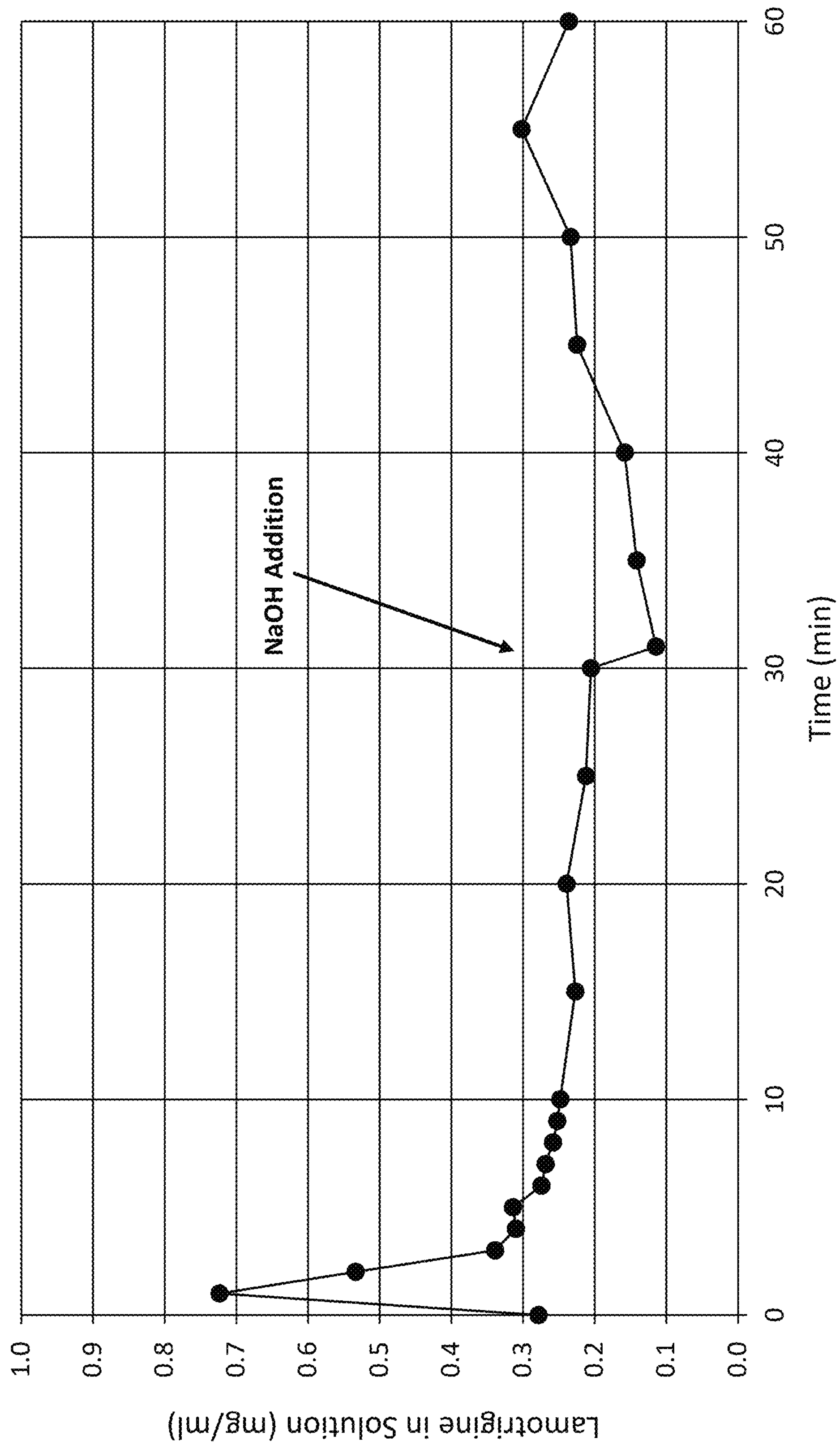
FIG. 10 shows the amount of soluble lamotrigine in Formulation 40.
Figure 11:
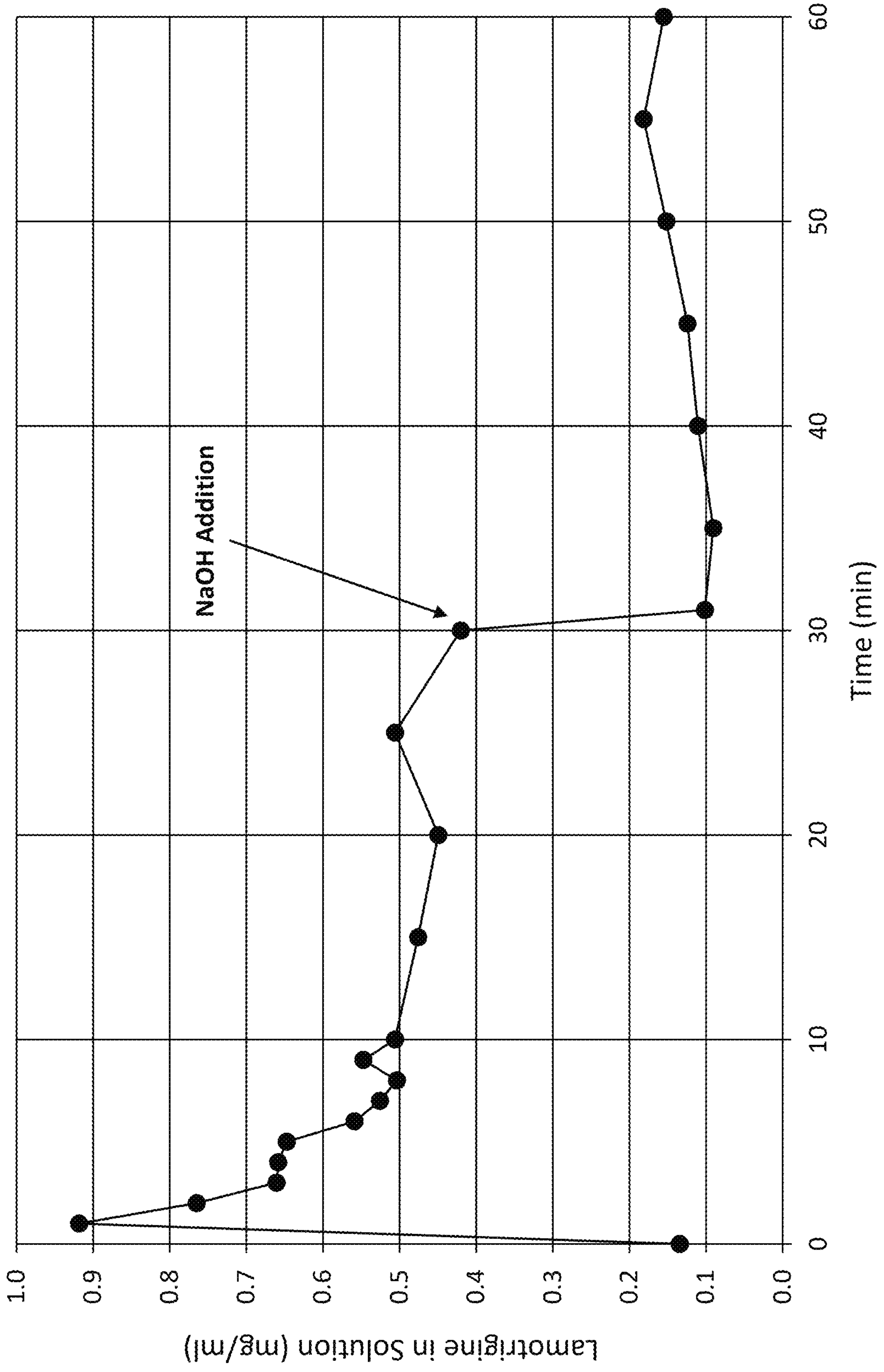
FIG. 11 shows the amount of soluble lamotrigine in Formulation 41.

At various times at and after the addition of fumaric acid and sodium hydroxide in Formulations 40 and 41, sample aliquots were withdrawn and analyzed. Samples were also taken from completed Formulations 42A and 42B at one hour and 24 hours after preparation. The results are shown in FIG. 10 and FIG. 11 for Formulations 40 and 41, respectively, and Table 14 for Formulations 42A and 42B, 33, 39, and 6 at various pH values.

The results for Formulations 40 and 41 showed a rapid increase in lamotrigine concentration in solution when the fumaric acid was added, followed by a reduction in the concentration as the lamotrigine fumarate salt was formed. When the sodium hydroxide was added, the soluble amount dropped further as the pH approached 4.

TABLE 13

Compositions of Lamotrigine Fumarate Formulations Monitored for Lamotrigine Soluble Content

| Component (grams) | Formulation 40 | 41 | 42A | 42B |
|---|---|---|---|---|
| Lamotrigine | 5.00 | 25.0 | 25.0 | 25.0 |
| Fumaric acid | 1.32 | 6.60 | 6.6 | 6.6 |
| Hydroxyethyl cellulose (HEC-HX) | 0.21 | 4.0 | — | — |
| 5N NaOH | 2.81 | 2.8 | 2.31 | 2.30 |
| Purified water | 200 | 800 | 850 | 850 |

TABLE 14

Soluble Lamotrigine Fumarate (mg/mL) in Various Liquid Formulations

| Formulation | pH | Time after preparation 1 h | 24 h |
|---|---|---|---|
| 33 | | — | 0.08 |
| 39 | | — | 0.05 |
| 42A | | 0.10 | 0.05 |
| 42B | | 0.18 | 0.08 |
| 6 | 2 | — | 0.36 |
| | 3 | — | 0.06 |
| | 4 | — | 0.02 |
| | 5 | — | 0.02 |
| | 6 | — | 0.04 |
| | 7 | — | 0.12 |

Example 17. Analytical Methods

X-ray Powder Diffraction (XRPD) (FIG. 1). XRPD patterns were collected with a PANalytical Empyrean diffractometer in Bragg-Brentano geometry using a Cu radiation source generated at 45 kV/40 mA. A silicon standard was analyzed to check the instrument alignment. Prior to the analysis, a specimen of the sample was packed into a silicon zero background diffraction holder with a 10×0.2 mm well and analyzed in reflection geometry. The X-ray source was configured with Soller slits of 0.04 radians, a fixed anti-scatter slit of ¼°, a mask of 4 mm, and a fixed divergence slit of 1⁄16°. The diffracted beam passed through a 7.5 mm anti-scatter slit and large Soller slits of 0.02 radians to the detector. Diffraction patterns were collected with Data Collector software v. 6.1b using a PIXcel3D-Medipix3 1×1 detector located 240 mm from the specimen. The data was acquired using up to 18 repetitions from 2-40° 2θ with sample spinning at a revolution time of 2 seconds.

Indexing and Pawley Refinement from XRPD Patterns. Indexing of an XRPD pattern is a computational method that searches a set of crystallographic space group and unit cell parameters to match the observed Bragg angles in a powder pattern. If successful and all observed Bragg peaks can be attributed to the indexing solution, it is highly likely the XRPD pattern represents a single crystalline phase. The indexing solution can be used to perform whole-pattern Pawley refinement in order to accurately determine the unit cell volume and cell parameters and investigate the fit residual for crystalline phase impurities. Topas was used for Indexing and Pawley refinements. Refinements are performed on all parameters simultaneously to a convergence of 0.001 in $\chi 2$. Refined unit cell parameters, space group, and fit residual are provided in a table with the graphical representation of the Pawley refinement result. Further refinement parameters include but may not be limited to the following. The background was modeled using a Chebychev polynomial function and a 1/x contribution to account for air scattering. If needed, further broad scattering features such as caused by amorphous content may be modeled by a broad first principle peak contribution. Bragg peaks are fitted to a first principles peak function with Gaussian crystallite size broadening (TG) and Lorentzian strain broadening (εL). Peak asymmetry due to axial divergence was modeled using the simple axial model (SAM) with a start value of 10 mm. Sample displacement (dsamp) correction was used to account for Bragg peak shifts and listed in the parameter table if used.

Peak Picking from XRPD Patterns Whole-pattern Pawley refinement parameters were used to generate the Miller Indices (hkl) and respective d-spacings for all the allowed peaks. The peak picking data presented contain X-ray diffraction patterns with labeled peaks and tables with peak lists. Under most circumstances, peaks within the range of up to about 30° 2θ were selected. The location of the peaks along the x-axis (° 2θ) in both the figures and the tables were corrected for sample displacement error and determined using measurement data viewer software. Rounding algorithms were used to round each peak to the nearest 0.01° 2θ. Peak position variabilities were given to within ±0.2° 2θ based upon recommendations outlined in the United States Pharmacopcia (USP) discussion of variability in X-ray powder diffraction. The wavelength used to calculate d-spacings was 1.5405929 Å, the Cu-Kα1 wavelength. The variability associated with d-spacing estimates was calculated from the USP recommendation at each d-spacing and provided in the respective data tables. Per USP guidelines, variable hydrates and solvates could display peak variances greater than 0.2° 2θ and therefore peak variances of 0.2° 2θ were not applicable to these materials. Particle statistics and/or preferred orientation were not assessed, and the XRPD patterns may not have been representative of the powder average intensity for the sample. Peak tables that contain data identified as Prominent Peaks were a subset of the entire observed peak list. Prominent peaks were selected from observed peaks by identifying preferably non-overlapping, low-angle peaks, with strong intensity. When possible, the Miller Indices from allowed peaks were used to guide the selection of prominent peaks.

DSC Sample Preparation and Analysis (FIG. 7). DSC was performed using a TA Instruments model Q10 differential scanning calorimeter. The instrument was calibrated using indium. The sample was placed into a standard aluminum DSC pan, covered with a lid that was manually pierced with a pin, and the weight was accurately recorded. The pan lid was crimped prior to sample analysis. An aluminum pan configured as the sample pan was placed on the reference side of the cell. The sample was analyzed in a single run from −20 to 350° C. at a heating rate of 10° C./min under a purge of nitrogen (50 cc/min).

Dynamic Vapor Sorption (DVS). Moisture sorption/desorption data were collected on a VTI SGA-100 Vapor Sorption Analyzer. Samples were not dried prior to analysis. Sorption and desorption data were collected over a range from 5% to 95% RH at 10% RH increments under a dry air purge. The equilibrium criterion used for analysis was less than 0.0100% weight change in 5 minutes with a maximum equilibration time of 3 hours with a 2-minute data logging interval. Data were not corrected for the initial moisture content of the samples. Sodium chloride was used as a calibration standard.

FT-IR Microscopy Sample Preparation and Analysis (FIG. 3). Infrared analyses were performed by reflection/absorption (R/A) using an all-reflecting objective (ARO), 15×, 0.88 NA or by attenuated total reflection (ATR) using a type IIIa hemispherical diamond internal reflection element (IRE), dAT objective, 36×, 0.88 NA. When data was collected by R/A, a small amount of sample was transferred to a low-E microscope slide (Smiths Detection P/N: 006-4013) and dispersed to a thin layer. An FT-IR spectral background was collected immediately prior to each sample spectral analysis. All experiments were conducted using a Smiths Detection (Danbury, CT) IlluminatIR 1.5™ Infrared Microspectrometer accessory on an Olympus Series BX51TRF polarized light microscope (Olympus America Inc., Melville, NY), which provided the base optical platform. The IlluminatIR 1.5 was equipped with a gray body ceramic infrared source, a 60® Michelson Interferometer with a zinc-selenide (ZeSe) beam splitter, 4 wave-number (cm-1) spectral resolution, a 0.25×0.25 mm liquid nitrogen cooled mercury, cadmium, and telluride (MCT) photoconductive detector, and the sample area was defined using a fixed circular 100 μm aperture. The IlluminatIR 1.5™ was computer interfaced using universal serial bus (USB) communications with Smiths Detection, QualID App version 2.51 software (2005). Advanced data processing was conducted using either Thermo Galactic spectral analysis software packages GRAMS/AIR and SpectralID or Thermo Fisher Scientific OMNIC software version 9.11.706 (2020). IR peak positions were determined via the “find peaks” functionality of OMNIC. The threshold was set above the baseline of the data such that any noise in the baseline would not be labelled. The sensitivity was selected such that all peaks were labelled. Shoulders were not labelled.

Proton NMR Spectroscopy (1H NMR) (FIGS. 4 and 5). The solution NMR spectra were acquired with a Bruker 500 MHz spectrometer using a 5-mm PABBO BB probe. The samples were prepared by dissolving approximately 8 mg of sample in DMSO-d6. Chemical shifts were reported in ppm relative to TMS using the residual solvent signal in the 1H NMR spectrum as internal reference. The data acquisition parameters were displayed on the plot of each spectrum.

Raman Microscopy Sample Preparation and Analysis (FIG. 2). The samples were prepared for analysis by placing a small amount of material onto a gold-plated microscope slide using a tungsten needle and dispersed to a thin layer of agglomerated particles. A HORIBA Scientific XploRA Series Confocal Raman Microscope (Piscataway, NJ) was used to collect Raman spectra using the following parameters: 785 nm laser at 50% or 100% power, 1200 g/mm grating, 100 micrometer confocal hole, 100 micrometer slit entrance to the spectrograph, and 1 second spectral acquisition with 30 accumulations. The Raman signal was detected using a Sincerity Model 356399, thermoelectrically cooled-CCD detector. Spectra were acquired over the range-100 to 3400 cm-1. An Olympus Series BX51TRF polarized light microscope (Olympus America Inc., Melville, NY) provided the base optical platform. An Olympus MPlan N Series 20X, 0.40 NA microscope objective was used to focus the laser light onto the sample and to collect the Raman signal. The microscope was equipped with a Marzhauser Wetzlar computer-controlled mapping stage to translate the sample for focus and data acquisition. System calibration was performed prior to analysis using a silicon disc to monitor peak position at 520.7 cm-1. Raman peak positions were determined via the "find peaks" functionality of OMNIC. The threshold was set above the baseline of the data such that any noise in the baseline would not be labelled. The sensitivity was selected such that all peaks were labelled. Shoulders were not labelled.

TGA Sample Preparation and Analysis (FIG. 6). TG analyses were performed using a TA Instruments model 55. Temperature calibration was performed using Alumel™. Each sample was placed in a platinum pan then inserted into the TG furnace. The furnace was heated under a purge of nitrogen (40 cc/min). Samples were analyzed in a single run from ambient temperature to 350° C. at a heating rate of 10° C./min.

While the above text may reference or exemplify specific embodiments of the disclosure, it is not intended to limit the scope of the disclosure to such particular reference or examples. Various modifications may be made by those skilled in the art, in view of practical and economic considerations.

What is claimed is:

1. A stable oral suspension comprising lamotrigine hemifumarate anhydrate, wherein the amount of lamotrigine hemifumarate anhydrate is equivalent to from 1 mg/mL to 50 mg/mL of lamotrigine (free base), wherein the stable oral suspension is in the form of a liquid, and wherein the lamotrigine hemifumarate anhydrate has an x-ray powder diffraction pattern comprising one or more peaks at 7.0°±0.2° 2θ, 13.4°±0.2° 2θ, 14.1°±0.2° 2θ, 15.1°±0.2° 2θ, 17.5°±0.2° 2θ, 22.1°±0.2° 2θ, and 24.9°±0.2° 2θ.

2. The stable oral suspension according to claim 1, wherein the amount of lamotrigine hemifumarate anhydrate is equivalent to 5 mg/ml of lamotrigine (free base).

3. The stable oral suspension according to claim 1, wherein the amount of lamotrigine hemifumarate anhydrate is equivalent to 25 mg/mL of lamotrigine (free base).

4. The stable oral suspension according to claim 1, wherein the suspension comprises a salting agent.

5. The stable oral suspension according to claim 1, wherein the suspension comprises a suspending agent.

6. The stable oral suspension according to claim 1, wherein the amount of solubilized lamotrigine (free base) in the suspension is less than 1%.

7. The stable oral suspension according to claim 1, wherein the pH is from 3.0 to 5.0.

8. The stable oral suspension according to claim 1, wherein the composition is stable for six months after being stored at room temperature.

9. The stable oral suspension according to claim 4, wherein the amount of solubilized lamotrigine (free base) in the composition is less than 1%.

10. The stable oral suspension according to claim 4, wherein the pH is from 3.0 to 5.0.

11. The stable oral suspension according to claim 4, wherein the composition is stable for six months after being stored at room temperature.

12. The stable oral suspension according to claim 1, wherein the amount of lamotrigine hemifumarate anhydrate is equivalent to 1 mg/mL of lamotrigine (free base).

* * * * *